(12) United States Patent
Murgita

(10) Patent No.: US 7,423,024 B2
(45) Date of Patent: Sep. 9, 2008

(54) RECOMBINANT HUMAN ALPHA-FETOPROTEIN AS AN IMMUNOSUPPRESSIVE AGENT

(75) Inventor: Robert A. Murgita, Montreal (CA)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 256 days.

(21) Appl. No.: 10/838,476

(22) Filed: May 4, 2004

(65) Prior Publication Data
US 2005/0026815 A1 Feb. 3, 2005

Related U.S. Application Data

(63) Continuation of application No. 09/940,308, filed on Aug. 27, 2001, now Pat. No. 6,774,108, which is a continuation-in-part of application No. 09/186,723, filed on Nov. 5, 1998, now Pat. No. 6,288,034, which is a continuation of application No. 08/377,309, filed on Jan. 24, 1995, now Pat. No. 5,965,528.

(51) Int. Cl.
*A61K 31/70* (2006.01)
*C12Q 1/68* (2006.01)

(52) U.S. Cl. ............................ 514/44; 435/6
(58) Field of Classification Search ............ 435/6
See application file for complete search history.

(56) References Cited

U.S. PATENT DOCUMENTS

| | | | | |
|---|---|---|---|---|
| 4,692,332 | A | 9/1987 | McMichael | 424/88 |
| 4,877,610 | A | 10/1989 | McMichael | 424/88 |
| 4,966,753 | A | 10/1990 | McMichael | 424/88 |
| 4,970,071 | A | 11/1990 | McMichael | 424/88 |
| 4,996,193 | A | 2/1991 | Hewitt et al. | 514/11 |
| 5,130,415 | A | 7/1992 | Tecce et al. | 530/324 |
| 5,206,153 | A | 4/1993 | Tamaoki et al. | 435/69.7 |
| 5,302,698 | A | 4/1994 | Morinaga et al. | 530/350 |
| 5,365,948 | A | 11/1994 | McMichael | 128/898 |
| 5,384,250 | A | 1/1995 | Murgita | 435/69.6 |
| 5,723,585 | A | 3/1998 | Baker et al. | 530/413 |
| 5,965,528 | A * | 10/1999 | Murgita | 514/12 |
| 6,288,034 | B1 * | 9/2001 | Murgita | 514/12 |
| 6,331,611 | B1 | 12/2001 | Murgita | 530/350 |
| 6,774,108 | B2 * | 8/2004 | Murgita | 514/12 |

FOREIGN PATENT DOCUMENTS

| | | |
|---|---|---|
| EP | 0 487 229 | 9/1997 |
| JP | 2005866 | 1/1990 |
| WO | WO 86/04241 | 7/1986 |
| WO | WO 94/10199 | 5/1994 |
| WO | WO 96/22787 | 8/1996 |
| WO | WO 01/15709 | 3/2001 |

OTHER PUBLICATIONS

Irony-Tur-Sinai et al. Experimental Neurology, vol. 198, pp. 136-144, 2004.*
Parker et al. Protein Expression and Purification, vol. 38, pp. 177-183, 2004.*
Abramsky et al., "Alpha-Fetoprotein Suppresses Experimental Allergic Encephalomyelitis," *Journal of Neuroimmunology* 2:1-7 (1982).
Abramsky et al., "A Role of Alpha-Fetoprotein in Autoimmune Diseases," *Annals New York Academy of Sciences* 417:108-116 (1983).
Aoyagi et al., "Differential Reactivity of Alpha-Fetoprotein with Lectins and Evaluation of its Usefulness in the Diagnosis of Hepatocellular Carcinoma," *Gann* 75:809-815 (1984).
Biddle et al., " Specific Cytoplasmic Alpha-Fetoprotein Binding Protein in MCF-7 Human Breast Cancer Cells and Primary Breast Cancer Tissue," *Breast Cancer Research and Treatment* 10:279-286 (1987).
Boismenu et al., "Expression of Domains of Mouse Alpha-Fetoprotein in *Escherichia Coli*," *Life Sciences* 43:673-681 (1988).
Brenner et al., "Inhibitory Effect of Alpha-Fetoprotein on the Binding of Myasthenia Gravis Antibody to Acetylcholine Receptor," *Proc. Natl. Acad. Sci. USA* 77: 3635-3639 (1980).
Brenner et al., "Immunosuppression of Experimental Autoimmune Myasthenia Gravis by Alpha-Fetoprotein Rich Formation," *Immunology Letters* 3:163-167 (1981).
Brenner et al., "Influence of Alpha-Fetoprotein on the in Vitro and in Vivo Immune Response to Acetylcholine Receptor," *Annals New York Academy of Sciences* 377:208-221 (1981).
Buamah et al., "Serum Alpha-Fetoprotein Heterogeneity as a Means of Differentiating Between Primary Hepatocellular Carcinoma and Hepatic Secondaries," *Clinica. Chimica. Acta.* 139:313-316 (1984).
Buschman et al., "Experimental Myasthenia Gravis Induced in Mice by Passive Transfer of Human Myasthenic Immunoglobulin," *Journal of Neuroimmunology* 13:315-330 (1987).
Caturla et al., "The Thyroid Hormone Down-Regulates the Mouse Alpha-Foetoprotein Promoter," *Molec. and Cell. Endocrin.* 135:139-145 (1997).
Cohen et al., "Suppression by Alpha-Fetoprotein of Murine Natural Killer Cell Activity Stimulated in Vitro and in Vivo by Interferon and Interleukin 2," *Scand. J. Immunol.* 23:211-223 (1986).
Dattwyler et al., "Binding of Alpha-Foetoprotein to Murine T Cells," *Nature* 256:656-657 (1975).
Flalova et al., "Serum Levels of Trophoblast-Specific Beta-1-Globulin (SP1) and Alpha-1-Fetoprotein (AFP) in Pregnant Women With Rheumatoid Arthritis," *Ceskoslovenska Gynekologie* 56:166-170 (1991) (Abstract only).
Galarneau et al., "The Alpha$_1$-Fetoprotein Locus is Activated by a Nuclear Receptor of the *Drosophilia* FTZ-F1 Family," *Molec. and Cell. Biol.* 16:3853-3865 (1996).
Gershwin et al., "The Influence of Alpha-Fetoprotein on Moloney Sarcoma Virus Oncogenesis: Evidence for Generation of Antigen Nonspecific Suppressor T Cells," *The Journal of Immunology* 121:2292-2297 (1978).
Giuliani et al., "Synthesis and Characterization of a Recombinant Fragment of Human Alpha-Fetoprotein with Antigenic Selectivity Versus Albumin," *Protein Engineering* 2:605-610 (1989).
Glazier et al., "Graft-Versus-Host Disease in Cyclosporin A-Treated Rats After Syngeneic and Autologous Bone Marrow Reconstitution," *J. Exp. Med.* 158:1-8 (1983).

(Continued)

*Primary Examiner*—Gary Benzion
*Assistant Examiner*—Cynthia Wilder
(74) *Attorney, Agent, or Firm*—Clark & Elbing LLP

(57) ABSTRACT

Disclosed are methods of inhibiting autoreactive immune cell proliferation in a mammal, involving administering to the mammal a therapeutically effective amount of recombinant human alpha-fetoprotein or an immune cell anti-proliferative fragment or analog thereof.

8 Claims, 30 Drawing Sheets

OTHER PUBLICATIONS

Goidl et al., "Studies on the Mechanisms of Alpha-Fetoprotein Induction of Immune Suppressive Activity," from *Developmental Immunobiology, Proceedings of the Fifth Irwin Strasburger Memorial Seminar on Immunology* eds. Siskind et al., 35-55 (1979).

Hamel et al., "Phenotype and Function of Bone Marrow-Derived T- and Non-T-Cells Activated in Vitro by Alpha-Fetoprotein," *Biological Activities of Alpha$_1$-Fetoprotein* 1:167-177 (1987).

Heyward et al., "Early Detection of Primary Hepatocellular Carcinoma by Screening for Alpha-Fetoprotein in High-Risk Famillies," *The Lancet* 2:1161-1162 (1983).

Hooper et al., "Regulation of Murine T-Cell Responses to Autologous Antigens by Alpha-Fetoprotein," *Celluar Immunology* 63:417-425 (1981).

Hooper et al., "Suppression of Primary and Secondary Autologous Mixed Lymphocyte Reactions by Murine Alphafetoprotein," *Oncodevelopmental Biology and Medicine* 3:151-160 (1982).

Hooper et al., "Selective Inhibition of Murine T-Cell Proliferation and Lymphokine-Activated Natural Killer Cell Function by Alpha-Fetoprotein," *Biological Activities of Alpha$_1$-Fetoprotein* eds. Mizejewski et al. 1:153-165 (1987).

Hooper et al., "Human AFP Inhibits Cell Proliferation and NK-Like Cytotoxic Activity Generated in Autologous, but not in Allogeneic Mixed Lymphocyte Reactions," *Biological Activities of Alpha$_1$-Fetoprotein* 2:183-197 (1989).

Hoskin et al., "In Vitro Activation of Bone Marrow-Derived T-and Non-T-Cell Subsets by Alpha-Fetoprotein," *Cellular Immunology* 96:163-174 (1985).

Hoskin et al., "Analysis of Pregnancy-Associated Immunoregulatory Pathways," *Alpha-Fetoprotein and Congenital Disorders* 59-78 (1985).

Hoskin et al., "Specific Maternal Anti-Fetal Lymphoproliferative Responses and Their Regulation by Natural Immunosuppressive Factors," *Clin. Exp. Immunol.* 76:262-267 (1989).

Innis et al., "Amplification of Alpha-Fetoprotein Complementary DNA by Insertion into a Bacterial Plasmid," *Archives of Biochemistry and Biophysics* 195:128-135 (1979).

Ishiguro et al., "Serum Alpha-Fetoprotein Subfractions in Patients with Primary Hepatoma or Hepatic Metastasis of Gastric Cancer," *Cancer* 55:156-159 (1985).

Jacobson et al., "Inhibition of Estrogen-Dependent Breast Cancer Growth by a Reaction Product of Alpha-Fetoprotein and Estradiol, " *Cancer Research* 50:415-420 (1990).

Jiang et al., "Role of CD8+ T Cells in Murine Experimental Allergic Encephalomyelitis," *Science* 256:1213-1215 (1992).

Karasuyama et al., "Establishment of Mouse Cell Lines which Constitutively Secrete Large Quantities of Interleukin 2, 3, 4 or 5, Using Modified cDNA Expression Vectors," *Eur. J. Immunol.* 18:97-104 (1998), Keller et al., "Immunosuppressive Properties of AFP: Role of Estrogens," form Onco-Developmental Gene Expression eds. Fishman et al. 287-295 (1976).

Kikutani et al., "The Murine Autoimmune Diabetes Model: NOD and Related Strains," *Advances in Immunology* 51:285-322 (1992).

Line et al., "Medical Potential of AFP as a Tumor Imaging Agent," *Biological Activities of Alpha$_1$-Fetoprotein* 2:139-148 (1989).

Lu et al., "Alpha-Fetoprotein Inhibits Macrophage Expression of Ia Antigens," *The Journal of Immunology* 132:1722-1727 (1984).

Masuda et al., "Selective Antitumor Effect of Thioether-Linked Immunotoxins Composed of Gelonin and Monoclonal Antibody to Alpha-Fetoprotein or its F(ab')$_2$ Fragment," *Tumor Biol.* 15:175-183 (1994).

Mizejewski, "Alpha-Fetoprotein Testing: Regulatory and Technical Considerations," *Laboratory Management* (1987).

Morinaga et al., "Primary Structures of Human Alpha-Fetoprotein and its mRNA," *Proc. Natl. Acad. Sci. USA* 80:4604-4608 (1983).

Moro et al., "Monoclonal Antibodies Directed Against a Widespread Oncofetal Antigen: The Alpha-Fetoprotein Receptor," *Tumor Biol.* 14:116-130 (1993).

Murgita et al., "Suppression of the Immune Response by Alpha-Fetoprotein I. The Effect of Mouse Alpha-Fetoprotein on the Primary and Secondary Antibody Response," *The Journal of Experimental Medicine* 141:269-286 (1975).

Murgita et al., "Suppression of the Immune Response by Alpha-Fetoprotein II. The Effect of Mouse Alpha-Fetoprotein on Mixed Lymphocyte Reactivity and Mitogen-Induced Lymphocyte Transformation," *The Journal of Experimental Medicine* 141:440-452 (1975).

Murgita, "The Immunosuppressive Role of Alpha-Fetoprotein During Pregnancy," *Scand. J. Immunol.* 5:1003-1014 (1976).

Murgita et al., "The Effects of Mouse Alpha-Fetoprotein on T-Cell Dependent and T-Cell-Independent Immune Responses in Vitro," *Scand. J. Immunol.* 5:1215-1220 (1976).

Murgita et al., "Alpha-Fetoprotein Induces Suppressor T Cells in Vitro," *Nature* 267:257-259 (1977).

Murgita et al., "Adult Murine T Cells Activated in Vitro by Alpha-Fetoprotein and Naturally Occurring T Cells in Newborn Mice: Identity in Function and Cell Surface Differentiation Antigens," *Proc. Natl. Acad. Sci. USA* 75:2897-2901 (1978).

Murgita et al., "Effects of Human Alpha-Foetoprotein on Human B and T Lymphocyte Proliferation in Vitro," *Clin. Exp. Immunol.* 33:347-356 (1978).

Murgita et al., "Characterization of Murine Newborn Inhibitory T Lymphocytes: Functional and Phenotypic Comparison with an Adult T Cell Subset Activated in Vitro by Alpha-Fetoprotein," *Eur. J. Immunol.* 11:957-964 (1981).

Murgita et al., "Regulation of Immune Functions in the Fetus and Newborn," *Prog. Allergy* 29:54-133 (1981).

Nelson et al., "Maternal-Fetal Disparity in HLA Class II Alloantigens and the Pregnancy-Induced Amelloration of Rheumatoid Arthritis," *The New England Journal of Medicine* 329:466-471 (1993).

Nishl et al., "Expression of Rat Alpha-Fetoprotein cDNA in *Escherichia coli* and in Yeast," *J. Biochem.* 104:968-972 (1988).

O'Neill et al., "Regulation of Human Lymphocyte Activation by Alpha-Fetoprotein: Evidence for Selective Suppression of Ia-Associated T-Cell Proliferation in vitro," *Oncodevelopmental Biology and Medicine* 3:135-150 (1982).

Peck et al., "Cellular and Genetic Restrictions in the Immunoregulatory Activity of Alpha-Fetoprotein I. Selective Inhibition of Anti-Ia-Associated Proliferative Reactions," *J. Exp. Med.* 147:667-683 (1978).

Peck et al., "Cellular and Genetic Restrictions in the Immunoregulatory Activity of Alpha-Fetoprotein II. Alpha-Fetoprotein-Induced Suppression of Cytotoxic T Lymphocyte Development," *J. Exp. Med.* 148:360-372 (1978).

Peck et al., "Cellular and Genetic Restrictions in the Immunoregulatory Activity of Alpha-Fetoprotein III. Role of the MLC-Stimulating Cell Population in Alpha-Fetoprotein-Induced Suppression of T Cell-Mediated Cytotoxicity," *J. of Immunology* 128:1134-1140 (1982).

Sambrook et al., "Expression of Cloned Genes in *Escherichia coli,*" *Molecular Cloning* 17:37-43 (1989).

Semenluk et al., "Evidence that Immunosuppression is an Intrinsic Property of the Alpha-Fetoprotein Molecule,"0 *Adv. Exp. Med. Biol.* 383:255-269 (1995).

Soto et al., "Control of Growth of Estrogen-Sensitive Cells: Role for Alpha-Fetoprotein," *Proc. Natl. Acad. Sci. USA* 77:2084-2087 (1980).

van Oers, et al., "Isolation and Characterization of a Distinct Immunoregulatory Isoform of Alpha-Fetoprotein Produced by the Normal Fetus," *J. Exp. Med.* 170:811-825 (1989).

Villacampa et al., "Alpha-Fetoprotein Receptors in a Human Breast Cancer Cell Line," *Biochemical and Biophysical Research Communications* 122:1322-1327 (1984).

Wang et al., "Downregulation of Phorbol 12-Myristate 13-Acetate-Induced Tumor Necrosis Factor-Alpha and Interleukin-1 Beta Production and Gene Expression in Human Monocytic Cells by Human Alpha-Fetoprotein," *Hepatology* 22:921-928 (1995).

Yamamoto et al., "Expression of Human Alpha-Fetoprotein in Yeast," *Life Sciences* 46:1679-1686 (1990).

* cited by examiner

FIG. 5

Inhibition of the AMLR[a] by recombinant baculovirus and *E. coli* derived AFP: Blocking of immunosuppression with monoclonal anti-natural HuAFP antibodies

| Protein Addition to Culture[b] | AMLR[a] [$^3$H-Thymidine Incorporation] | |
|---|---|---|
| | No Ab (% suppression)[d] | Anti-human AFP[c] (% suppression) |
| Experiment 1 | | |
| None | 41,333 ± 6,233 (-) | 47,137 ± 4,765 (-) |
| Albumin | 50,187 ± 6,870 (-) | - |
| Recombinant Baculo AFP | 18,890 ± 1,240 (54) | 48,588 ± 5,697 (-) |
| Experiment 2 | | |
| None | 41,722 ± 7,544 (-) | 38,898 ± 5,091 (6) |
| Albumin | 73,496 ± 8,805 (-) | - |
| Recombinant *E.coli* AFP | 17,316 ± 2,006 (58) | 42,926 ± 7,676 (-) |
| Experiment 3 | | Endotoxin (ng/µg protein) |
| None | 67,917 ± 8,384 | - |
| *E.coli* AFP Prior to Detoxigel | 20,439 ± 1,186 | 0.12 |
| *E.coli* AFP After Detoxigel | 21,400 ± 2,274 | 0.024 |

[a] AMLR cultures were set up with 2 X 10$^5$ responding T cells with 2.5 X 10$^5$ irradiated autologous non-T cells in the presence or absence of protein, harvested at 144 hours and autoproliferation was measured by the amount of $^3$H-thymidine incorporated by proliferating T cells.

[b] 100 µg/ml of protein was added at the initiation of culture.

[c] Blocking of the anti-proliferative effects of rHuAFP was carried out by adding murine anti-human AFP monoclonal antibodies (Mab) at a dilution of 1/8 (125mg/ml) to AMLR cultures.

[d] $\% \text{ suppression} = 1 - \dfrac{\text{cultures with protein additions}}{\text{cultures with no protein additions}} \times 100$

FIG. 6

Comparison of the immunosuppressive effects of recombinant baculovirus, *E. coli*, and Δ(1-226) derived AFP on mitogen stimulated peripheral blood lymphocytes[a] in serum-free media

| Protein Addition to | Con A Stimulated Peripheral Blood | |
|---|---|---|
| | $^3$H-Thymidine | (% Suppression)[c] |
| Experiment 1 | | |
| None | 102,353 ± 5,566 | - |
| Albumin | 95,151 ± 3,362 | 7 |
| Recombinant Baculo AFP | 37,288 ± 1,927 | 64 |
| Experiment 2 | | |
| None | 91,502 ± 4,333 | - |
| Albumin | 93,943 ± 1,698 | - |
| Recombinant *E.coli* AFP | 35,531 ± 6,645 | 61 |
| Experiment 3 | | |
| None | 99,700 ± 4,464 | - |
| Albumin | 94,123 ± 1,633 | 6 |
| Recombinant *E.coli* AFP | 49,927 ± 7,082 | 50 |
| Δ(1-226) *E.coli* AFP | 39,019 ± 161 | 61 |

[a] Con A cultures were set up in RPMI media supplemented with only 2 mg/ml HSA and 2 X 10$^5$ PBL's in the presence or absence of protein, harvested at 48 hours and proliferation was measured by the amount of $^3$H-thymidine incorporated by mitogen transformed lymphocytes.

[b] 100 μg/ml of protein was added at the initiation of culture.

[c] % suppression = $1 - \dfrac{\text{cultures with protein additions}}{\text{cultures with no protein additions}} \times 100$

FIG. 8-1

```
                                                                                   AT  (2)
                         -19                         -10                           -1
              met lys trp val gln ser ile phe leu ile phe leu leu asn phe thr glu ser arg
ATTGTGCTTCCACCACTGCCAATAACAAAATAACTAGCAACC ATG AAG TGG GTG GAA TCA ATT TTT TTA CTA AAT TTT ACT GAA TCC AGA (101)

1                         10                        20                       30
thr leu his arg asn glu tyr gly ile ala ser ile leu asp ser tyr gln cys thr ala glu ile ser leu ala asp leu ala thr ile
ACA CTG CAT AGA AAT GAA TAT GGA ATA GCT TCC ATA TTG GAT TCT TAC CAA TGT ACT GCA GAG ATA AGT GCT GAC CTG GCT ACC ATA (191)

31                         40                        50                       60
phe phe ala gln phe val gln glu ala thr tyr lys glu val ser lys met val lys glu ala ile glu lys pro thr gly
TTT TTT GCC CAG TTT GTT CAA GAA GCC ACT TAC AAG GAA GTA AGC ATG GTG AAA GAA GCA ATT GAG AAA CCC ACT GGA (281)

61                         70                        80                       90
asp glu gln ser ser gly cys leu glu asn gln leu pro ala phe leu glu asn cys phe his glu lys lys tyr gly
GAT GAA GAG TCT TCA GGG TGT TTA GAA AAC CAG CTA CCT GCC TTT CTG GAA AAT TGT TTT CAT GAG AAG AAG TAC GGA (371)

91                        100                       110                      120
his ser asp cys cys ser lys gln gly gly arg his asn cys phe leu ala his lys lys lys pro thr pro ala ser ile pro leu phe
CAT TCA GAC TGC TGC AGC AAA CAA GGA GGA AGA CAT AAC TGT TTT CTT GCA CAC AAG AAA AAG CCC ACC GCA TCG ATC CCA CTT TTC (461)

121                        130                       140                      150
gln val pro glu pro val thr ser cys glu ala tyr gln glu asp arg glu thr phe met asn lys phe ile tyr glu ile ala arg arg
CAA GTT CCA GAA CCT GTC ACA AGC TGT GAA GCA TAT CAA GAA GAC AGG GAG ACA TTC ATG AAC AAA TTC ATT TAT GAG ATA GCA AGA AGG (551)

151                        160                       170                      180
his pro phe leu tyr ala ala pro thr ile leu leu trp ala ala arg tyr asp lys ile ile pro ser cys cys lys ala glu asn ala val
CAT CCC TTC CTG TAT GCA GCT CCT ACA ATT CTT CTT TGG GCT GCT CGC TAT GAC AAA ATA ATT CCA TCT TGC TGC AAA GCT GAA AAT GCA GTT (641)

181                        190                       200                      210
glu cys phe gln thr lys ala ala thr val thr lys glu leu arg glu ser ser leu asn leu asn gln his ala cys val met lys asn
GAA TGC TTC CAA ACA AAG GCA GCA ACA GTT ACA AAA GAA TTA AGA GAA AGC AGC TTG TTA AAT CAA CAT GCA TGT GTA ATG AAA AAT (731)
```

FIG. 8-2

```
211 phe gly thr arg thr phe gln ala ile thr val thr lys leu ser gln lys phe thr val asn phe thr gln ile gln lys leu val  240
    TTT GGG ACC CGA ACT TTC CAA GCC ATA ACT GTT ACT AAA CTG AGT CAG AAG TTT ACC AAA GTT AAT TTT ACT CAG AAA CTA GTC (821)

241 leu asp val ala his glu his cys cys arg gly asp val leu asp cys leu gln asp gly glu lys ile met ser tyr ile cys  270
    CTG GAT GTG GCC CAT GTA CAT TGC TGT AGA GGA GAT GTG CTG GAT TGT CTT CAG GAT GGG GAA AAA ATC ATG TCC TAC ATA TGT (911)

271 ser gln gln asp thr leu ser asn lys ile thr glu cys cys lys leu thr thr leu glu arg gly gln cys ile ile his ala glu asn  300
    TCT CAA CAA GAC ACT CTA AGC AAT AAA ATA ACA GAA CAC TGC TGC AAA CTG ACC ACG CTG GAA CGT GGT CAA TGT ATA ATT CAT GCA GAA AAT (1001)

301 asp glu lys pro glu gly leu ser pro asn leu asn arg phe leu gly asp arg asp phe asn gln phe ser ser gly glu lys asn ile  330
    GAT GAA AAA CCT GAA GGT CTA TCT CCA AAT CTA AAC AGG TTT TTA GGA GAT AGA GAT TTT AAC CAA TTT TCT TCA GGG GAA AAA AAT ATC (1091)

331 phe leu ala ser phe val his glu tyr ser arg arg his pro gln leu ala val ser val ile leu arg val ala lys gly tyr gln glu  360
    TTC TTG GCA AGT TTT GTT CAT GAA TAT TCA AGA AGA CAT CCT CAG CTT GCT GTG TCA GTT ATT CTA AGA GTT GCT AAA GGA TAC CAG GAG (1181)

361 leu leu glu lys cys phe gln thr glu asn pro leu glu cys gln asp lys gly glu glu glu leu gln lys tyr ile gln glu ser gln  390
    TTA TTG GAG AAG TGT TTC CAG ACT GAA AAC CCT CTT GAA TGC CAA GAT AAA GGA GAA GAA GAA CTA CAG AAG TAC ATC CAG GAG AGC CAA (1271)

391 ala leu ala lys ser cys gly leu phe gln lys leu gly glu tyr tyr leu gln asn ala phe leu val ala tyr thr lys lys ala  420
    GCA TTG GCA AAG CGA AGC TGC GGC CTC TTC CAG AAG CTA GGA GAA TAT TAC TTA CAA AAT GCG TTT CTC GTT GCT TAC ACA AAG AAG GCC (1361)

421 pro gln leu thr ser ser glu leu met ala ile thr arg lys met ala ala thr ala thr cys cys gln leu ser glu asp lys leu  450
    CCC CAG CAG CTG ACC TCG GAG CTG ATG GCA ATC ACC AGA AAG ATG GCA GCA GCC ACA GCA GCC ACT TGT TGC CAA CTC AGT GAG GAC AAA CTA (1451)
```

FIG. 8-3

```
451                                                              460                                                                     470                                                                    480
leu ala cys gly glu gly ala ala asp ile ile ile gly his leu cys ile arg his glu met thr pro val asn pro gly val gly gln
TTG GCC TGT GGC GAG GGA GCG GCT GAC ATT ATT ATC GGA CAC TTA TGT ATC AGA CAT GAA ATG ACT CCA GTA AAC CCT GGT GTT GGC CAG(1541)

481                                                              490                                                                     500                                                                    510
cys cys thr ser ser tyr ala asn arg arg pro cys phe ser ser leu val val asp glu thr tyr val pro pro ala phe ser asp asp
TGC TGC ACT TCT TCA AGT GCC AAC AGG AGG CCA TGC TTC AGC TCT CTG GTG GTG GAT GAA ACA TAT GTC CCT CCT GCA TTC TCT GAT GAC(1631)

511                                                              520                                                                     530                                                                    540
lys phe ile phe his lys asp leu cys gln ala gln leu gln val ala leu gln thr met lys gln glu phe leu ile asn leu val lys gln
AAG TTC ATT TTC CAT AAG GAT CTG TGC CAA GCT CAG CTG CAA GTA GCG CTG CAA ACG ATG AAG CAA GAG TTT CTC ATT AAC CTT GTG AAG CAA(1721)

541                                                              550                                                                     560                                                                    570
lys pro gln ile thr glu glu gln ile thr glu glu ala val ile ala asp phe ser gly leu leu glu lys cys cys gln gly leu gln glu glu
AAG CCA CAA ATA ACA GAG GAA CAA CTT GAG GCT GTC ATT GCA GAT TTC TCA GGC CTG TTG GAG AAA TGC TGC CAA GGC CAG GAA CAG GAA(1811)

571                                                              580                                                                     590
val cys phe ala glu gln gly lys leu ile ser lys thr arg ala ala leu gly val ter
GTC TGC TTT GCT GAA GAG GGA CAA AAA CTG ATT TCA AAA ACT CGT GCT GCT TTG GGA GTT TAA     ATTACTTCAGGGGAAGAAGACAAAACGAGTCT(1908)

TTCATTCGGTGTGAACTTTTCTCTTTAATTTTAACTGATTTAACACTTTTTGTGAATTAATGAAATGATAAAGACTTTTATGTGAGATTCCTTATCACAGAAATAAAATATCTCCAAA(2027)
```

FIG. 12A
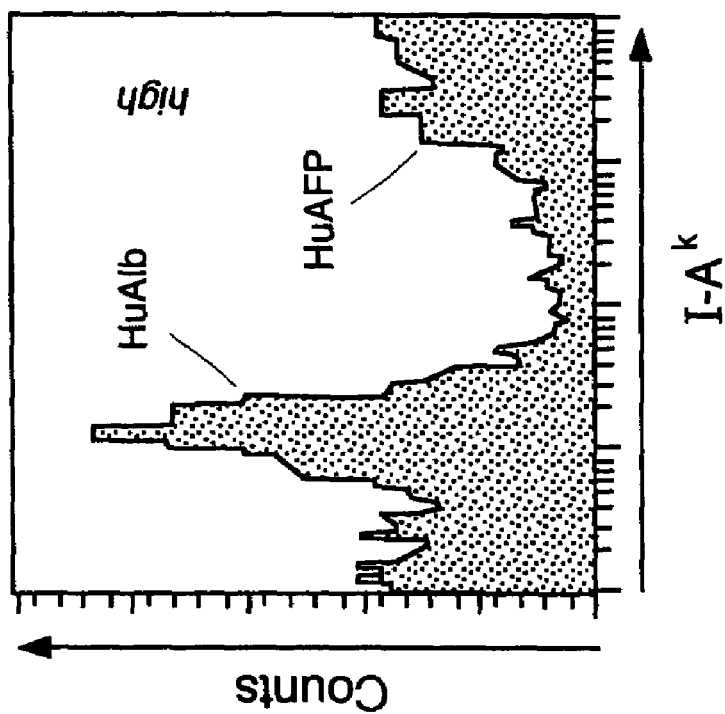
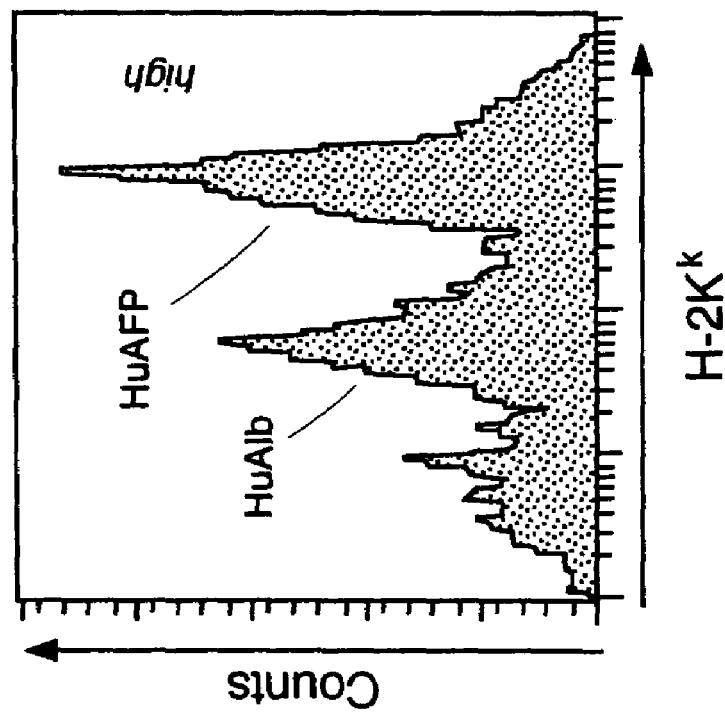

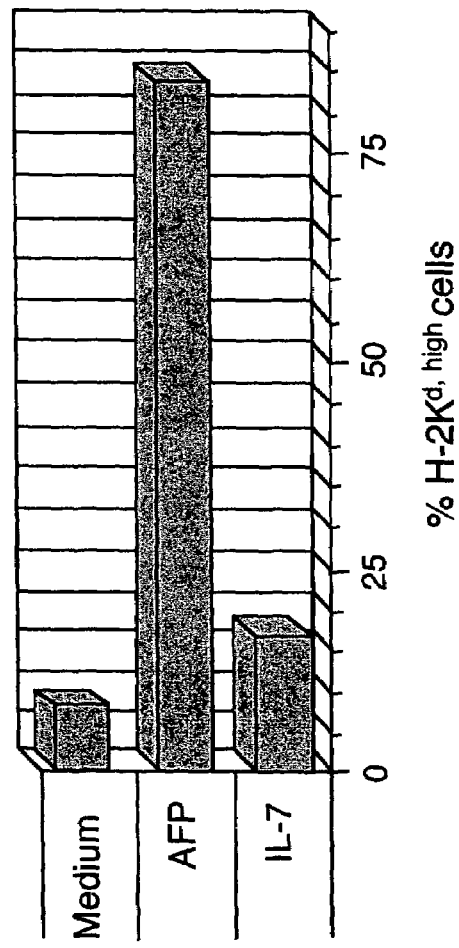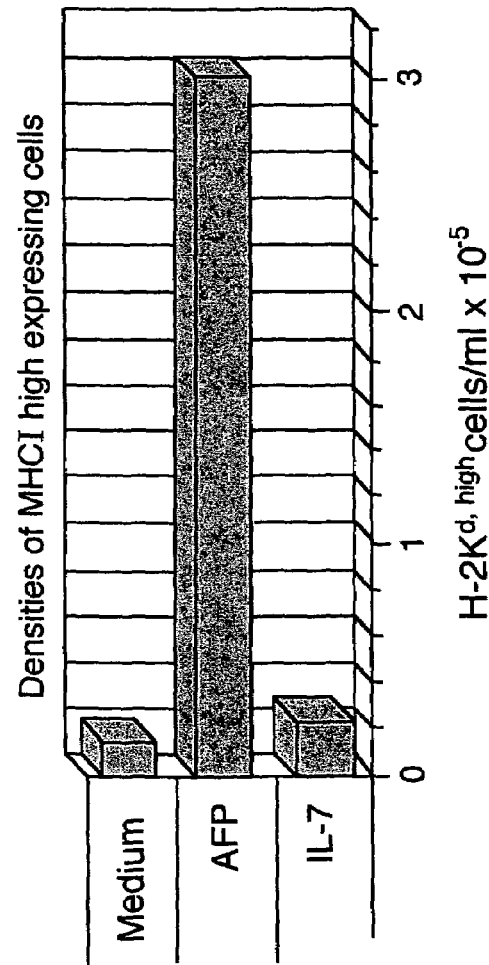
FIG. 15A

RECOMBINANT HUMAN ALPHA-FETOPROTEIN AS AN IMMUNOSUPPRESSIVE AGENT

CROSS-REFERENCE TO RELATED APPLICATIONS

This application is a continuation of U.S. Ser. No. 09/940,308, filed Aug. 27, 2001 now U.S. Pat. No. 6,774,108, which is a continuation-in-part of U.S. Ser. No. 09/186,723, filed on Nov. 5, 1998, now U.S. Pat. No. 6,288,034, which is a continuation of U.S. Ser. No. 08/377,309, filed Jan. 24, 1995, now U.S. Pat. No. 5,965,528, each of which is hereby incorporated by reference.

BACKGROUND OF THE INVENTION

This invention relates to methods for treating autoimmune diseases.

Responses of the immune system initiate the destruction and elimination of invading organisms and toxic molecules produced by them. Because these immune reactions are destructive, it is essential that they be made in response only to molecules that are foreign to the host and not to those of the host itself. The ability to distinguish foreign molecules from self molecules is a fundamental feature of the immune system. Occasionally the immune system fails to make this distinction and reacts destructively against the host's own molecules; such autoimmune diseases can be fatal. Thus, tolerance to self antigens breaks down, causing the components of the immune system such as T or B cells (or both) to react against their own tissue antigens. Multiple sclerosis, rheumatoid arthritis, myasthenia gravis, insulin-dependent diabetes mellitus, and systemic lupus erythematosus are a few examples of such autoimmune diseases.

SUMMARY OF THE INVENTION

I have discovered that recombinant human alpha-fetoprotein made in a prokaryote (e.g., E. coli or baculovirus) or eukaryote is useful for inhibiting autoreactive immune cells derived from a mammal. Accordingly, the invention features a method of inhibiting transplant rejection in a mammal (e.g., a human patient), involving administering to the mammal a therapeutically effective amount of recombinant human alpha-fetoprotein or an immune cell anti-proliferative fragment or analog thereof. Preferably, such immune cells include T cells or B cells; and the recombinant human alpha-fetoprotein used in such methods is produced in a prokaryotic cell (e.g., E. coli or baculovirus) or eukaryotic (e.g., transgenic animal) and is glycosylated or unglycosylated.

In another aspect, the invention features a method of inhibiting graft-versus-host disease in a mammal (e.g., a human patient), involving administering to the mammal a therapeutically effective amount of recombinant human alpha-fetoprotein or an immune cell anti-proliferative fragment or analog thereof. Preferably, the recombinant human alpha-fetoprotein used in such methods is produced in a prokaryotic cell (e.g., E. coli or baculovirus) or eukaryotic (e.g., transgenic animal) and is glycosylated or unglycosylated.

In yet another aspect, the invention features a method of mitigating the side effects in a mammal (e.g. a human patient) undergoing chemotherapy, involving administering to the mammal a therapeutically effective amount of recombinant human alpha-fetoprotein or an immune cell anti-proliferative fragment or analog thereof. Preferably, the recombinant human alpha-fetoprotein used in such methods is produced in a prokaryotic cell (e.g., E. coli or baculovirus) or eukaryotic (e.g., transgenic animal) and is glycosylated or unglycosylated.

In an additional aspect, the invention features a method of mitigating the side effects in a mammal (e.g., a human patient) undergoing irradiation therapy, involving administering to the mammal a therapeutically effective amount of recombinant human alpha-fetoprotein or an immune cell anti-proliferative fragment or analog thereof. Preferably, the recombinant human alpha-fetoprotein used in such methods is produced in a prokaryotic cell (e.g., E. coli or baculovirus) or eukaryote (e.g., transgenic animal) and is glycosylated or unglycosylated. In other preferred embodiments, such methods further involve administering to the mammal an immunosuppressive agent in an effective dose that is lower than the standard dose when the immunosuppressive agent is used by itself. Preferably, such an immunosuppressive agent is cyclosporine; is a steroid; is azathioprine; is FK-506; or is 15-deoxyspergualin. In yet another preferred embodiment, such a method involves administering to the mammal a tolerizing agent. Preferably, the recombinant human alpha-fetoprotein used in such methods is produced in a prokaryotic cell (e.g., E. coli or baculovirus) or eukaryote (e.g., transgenic animal) and is glycosylated or unglycosylated.

By "immune cell anti-proliferative" is meant capable of inhibiting the growth of an undesirable immune cell (e.g., an autoreactive T cell as measured using the assays described herein).

By "therapeutically effective amount" is meant a dose of unglycosylated recombinant human alpha-fetoprotein (or a fragment or analog thereof) capable of inhibiting autoreactive immune cell proliferation.

By "recombinant human alpha-fetoprotein" is meant a polypeptide having substantially the same amino acid sequence as the protein encoded by the human alpha-fetoprotein gene as described by Morinaga et al., *Proc. Natl. Acad. Sci., USA* 80: 4604 (1983). The method of producing recombinant human alpha-fetoprotein in a prokaryotic cell is described in U.S. Ser. No. 08/133,773 issuing as U.S. Pat. No. 5,384,250.

According to the invention, administration of recombinant human alpha-fetoprotein ("rHuAFP") (or a fragment or analog thereof) can be an effective means of preventing or treating or ameliorating autoimmune-diseases in a mammal. To illustrate this, I have shown that recombinant HuAFP produced in a prokaryotic expression system is effective in suppressing T cell proliferation in response to self antigens, despite the fact that such rHuAFP is not modified in the same fashion as naturally occurring HuAFP. The use of natural HuAFP has heretofore been limited by its unavailability; natural HuAFP is obtained by laborious purification from limited supplies of umbilical cords and umbilical cord serum. Because biologically rHuAFP can now be prepared in large quantities using the techniques of recombinant DNA, the use of rHuAFP for treating autoimmune diseases is now possible. The use of rHuAFP is especially advantageous since there are no known adverse side effects related to human alpha-fetoprotein and it is believed that relatively high doses can be safely administered.

Other features and advantages of the invention will be apparent from the following detailed description, and from the claims.

DETAILED DESCRIPTION

The drawings will first be described.

DRAWINGS

FIG. 1A is an autoradiography showing the purity of recombinant AFP produced in *E. Coli*. (ErAFP) on a 10% non-denaturing alkaline polyacrylamide gel. Mouse amniotic fluid proteins (transferrin, AFP and albumin) are shown in lane 1, natural human AFP (HuAFP) and ErAFP are shown in lane 2 and lane 3, respectively.

FIG. 1B is an autoradiography showing the purity of ErAFP produced in *E. coli* on a 10% sodium dodecyl sulfate-polyacrylamide gel. Molecular weight markers are shown in lane 1, HuAFP and ErAFP are shown in lane 2 and lane 3, respectively.

Figure 2A:
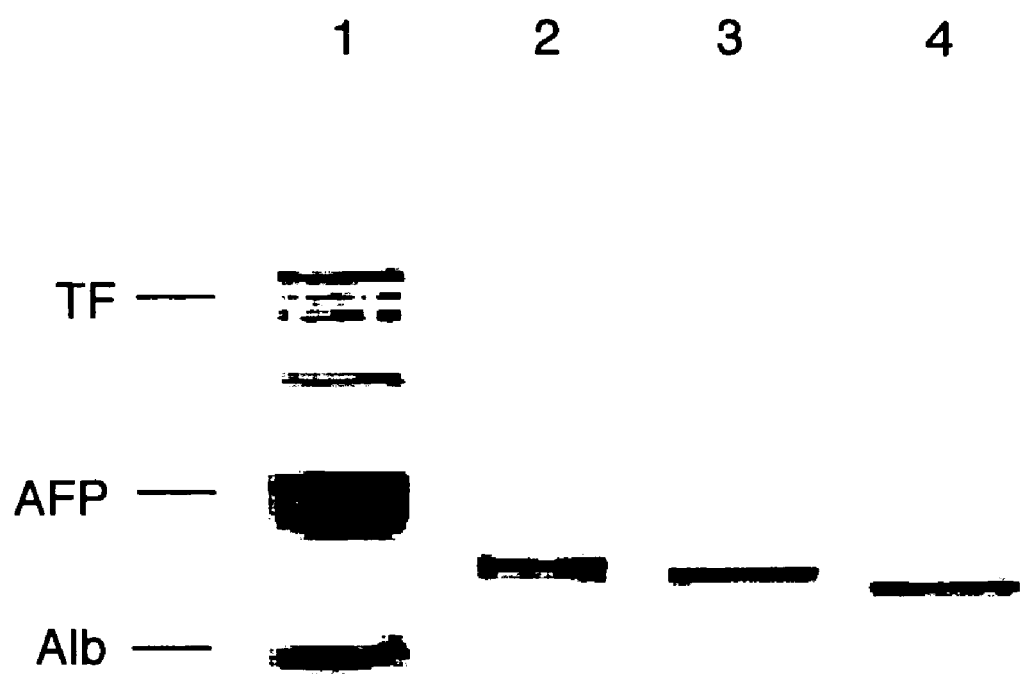

FIG. 2A is an autoradiograph showing the purity of recombinant AFP produced in baculovirus (BrAFP) on a 10% non-denaturing alkaline polyacrylamide gel. Protein samples are HuAFP (lane 2), BrAFP (lane 3), and ErAFP (lane 4). Molecular weight markers and mouse amniotic fluid are shown in lane 1.

Figure 2B:
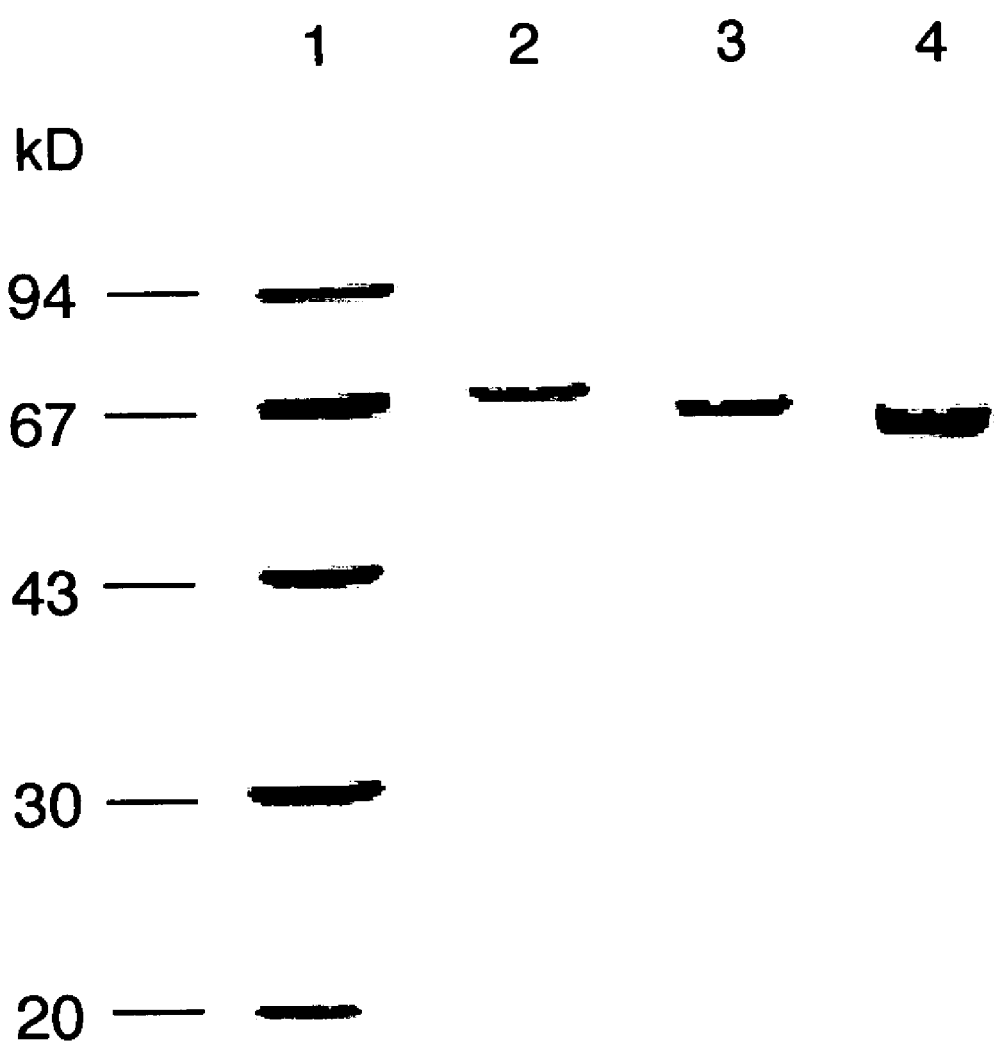

FIG. 2B is an autoradiograph showing the purity of BrAFP on 10% SDS-acrylamide gel. Protein samples are HuAFP (lane 2), BrAFP (lane 3), and ErAFP (lane 4). Molecular weight markers and mouse amniotic fluid are shown in lane 1.

Figure 2C:
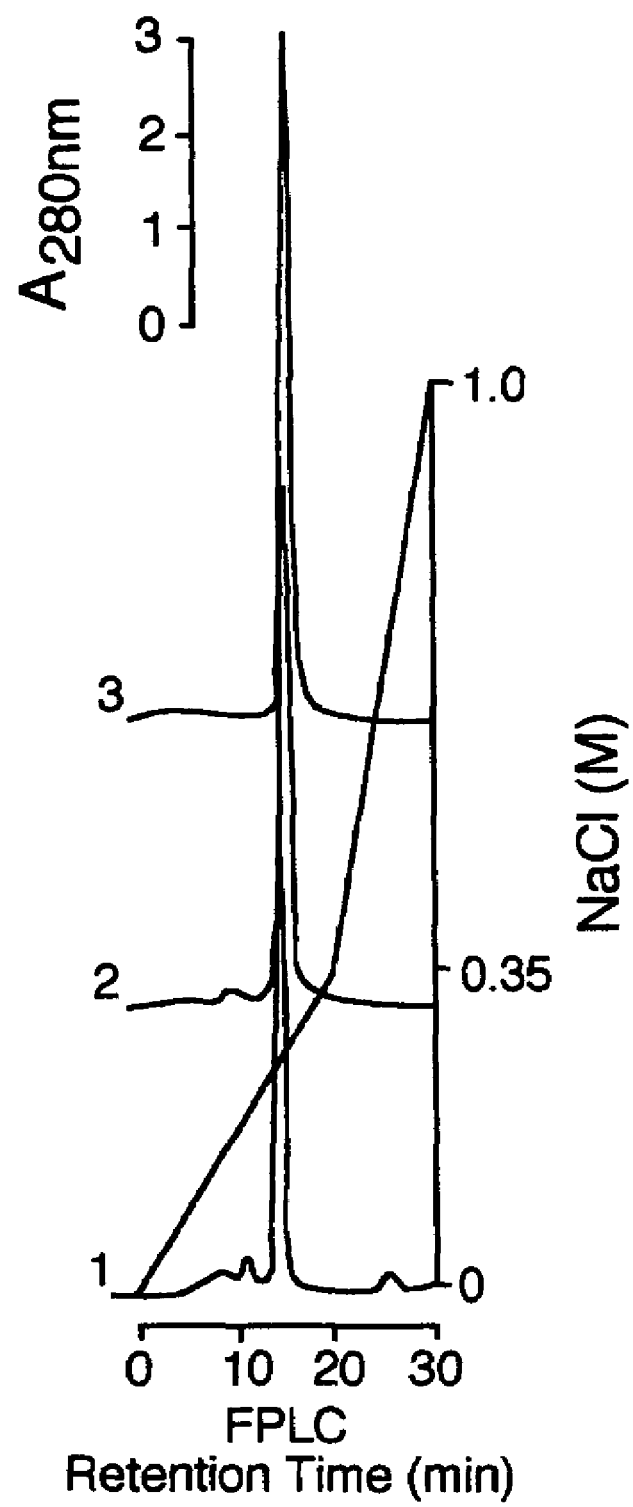

FIG. 2C is a series of FPLC chromatograms showing the elution profile of HuAFP, BrAFP, and ErAFP from a MonoQ anion exchange column. The superimposed chromatograms identify HuAFP (Chromatogram 1), BrAFP (Chromatogram 2), and ErAFP (Chromatogram 3).

Figure 2D:
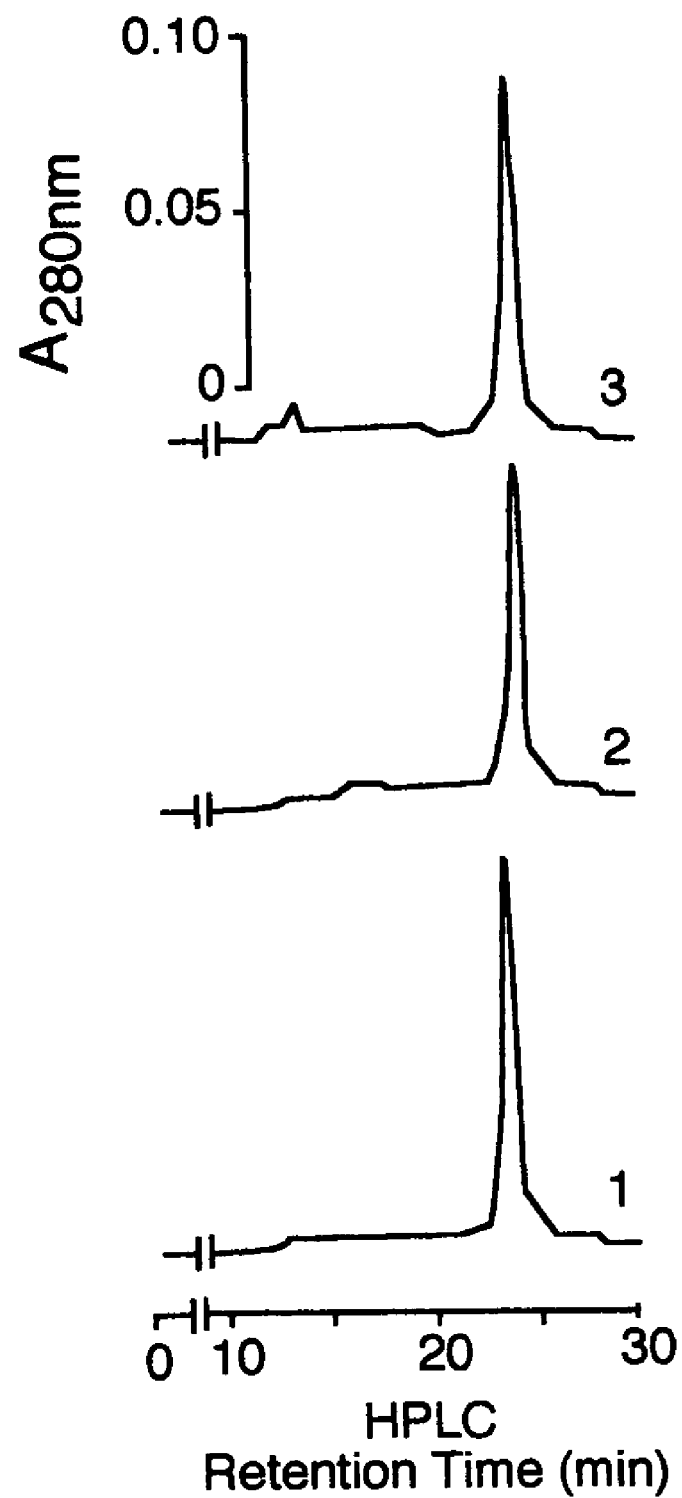

FIG. 2D is a a series of HPLC chromatograms showing the elution profile of HuAFP, BrAFP, and ErAFP obtained by passing 50 μg of HuAFP, BrAFP, and ErAFP through a reverse phase Delta Pak C18 column (Waters) and eluting with a gradient of 0-100% acetonitrile in 0.1% TFA. The superimposed chromatograms identify natural HuAFP (Chromatogram 1), BrAFP (Chromatogram 2), and ErAFP (Chromatogram 3).

Figure 3A:
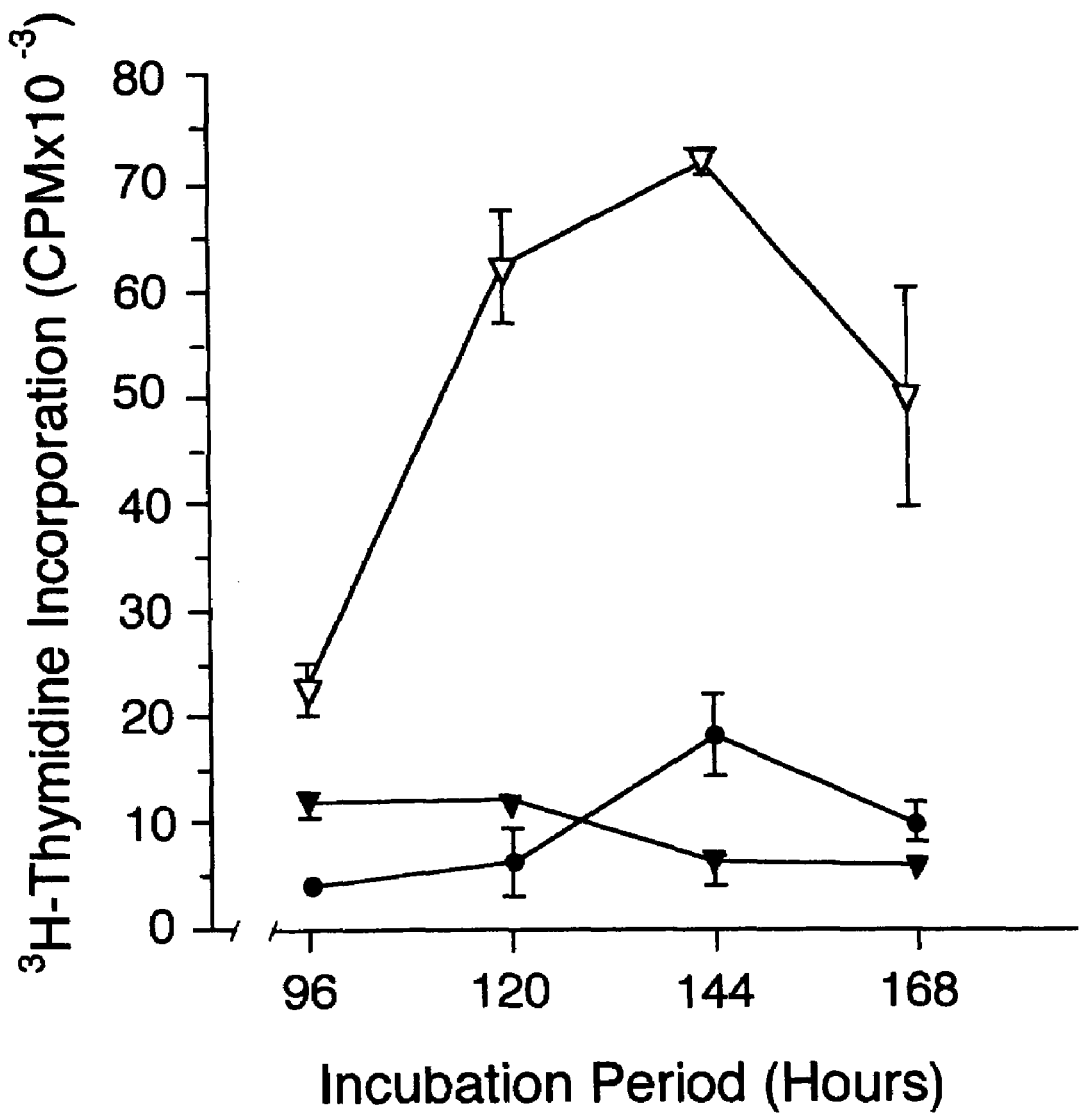

FIG. 3A is a graph showing the inhibitory effect of the ErAFP on the kinetics of T cell activation. The proliferative responses were measured over a 4 day time course of cells cultured in the absence (∇) and in the presence of 100 μg/ml (▼) ErAFP. (●) denotes the background proliferation of the responder cell population cultured separately. ErAFP-mediated suppression on the AMLR over the time course was significant ($p<0.01$).

Figure 3B:
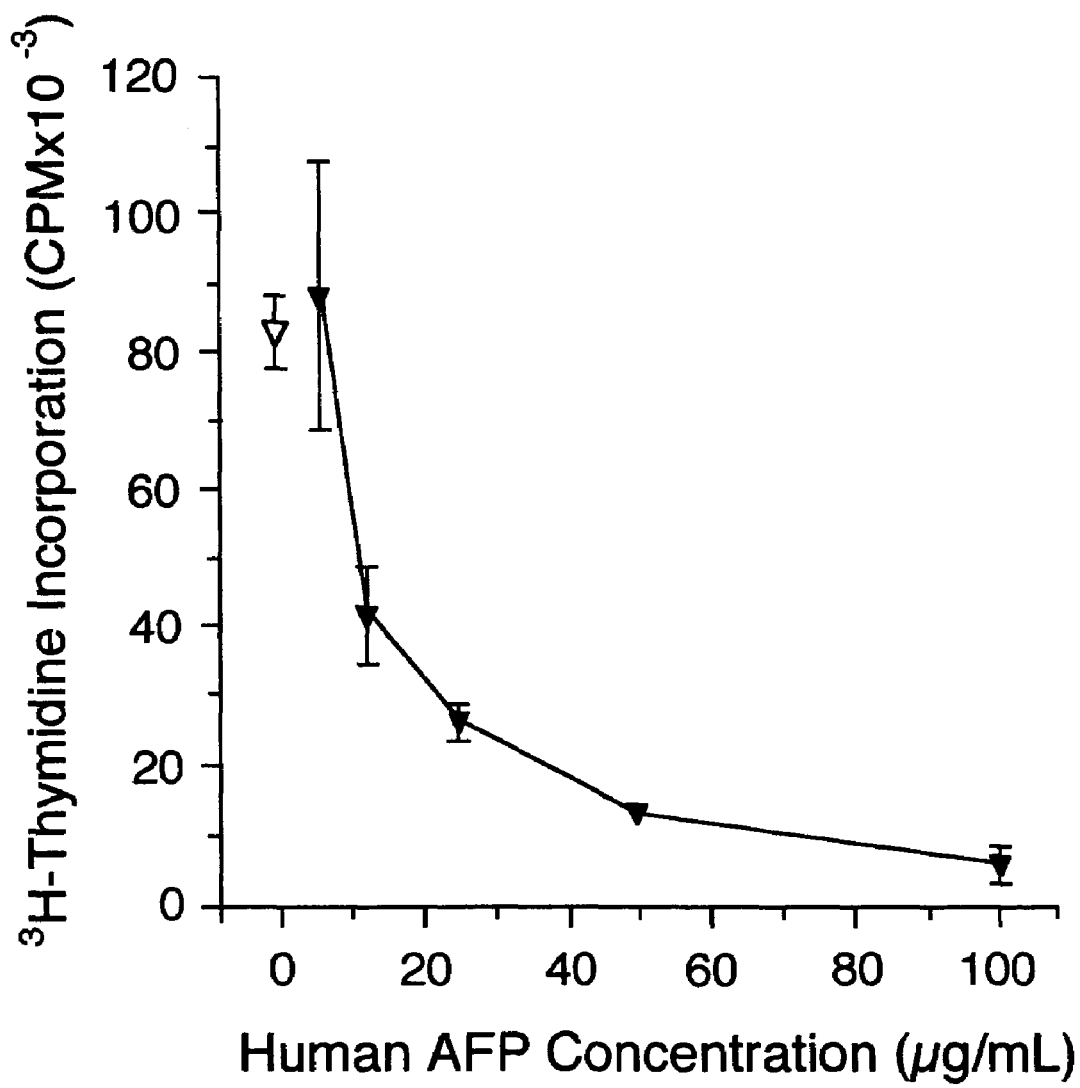

FIG. 3B is a graph showing the dose-response relationship of ErAFP on autoproliferating T cells. The inhibition of autoproliferating T cells was determined at 144 hours with amounts of ErAFP ranging from 6-100 μg/ml (▼). (∇) denotes the control response of the reaction in the absence of protein. Inhibition of autoreactive T cells by ErAFP in the range of 12.5-100 μg/ml is significant ($p<0.005$).

Figure 4:
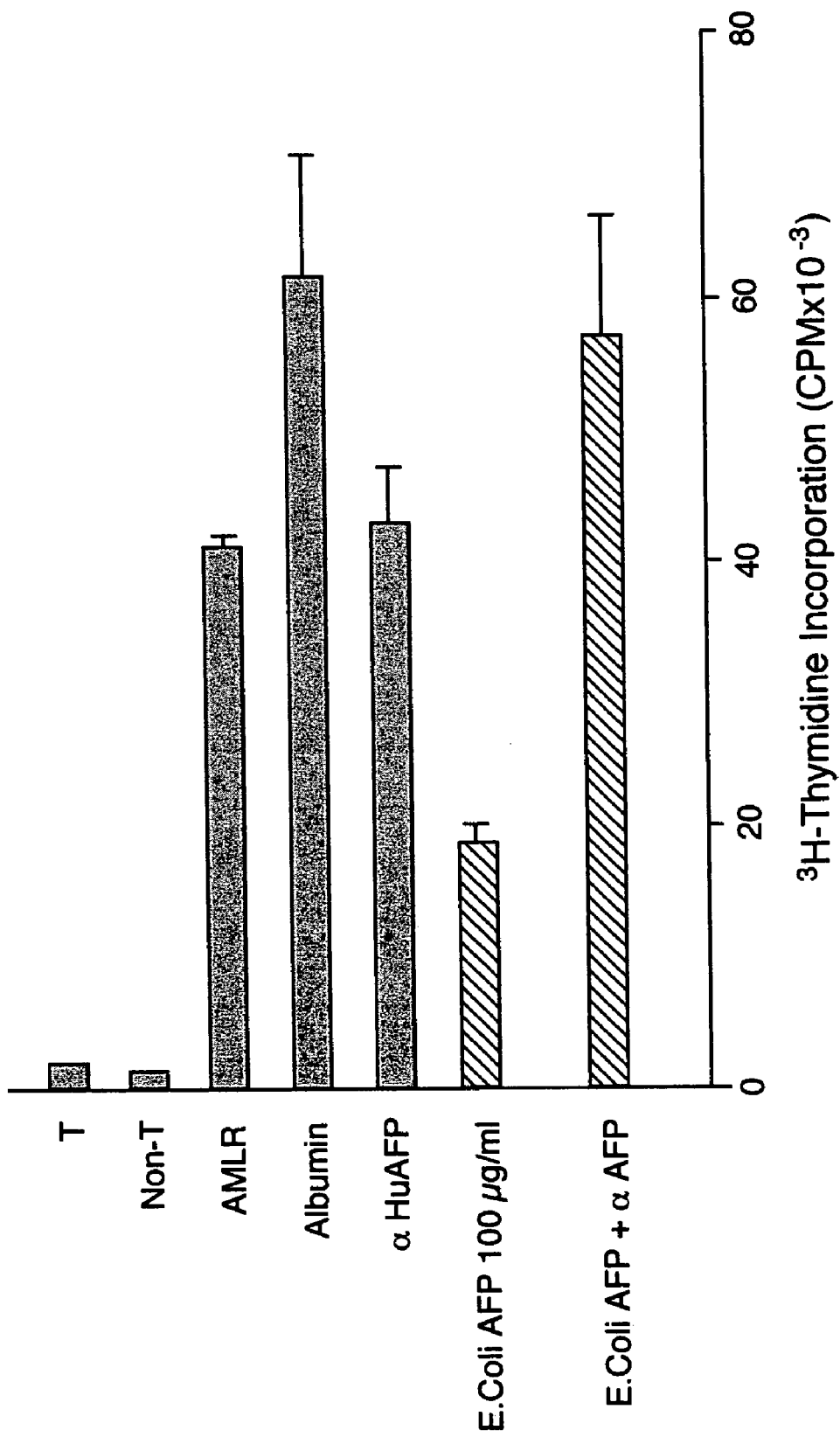

FIG. 4 is a bar graph showing that monoclonal anti-HuAFP antibodies (aAFP) block immunosuppression of the autologous mixed lymphocyte reactions (AMLR) by ErAFP (*E. Coli* AFP). Immunosuppression by ErAFP was significant ($p<0.002$) and blocking of ErAFP-mediated immunosuppression by monoclonal anti-HuAFP antibodies was also significant ($p<0.03$).

FIG. 5 is a chart showing that monoclonal antibodies that recognize HuAFP block immunosuppression of AMLR by BrAFP and ErAFP.

FIG. 6 is a chart showing the immunosuppressive effects of BrAFP, ErAFP, and the AFP fragment of amino acids 1-22 (Δ(1-266)) on mitogen stimulated peripheral blood lymphocytes.

Figure 7A:
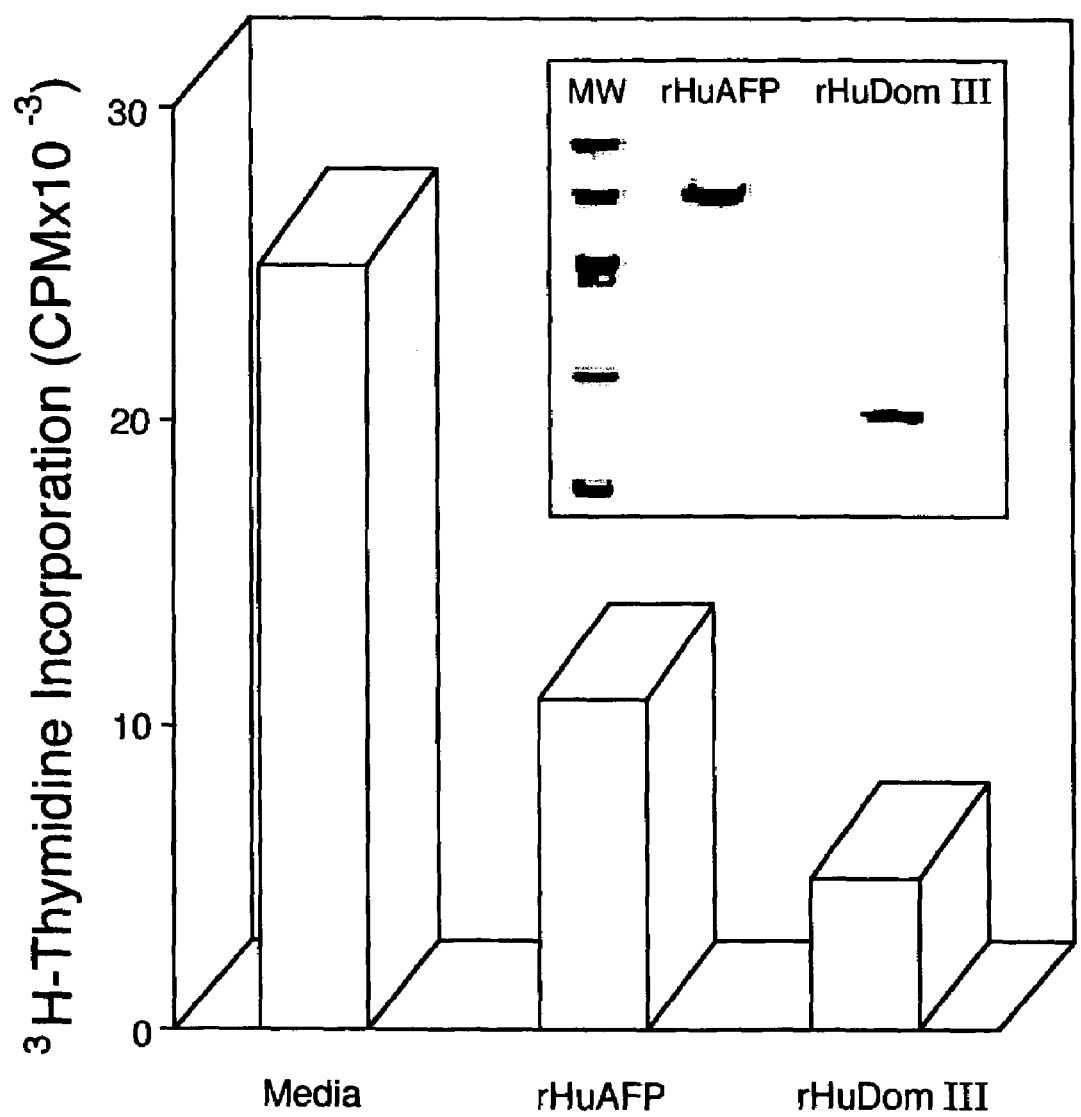

FIG. 7A is a bar graph showing the immunosuppressive effect of human derived full-length HuAFP (HuAFP) versus human domain III AFP (HuDomIII) in AMLR. The gel insert confirms the size of the various recombinant AFP used in the AMLR assays: molecular weight markers (MW), 1 μg HuAFP (lane 1), and 1 μg HuDom III (lane 2).

Figure 7B:
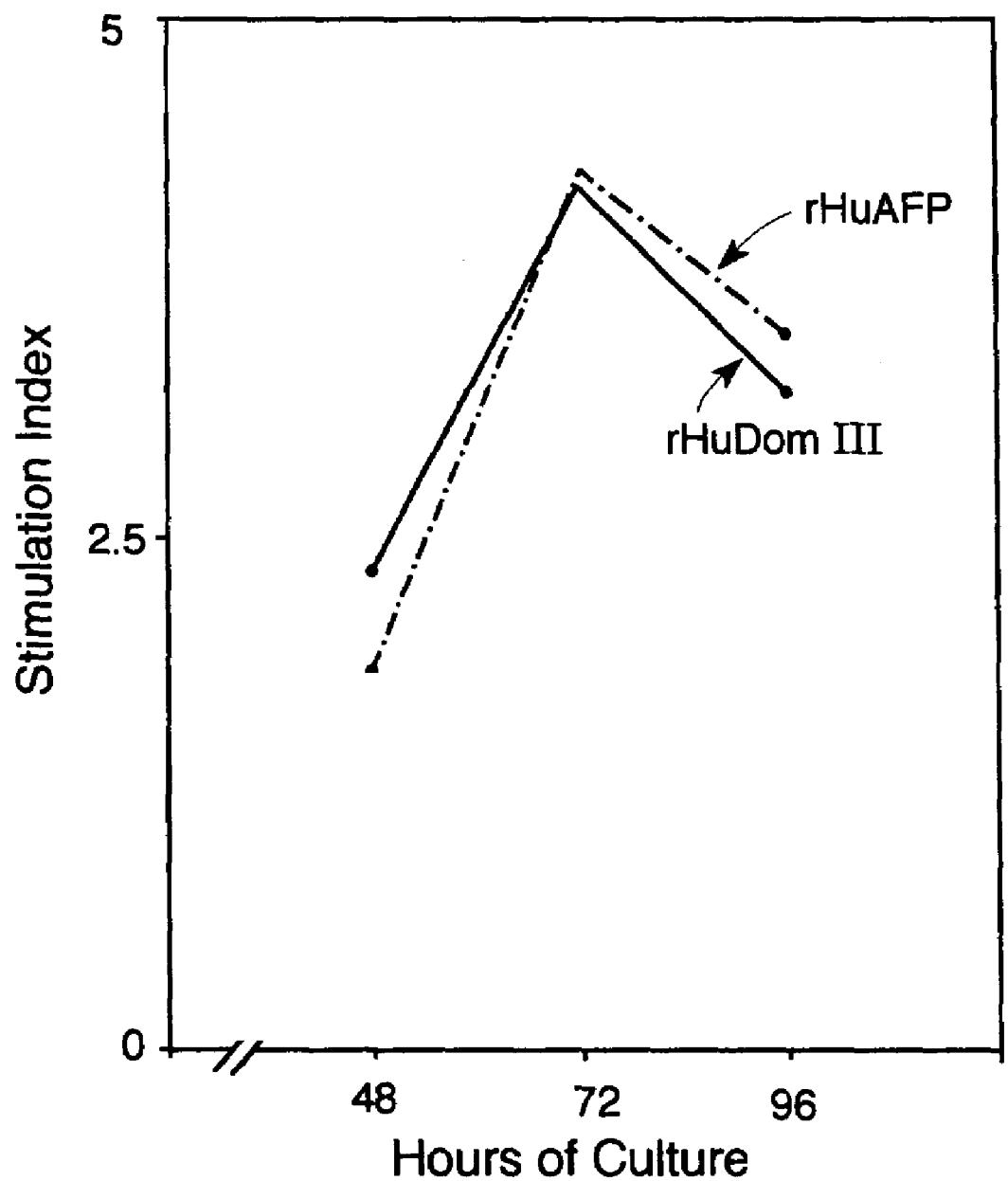

FIG. 7B is a graph showing the time course of HuAFP and HuDom III on immunosuppression of AMLR.

FIG. 8 is a schematic showing the nucleotide sequence (SEQ ID NO: 1) and deduced amino acid sequence (SEQ ID NO: 2) of the cDNA encoding human alpha-fetoprotein.

Figure 9:
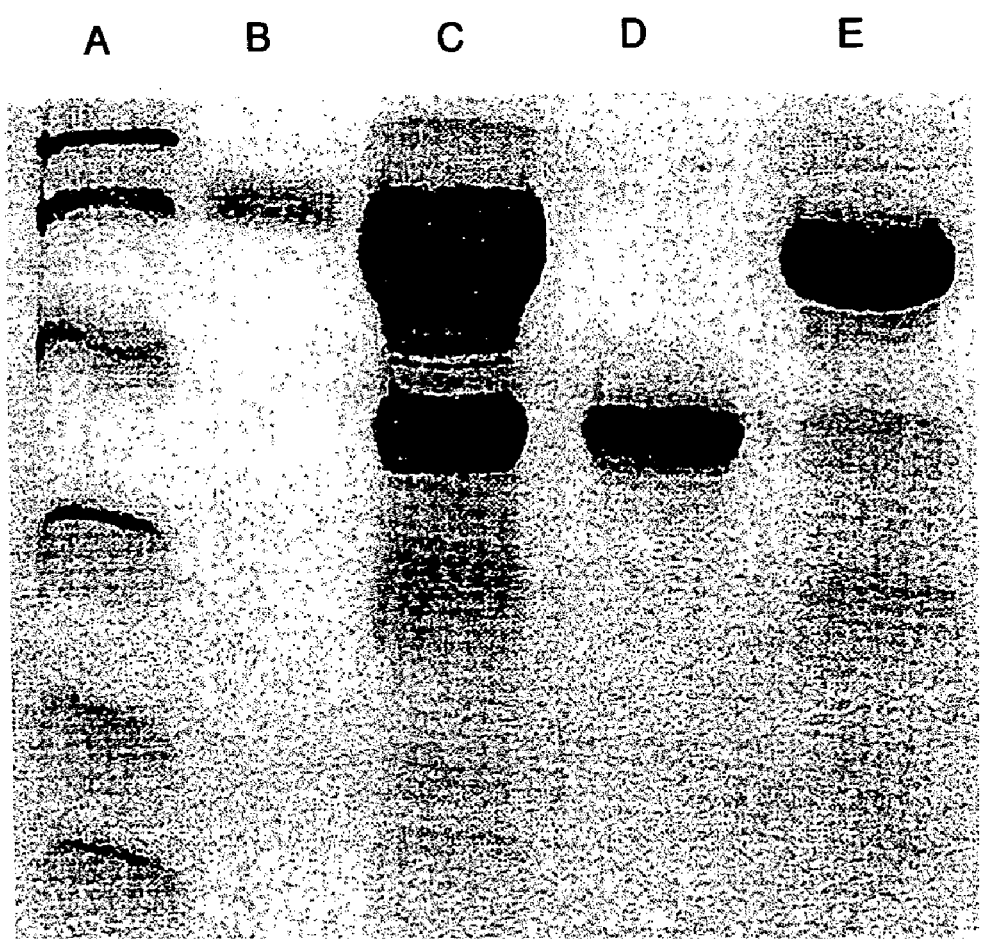

FIG. 9 is an autoradiograph showing the sizes of various AFP and AFP fragments (Lane A, MW marker; Lane B, HuAFP, Lane C, unpurified HuAFP and HuAFP Fragment I, Lane D, purified HuAFP Fragment I, and Lane E, purified full-length HuAFP).

Figure 10A:
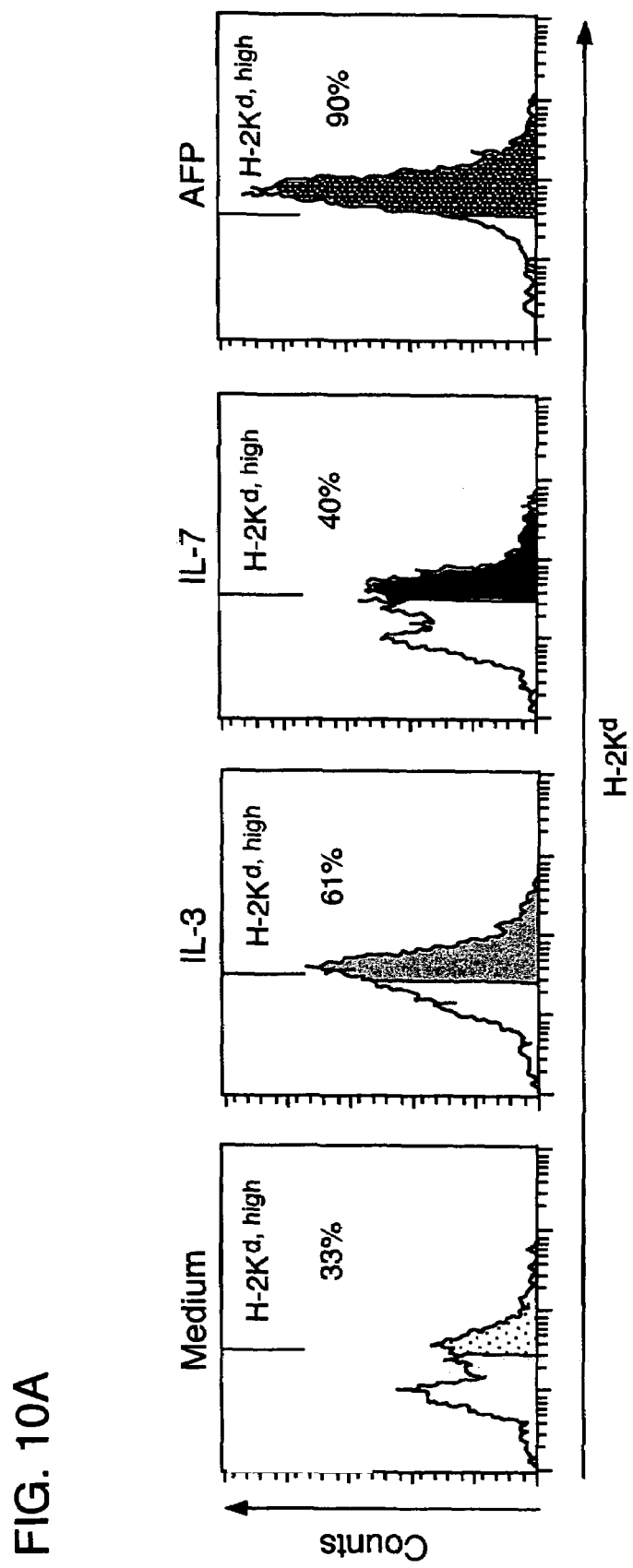

FIG. 10A is a series of histograms showing an increased percentage of bone marrow cells (BM) that express the major histocompatibilty class I protein (MHC I) in presence of rHuAFP.

Figure 10B:
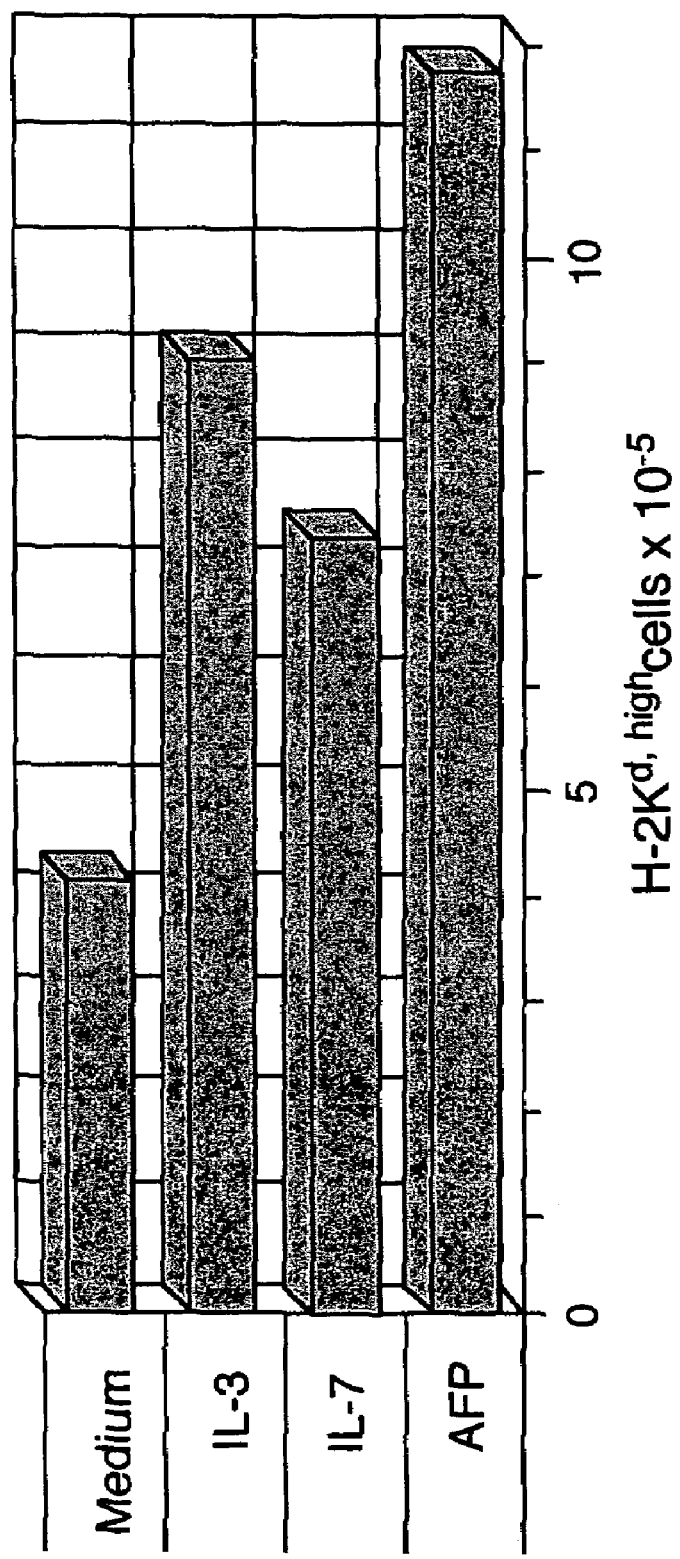

FIG. 10B is a bar graph showing an increased number of BM cells that express MHC I in the presence of rHuAFP.

Figure 11A:
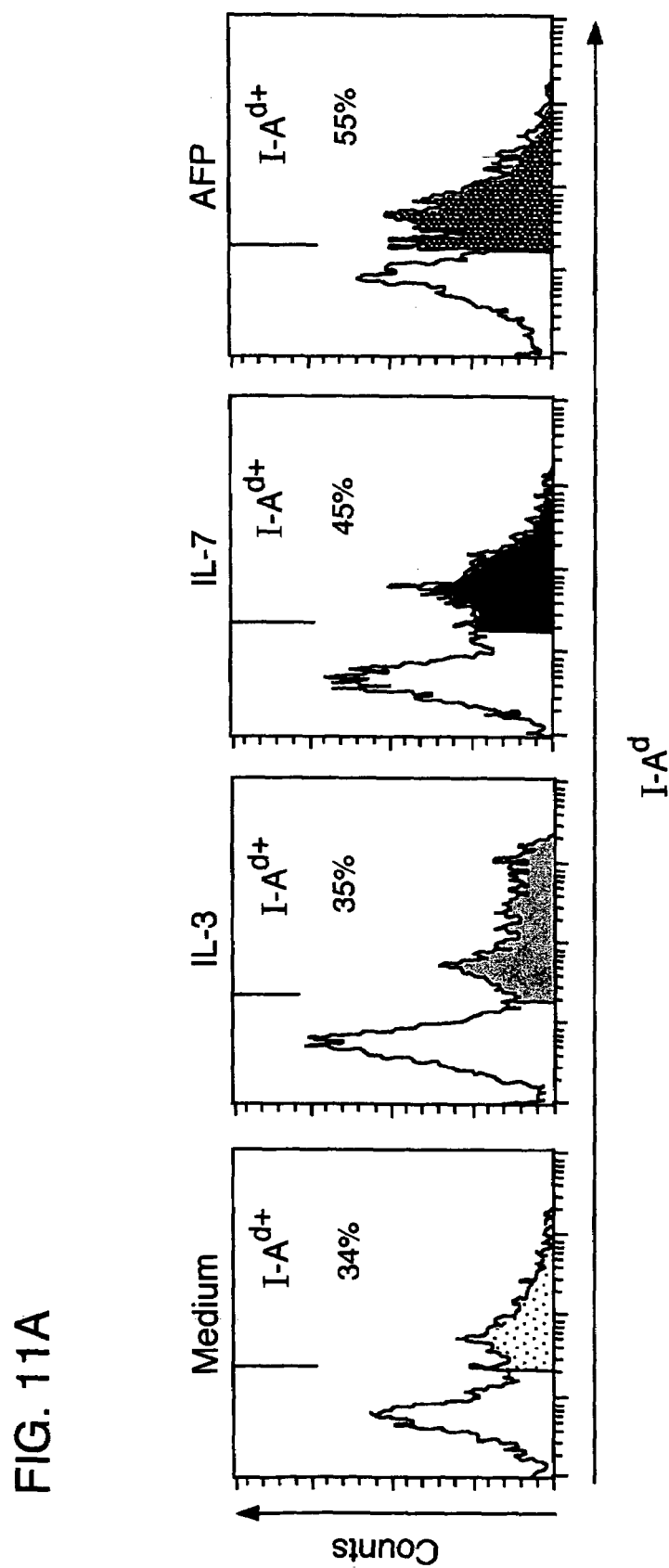

FIG. 11A is a series of histograms showing an increased percentage of BM cells that express the major histocompatibilty class II protein (MHC II) in presence of rHuAFP.

Figure 11B:
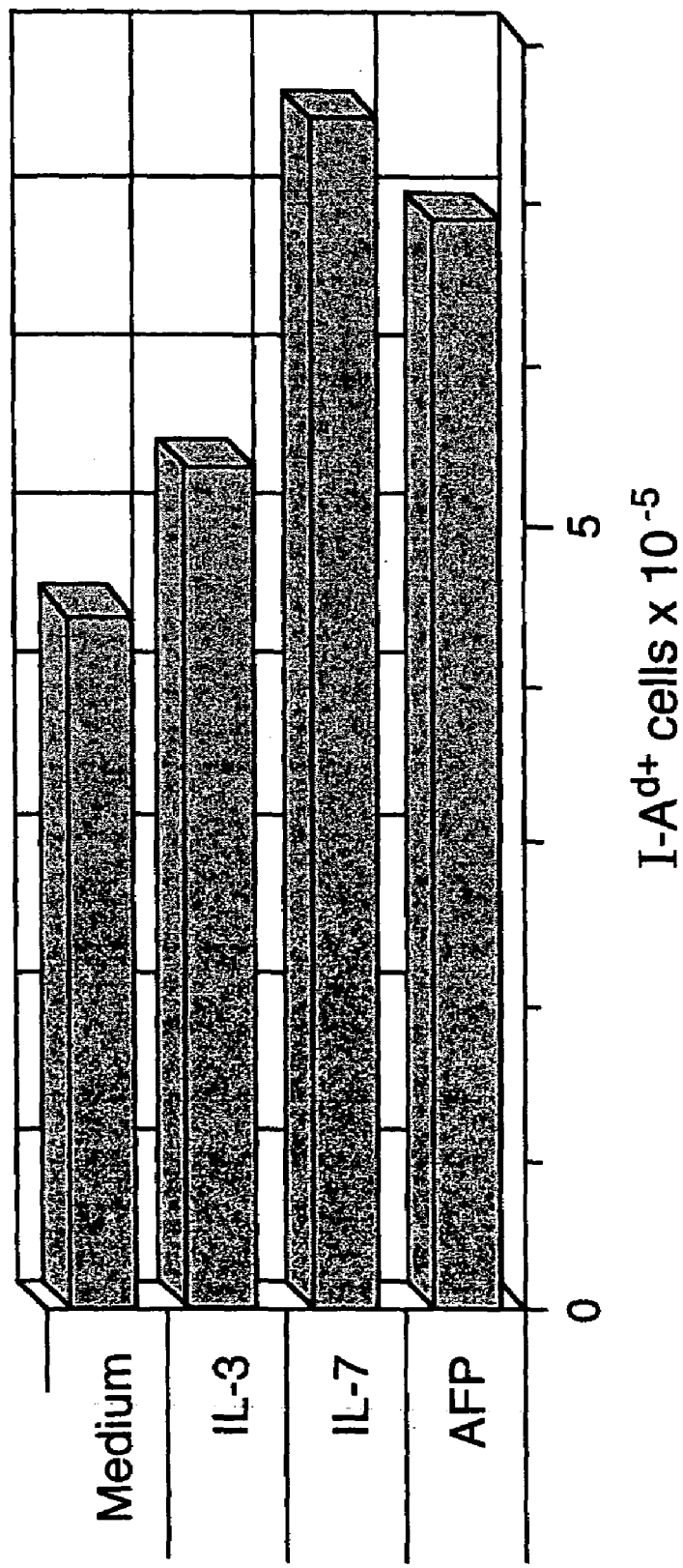

FIG. 11B is a bar graph showing an increased number of BM cells that express MHC II in the presence of rHuAFP.

FIG. 12A is a series of FACS histogram patterns showing increased expression of the MHCI protein H-2$K^K$ and increased expression of the MHCII protein I-2$A^k$ in BM cells cultured in the presence of rHuAFP.

Figure 12B:
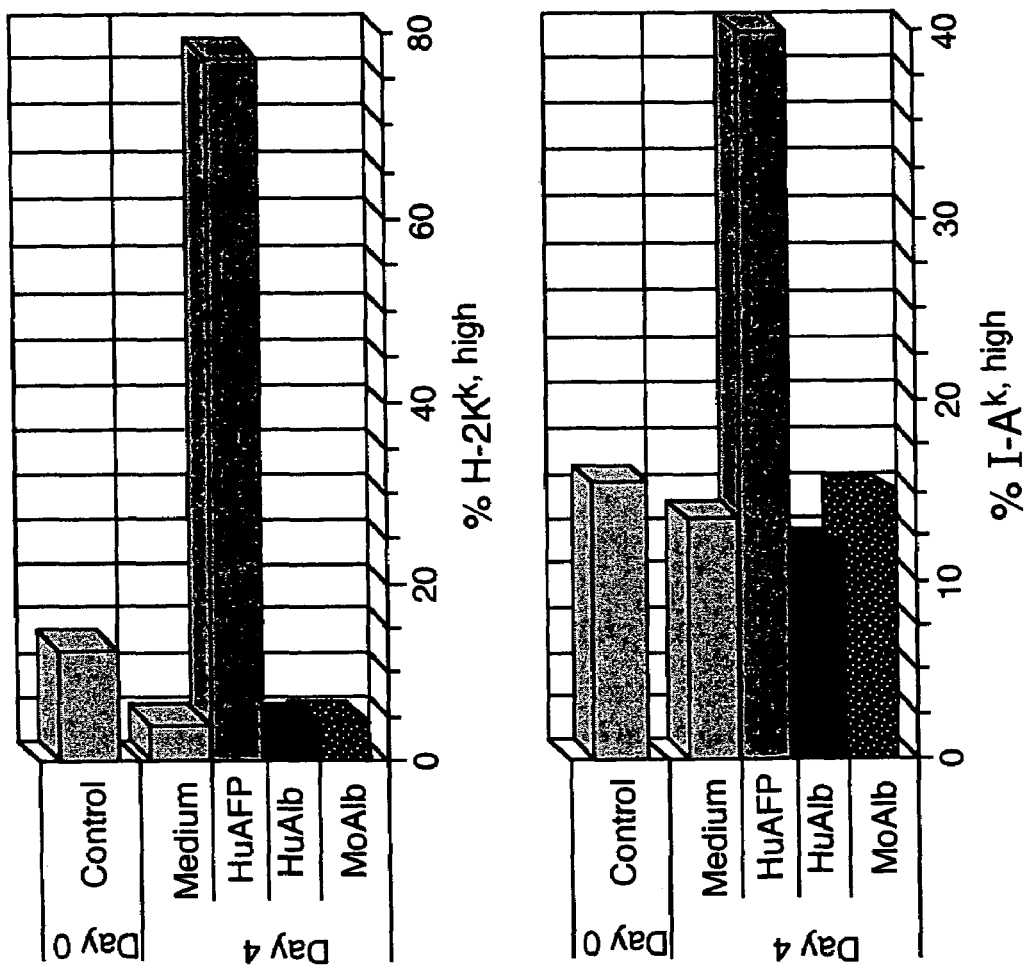

FIG. 12B is a series of bar graphs showing an increase in the percent of BM cells that express H-2$K^{K+}$ and I-2$A^{K+}$ in either medium alone (control), rHuAFP, human albumin (HuAlb), or mouse albumin (MoAlb).

Figure 13:
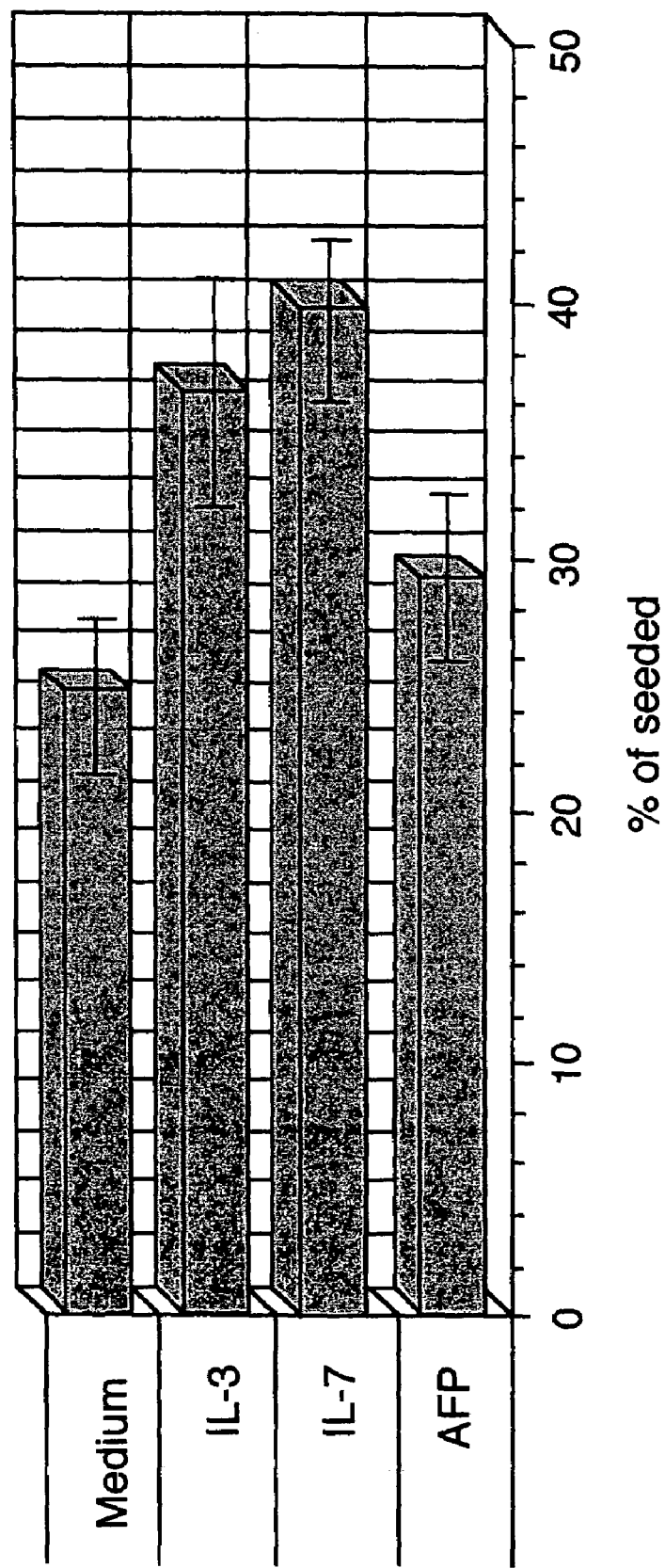

FIG. 13 is a bar graph showing the viability of BM cell cultures treated with 1% FCS in the presence or absence of IL-3, IL-7, or rHuAFP.

Figure 14A:
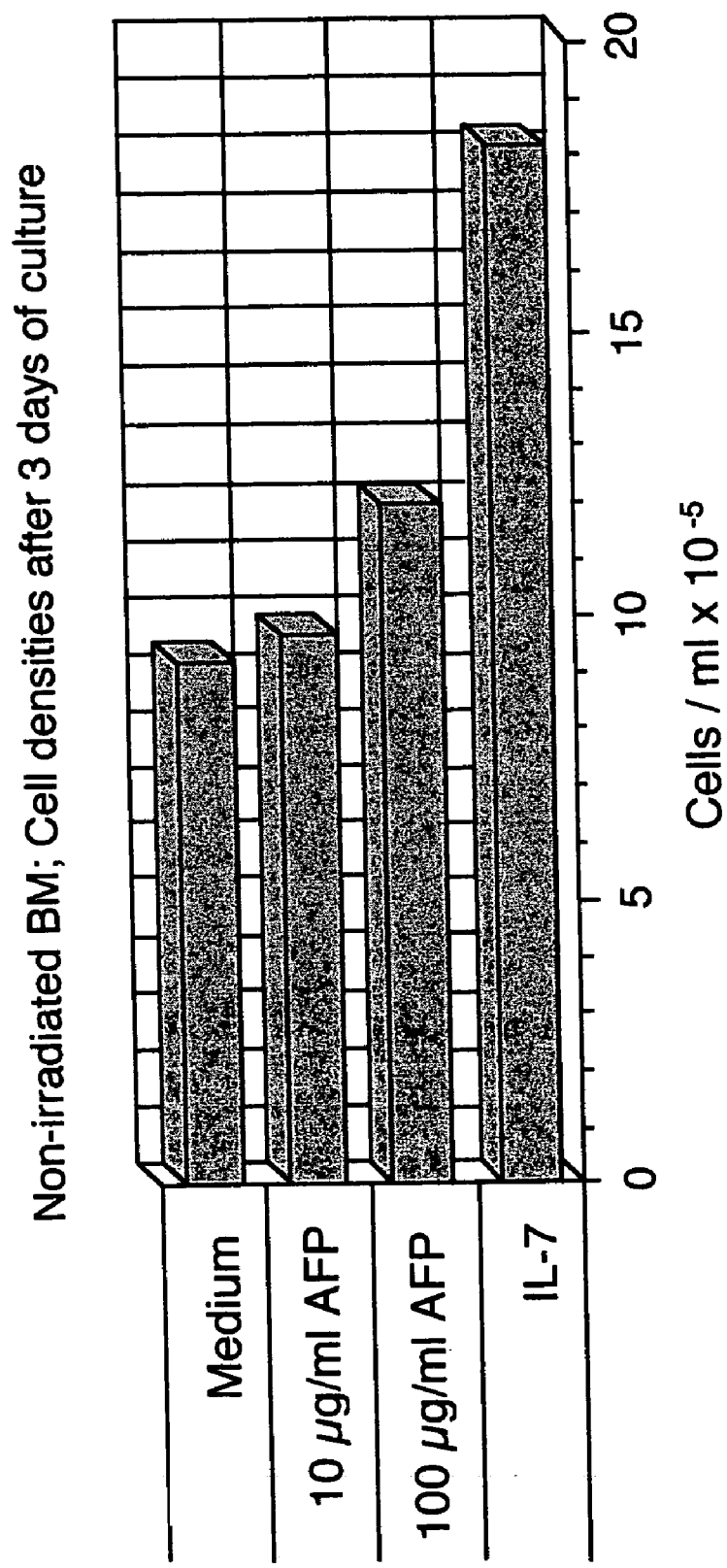

FIG. 14A is a bar graph showing the density of non-irradiated BM cells cultured in the presence of rHuAFP or Il-7.

Figure 14B:
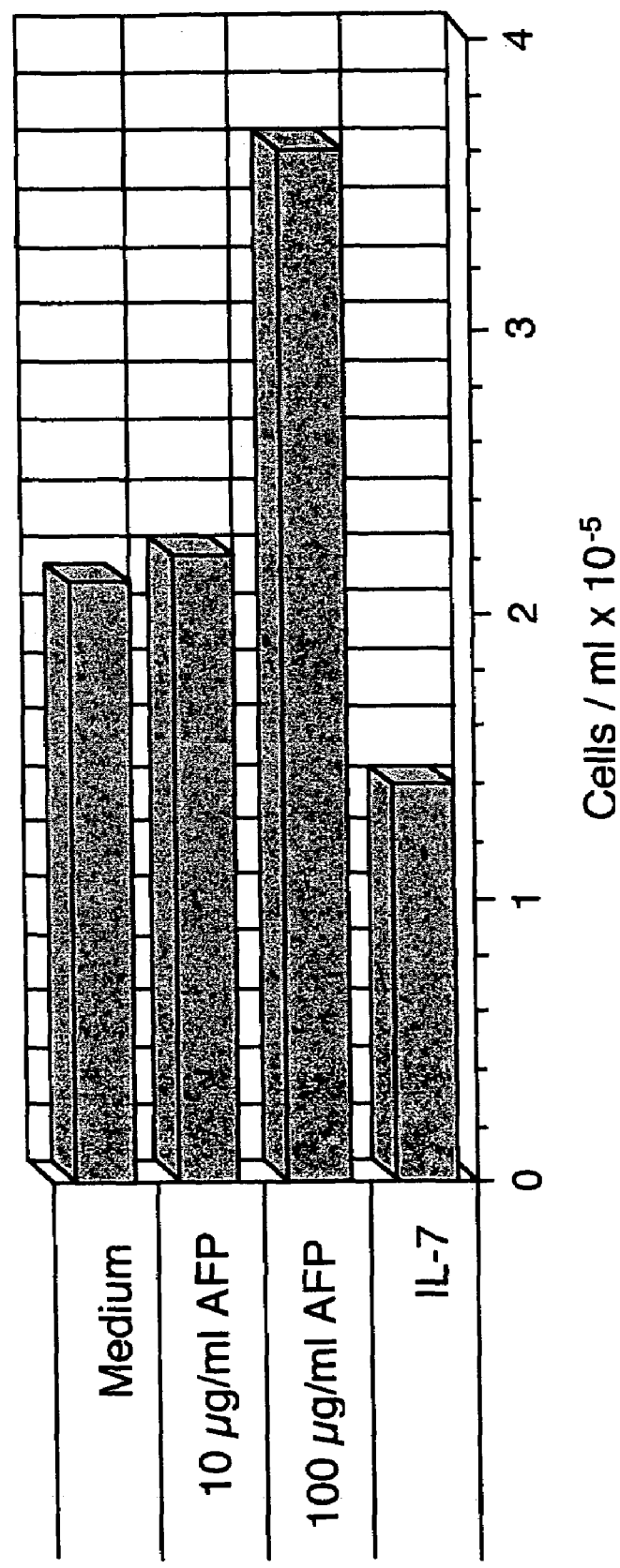

FIG. 14B is a bar graph showing the density of irradiated BM cells cultured in the presence of rHuAFP or Il-7.

FIG. 15A is a series of bar graphs showing enhanced expression of MHCI and, enhanced density of MCHI-expressing BM in the presences of rHuAFP after irradiation.

Figure 15B:
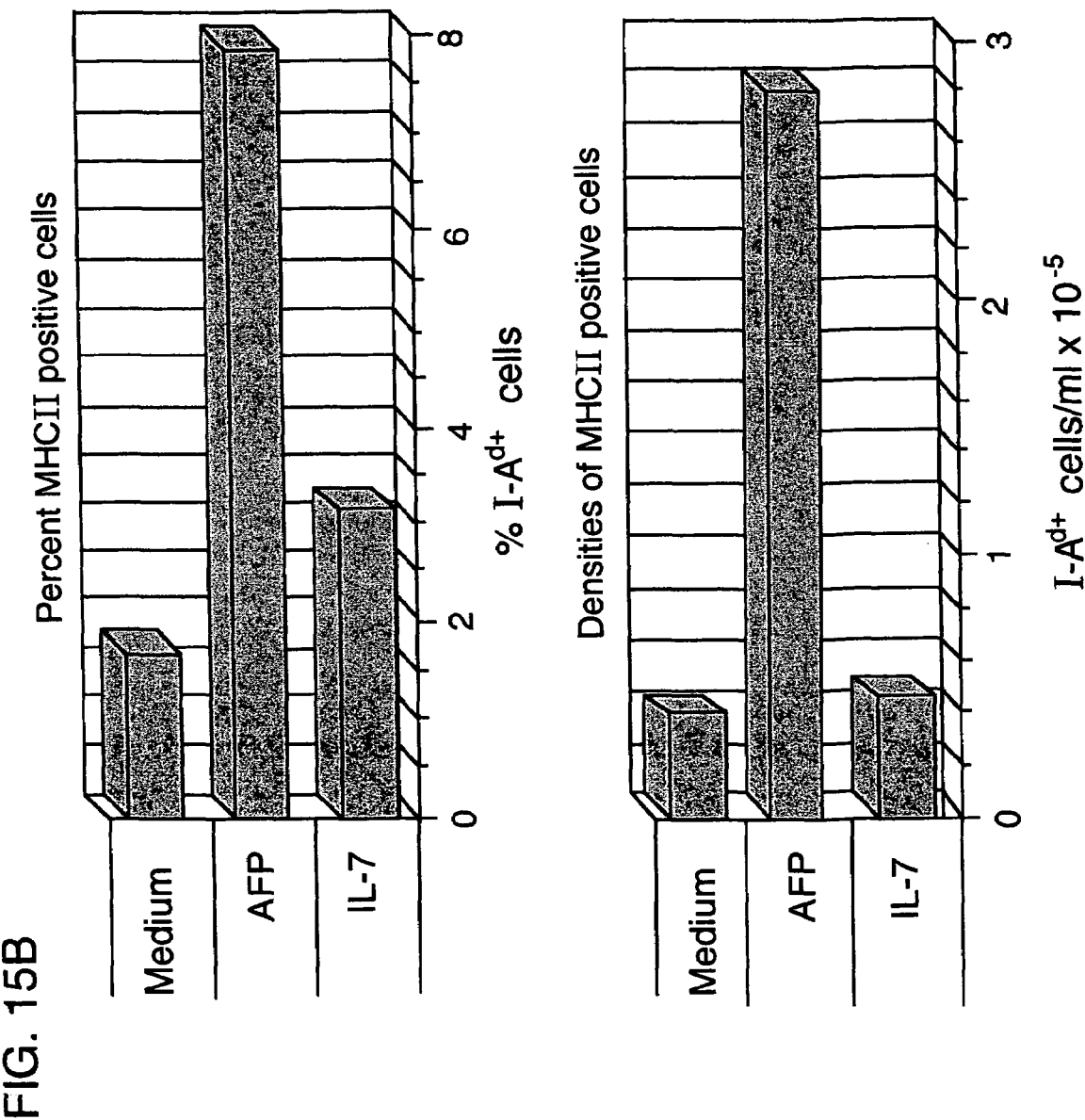

FIG. 15B is a series of bar graphs showing enhanced expression of MHCII and enhanced density of MCHII-expressing BM in the presences of rHuAFP after irradiation.

Production of Recombinant Human Alpha-Fetoprotein

As summarized above, the invention includes therapies for the prevention and treatment of autoimmune diseases involving recombinant human alpha-fetoprotein ("rHuAFP") or fragments or analogs thereof.

Production of Recombinant E. coli Alpha-Fetoprotein

Methods for producing such rHuAFP in a prokaryotic cell are described in U.S. Ser. No. 08/133,773 and in U.S. Pat. No. 5,384,250, issued Jan. 24, 1995, hereby incorporated by reference.

Expression, Purification, and Characterization of Recombinant AFP Produced in Baculovirus (BrAFP)

One eukaryotic expression system that is widely employed for the overexpression of heterologous genes is the baculovirus expression system. There are several advantages to generating recombinant protein in baculovirus infected insect cells, including the ability of this expression system to produce high levels of soluble, secreted, and post-translationally modified proteins (see, O'Reilly, et al. *Baculovirus Expression Vectors. A Laboratory Manual*. W.H. Freeman and Company, New York, 1980). To investigate whether post-translational modifications play a role in mediating AFP immunomodulation, we compared the biological activities of a eukaryotic protein with that produced by a prokaryotic organism. *E. coli* was selected as the prokaryotic host in which to express AFP because it offered advantages such as ease and simplicity in cloning and expressing a heterologous gene (see, Balbas & Bolivar. *Gene Expression Technology*, Goeddel, D. V. ed. New York Academic Press, 1990), simple fusion protein strategies which ensures good translation initiation that may also permit one to overcome the instability problems that can be encountered with small peptides, and rapid generation of biomass due to high rates of cell growth (Id.).

Western blot analysis of serum free supernatants from recombinant baculovirus infected Sf9 cells detected a single immunoreactive band with monospecific anti-HuAFP Ab that was absent from the supernatant of uninfected, or wild-type virus-infected Sf9 cells. Passage of the supernatant containing secreted BrAFP over ConA lectin chromatography resulted in the binding of the recombinant protein and elution in the flow through of more than 90% of the contaminating proteins. Methyl α-D mannopyranoside was used to elute BrAFP from the lectin column. Final purification of the BrAFP preparation was achieved by Mono Q FPLC chromatography, yielding a single polypeptide with an apparent molecular mass of 67 kD (FIG. 2B, lane 3). The BrAFP molecular weight is similar to that observed for the natural human molecule (FIG. 2B, lane 2). This result, in addition to the binding of BrAFP to the ConA column, indicated that BrAFP was post-translationally modified via glycosylation. However, the pattern of glycosylation of the BrAFP is expected to differ from that of the native molecule, since Sf9 cells infected with recombinant baculovirus have been reported to be deficient in their ability to carry out complex glycosylation normally observed with higher eukaryotic derived proteins (O'Reilly, supra; James, et al. *Biotechnology* 13:592-596, 1995). Purity of the isolated BrAFP was verified by APAGE and SDS-PAGE (FIGS. 2A & 2B, lane 2, respectively), and is illustrated by a single symmetrical peal on FPLC and HPLC chromatograms as shown in FIG. 2C, graph 2, and FIG. 2D, graph 2, respectively. N-terminal analysis revealed that the melittin signal peptide was cleaved from the mature recombinant human AFP polypeptide as predicted.

Recombinant AFP expressed in *E. coli* represented approximately 10% of total cell protein as determined by densitometric analysis of Coomassie blue stained SDS-PAGE gels. Alkaline washes of lysed *E. coli* pellets removed major contaminating proteins resulting in a 4-fold enrichment of ErAFP. The recombinant protein was solubilized by dissolving the pellet in a buffer containing guanidine and β-mercaptoethanol, and subsequently refolded by rapid dilution of the denaturant and reducing agent. Monomer BrAFP and ErAFP was efficiently separated from micro aggregates by employing Q-Sparse chromatography. Pure ErAFP was subsequently recovered as a single homogenous peak by FPLC Mono-Q anion exchange chromatography. The final product migrated at 65 kD on SDS-PAGE (FIG. 2B, lane 4). Rechromatographed samples of pure ErAFP on FPLC and HPLC yielded a single peak as shown in FIG. 2C, graph 3 and FIG. 2D, graph 3 respectively, confirming the purity of the BrAFP and ErAFP preparation.

Baculovirus transfer vector pVT-PlacZ was modified by replacing the MCS with the oligonucleotide 5'-GATCTAGAATTCGGATCCGGT-3' (SEQ ID NO: 17) and its complementary fragment, containing EcoR I and BamH I restrictions sites in the 5' to 3' direction. The rHuAFP cDNA fragment was isolated as above, inserted into the vector at the EcoR I and BamH I restriction sties and transformations were verified for the presence and correct orientation of the rHuAFP cDNA fragment under the control of the polyhedrin promoter by using restriction enzyme analysis.

Four mg of transfer vector pVT-PLacZ/HuAFP and 1 mg of linearized wild-type AcMNPV baculovirus DNA (Invitrogen, San Diego, Calif.) were co-transfected in the presence of 50 ml of Lipofectin Reagent (Gibco) into *Spodoptera frigiperda* (Sf9) cells. After 4-6 days of incubation, the transfection mixture was screened by a β-galactosidase assay and DNA slot-blot hybridizations for recombinant viruses containing both the β-galactosidase and rAFP cDNA's. Sf9 cells seeded at a density of $1\times10^6$ cells/ml in 500 ml spinner flasks were infected with BrAFP baculovirus in serum-free Grace medium at a multiplicity of infection of 5. The supernatant was harvested at 72 hours post-infection by pelleting the Sf9 cells at 200×g for 10 minutes and the resultant media was concentrated 10-20 fold by ultrafiltration with a YM30 Amicon filter membrane (Amicon).

Concentrated Grace media containing baculovirus produced AFP was dialyzed against PBS overnight and then applied to a ConA Lectin column (Pharmacia) where all rAFP was bound to the column. Recombinant AFP (BrAFP) was eluted with 0.4M methyl a-D mannopyranoside and this fraction was further purified by recovering protein from a FPLC anion-exchange MonoQ column (Pharmacia) using a linear NaCl gradient from 0-100% 1 M NaCl in 20 mM phosphate buffer pH 8.0. Purified BrAFP protein preparations were dialyzed against 1×PBS and stored at −20° C.

Expression of Alpha-Fetoprotein in Eukaryotes

Recombinant alpha-fetoprotein can be expressed in transgenic animals. Transgenic animals may be prepared using methods well known to the skilled artisan. For example, to prepare transgenic rodents such as mice, methods such as those set forth by Hogan et al., eds. (Manipulating The Mouse Embryo: A Laboratory Manual, Cold Spring Harbor Laboratory Press, Cold Spring Harbor, N.Y. [1986]) may be employed. Additionally, other animals that are suitable for expression of an alpha-fetoprotein transgene include goat, sheep, and cow.

Recombinant apha-fetoprotein transgene expression can be directed to the milk of the transgenic animal. The alpha-fetoprotein transgene is generated in association with a mammary promoter to direct expression of the protein to the animal's milk; is introduced into the pronucleus of a mammalian zygote (usually by microinjection into one of the two nuclei (usually the male nucleus) in the pronucleus); and thereafter implanted into a foster mother. A proportion of the animals produced by the foster mother will carry and express the introduced gene that has integrated into a chromosome. Usually the integrated gene is passed on to offspring by conventional breeding thus allowing ready expansion of stock. Preferably the alpha-fetoprotein is simply harvested from the milk of female transgenic animals. Procedures for directing expression of a gene to the animal's milk are found in the following publications: Simons et al. (1988), Bio/Technology 6:179-183; Wright et al. (1991) Bio/Technology 9:830-834; U.S. Pat. No. 4,873,191 and; U.S. Pat. No. 5,322,775. Manipulation of mouse embryos is described in Hogan et al, "Manipulating the Mouse Embryo; A Laboratory Manual", Cold Spring Harbor Laboratory 1986.

Mammalian cells (for example, CHO, COS, and myeloma cells) can be used as host for the expression of alpha-fetoprotein cDNAs and fragments thereof to produce the corresponding proteins and peptides. For expression of constructs leading to direct expression of active COS or CHO cell expression systems are preferred. The alpha-fetoprotein cDNAs can be introduced to plasmids and allowed to integrate into chromosomal DNA especially for CHO cells or allowed to replicate to very high copy number especially in COS cells. The plasmids generally require a selectable marker for maintenance in transfected hosts, an efficient eukaryotic promoter to allow a high level of transcription from the cDNAs, convenient restriction enzyme sites for cloning and polyadenylation, and transcription termination signals for message stability. Several such vectors have been described in the literature (Bebbington, C. et al, 1992, Bio/Technology, vol 10, p169-175, and Wright, A., 1991, Methods, vol 2, p125-135) and there are commercially available vectors, (such as pRc/CMV, Invitrogen Corp.) which are suitable.

Fragments and Analogs

The invention includes biologically active fragments of AFP from rHuAFP. A biologically active fragment of rHuAFP is one that possesses at least one of the following activities: (a) directs a specific interaction with a target cell, e.g., binds to a cell expressing a receptor which is recognized by rHuAFP (e.g., the membrane of an autoreactive immune cell); or (b) halts, reduces, or inhibits the growth of an autoreactive immune cell (e.g., binds to a cell surface receptor and imparts an anti-proliferative signal); or (c) blocks, inhibits, or prevents an immunopathologic antibody reaction. The ability of rHuAFP fragments or analogs to bind to a receptor which is recognized by rHuAFP can be tested using any standard binding assay known in the art. Methods for assaying the biological activity or rHuAFP fragments and analogs are also known in the art, e.g., those described herein. Accordingly, a rHuAFP fragment, like the full-length rHuAFP molecule, can be used inhibit autoreactive immune cell proliferation.

In general, fragments of rHuAFP are produced according to the techniques of polypeptide expression and purification described in U.S. Ser. No. 08/133,773 (U.S. Pat. No. 5,384,250). For example, suitable fragments of rHuAFP can be produced by transformation of a suitable host bacterial cell with part of a HuAFP-encoding cDNA fragment (e.g., the cDNA described above) in a suitable expression vehicle. Alternatively, such fragments can be generated by standard techniques of PCR and cloned into the expression vectors (supra). Accordingly, once a fragment of rHuAFP is expressed, it may be isolated by various chromatographic and/or immunological methods known in the art. Lysis and fractionation of rHuAFP-containing cells prior to affinity chromatography may be performed by standard methods. Once isolated, the recombinant protein can, if desired, be further purified, e.g., by high performance liquid chromatography (see, e.g., Fisher, *Laboratory Techniques In Biochemistry And Molecular Biology*, Work and Burdon, eds., Elsevier, 1980).

A rHuAFP fragment may also be expressed as a fusion protein with maltose binding protein produced in *E. coli*. Using the maltose binding protein fusion and purification system (New England Biolabs), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from a fragment of the recombinant human cDNA gene product. The cleavage products can be subjected to further chromatography to purify rHuAFP from the maltose binding protein. Alternatively, a fragment of rHuAFP may be expressed as a fusion protein containing a polyhistidine tag can be produced. Such an alpha-fetoprotein fusion protein may then be isolated by binding of the polyhistidine tag to an affinity column having a nickel moiety which binds the polyhistidine region with high affinity. The fusion protein may then be eluted by shifting the pH within the affinity column. The rHuAFP can be released from the polyhistidine sequences present in the resultant fusion protein by cleavage of the fusion protein with specific proteases.

Recombinant HuAFP fragment expression products (e.g., produced by any of the prokaryotic systems described in U.S. Ser. No. 08/133,773 (U.S. Pat. No. 5,384,250)) may be assayed by immunological procedures, such as Western blot, immunoprecipitation analysis of recombinant cell extracts, or immunofluorescence (using, e.g., the methods described in Ausubel et al., *Current Protocols In Molecular Biology*, Greene Publishing Associates and Wiley Interscience (John Wiley & Sons), New York, 1994).

Once a fragment of rHuAFP is expressed, it is isolated using the methods described supra. Once isolated, the fragment of rHuAFP can, if desired, be further purified by using the techniques described supra. Fragments can also be produced by chemical synthesis (e.g., by the methods described in *Solid Phase Peptide Synthesis,* 2nd ed., 1984, The Pierce Chemical Co., Rockford, Ill.). The ability of a candidate rHuAFP fragment to exhibit a biological activity of alpha-fetoprotein is assessed by methods known to those skilled in the art (e.g., those described herein).

The purified recombinant gene product or fragment thereof can then be used to raise polyclonal or monoclonal antibodies against the human recombinant alpha-fetoprotein using well-known methods (see Coligan et al., eds., *Current Protocols in Immunology,* 1992, Greene Publishing Associates and Wiley-Interscience). To generate monoclonal antibodies, a mouse can be immunized with the recombinant protein, and antibody-secreting B cells isolated and immortalized with a nonsecretory myeloma cell fusion partner. Hybridomas are then screened for production of recombinant human alpha-fetoprotein (or a fragment or analog thereof)-specific antibodies and cloned to obtain a homogenous cell population that produces monoclonal antibodies.

As used herein, the term "fragment," as applied to a rHuAFP polypeptide, is preferably at least 20 contiguous amino acids, preferably at least 50 contiguous amino acids, more preferably at least 100 contiguous amino acids, and most preferably at least 200 to 400 or more contiguous amino acids in length. Fragments of rHuAFP molecules can be generated by methods known to those skilled in the art, e.g., proteolytic cleavage or expression of recombinant peptides, or may result from normal protein processing (e.g., removal of amino acids from nascent polypeptide that are not required for biological activity).

Recombinant HuAFP fragments of interest include, but are not limited to, Domain I (amino acids 1 (Thr)-197 (Ser), see FIG. 4, SEQ ID NO: 3), Domain II (amino acids 198 (Ser)-389 (Ser), see FIG. 4, SEQ ID NO: 4), Domain III (amino acids 390 (Gln)-590 (Val), see FIG. 4, SEQ ID NO: 5), Domain I+II (amino acids 1 (Thr)-389 (Ser), see FIG. 4, SEQ ID NO: 6), Domain II+III (amino acids 198 (Ser)-590 (Val), see FIG. 4, SEQ ID NO: 7), and rHuAFP Fragment I (amino acids 266 (Met) -590 (Val), see FIG. 4, SEQ ID NO: 8). Activity of a fragment is evaluated experimentally using conventional techniques and assays, e.g., the assays described herein.

The invention further includes analogs of full-length rHuAFP or fragments thereof. Analogs can differ from rHuAFP by amino acid sequence differences, or by modifications (e.g., post-translational modifications), which do not affect sequence, or by both. Analogs of the invention will generally exhibit at least 80%, more preferably 85%, and most preferably 90% or even 99% amino acid identity with all or part of a rHuAFP amino acid sequence. Modifications (which do not normally alter primary sequence) include in vivo, or in vitro chemical derivatization of polypeptides, e.g., acetylation, or carboxylation; such modifications may occur during polypeptide synthesis or processing or following treatment with isolated modifying enzymes. Analogs can also differ from the naturally occurring rHuAFP by alterations in primary sequence, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. These include genetic variants, both natural and induced (for example, resulting from random mutagenesis by irradiation or exposure to ethanemethylsulfate or by site-specific mutagenesis as described in Sambrook et al., *Molecular Cloning: A Laboratory Manual*, 2nd ed., Cold Spring Harbor Press, 1989, or Ausubel et al., supra)). Also included are cyclized peptide molecules and analogs which contain residues other than L-amino acids, e.g., D-amino acids or non-naturally occurring or synthetic amino acids, e.g., β or γ amino acids, or L-amino acids with non-natural side chains (see e.g., Noren et al., *Science* 244:182, 1989). Methods for site-specific incorporation of non-natural amino acids into the protein backbone of proteins is described, e.g., in Ellman et al., *Science* 255:197, 1992. Also included are chemically synthesized polypeptides or peptides with modified peptide bonds (e.g., non-peptide bonds as described in U.S. Pat. No. 4,897,445 and U.S. Pat. No. 5,059,653) or modified side chains to obtain the desired pharmaceutical properties as described herein. Useful mutants and analogs are identified using conventional methods, e.g., those described herein.

The cloning, expression, isolation and characterization of exemplary rHuAFP fragments now follows.

These examples are provided to illustrate, not limit, the invention.

EXPERIMENTAL

MATERIALS AND METHODS

Polymerase Chain Reaction (PCR) rHuAFP Fragments

Plasmid constructs encoding fragments of human alpha-fetoprotein were prepared using polymerase chain reaction (PCR) techniques known to those skilled in the art of molecular biology, using oligonucleotide primers designed to amplify specific portions of the human alpha-fetoprotein gene (see e.g., *PCR Technology*, H. A. Erlich, ed., Stockton Press, New York, 1989; *PCR Protocols: A Guide to Methods and Applications*, M. A. Innis, David H. Gelfand, John J. Sninsky, and Thomas J. White, eds., Academic Press, Inc., New York, 1990, and Ausubel et. al., supra).

The following six rHuAFP fragments were prepared to evaluate their biological activity (e.g., according to the methods disclosed herein):

Domain I Amino acids 1 (Thr)-197 (Ser), (FIG. 4, SEQ ID NO: 3)

Domain II Amino acids 198 (Ser)-389 (Ser), (FIG. 4, SEQ ID NO: 4)

Domain III Amino acids 390 (Gin)-590 (Val), (FIG. 4, SEQ ID NO: 5)

Domain I+II Amino acids I (Thr)-389 (Ser), (FIG. 4, SEQ ID NO: 6)

Domain II+III Amino acids 198 (Ser)-590 (Val), (FIG. 4, SEQ ID NO: 7).

rHuAFP Fragment I Amino acids 266 (Met)-590 (Val), (FIG. 4, SEQ ID NO: 8)

Amino acid sequences were deduced from those for human alpha-fetoprotein (1 (Thr)-590 (Val); SEQ ID NO: 2) shown in FIG. 4. Fragments of rHuAFP designated Domain I, Domain II, Domain III, Domain I+II, Domain II+III and rHuAFP Fragment I were synthesized using standard PCR reaction conditions in 100 μL reactions containing 34 μL H$_2$O, 10 μL 10× reaction buffer, 20 μL 1 mM dNTP, 2 μL DNA template (HuAFP cloned in pI18), appropriate 5' and 3' oligonucleotide primers. (110 L 10 pmol/μL 5' primer, 10 μL 10 pmol/μL 3' primer), 1 μL glycerol, 10 μL DMSO, and 1 μL Pfu polymerase (Stratagene, LaJolla, Calif.). Primers used for PCR amplifications were:

```
                                          (SEQ ID NO: 9)
DomI25
5'-AAAAAAGGTACCACACTGCATAGAAATGAA-3'

(SEQ ID NO: 10)
DomI3
5'-AAAAAAGGATCCTTAGCTTTCTCTTAATTCTTT-3'

(SEQ ID NO: 11)
DomII5
5-'AAAAAAATCGATATGAGCTTGTTAAATCAACAT-3'

(SEQ ID NO: 12)
DomII3
5'-AAAAAAGGATCCTTAGCTCTCCTGGATGTATTT-3'

(SEQ ID NO: 13)
DomIII5
5'-AAAAAAATCGATATGCAAGCATTGGCAAAGCGA-3'

(SEQ ID NO: 14)
DomIII3
5'-AAAAAAGGATCCTTAAACTCCCAAAGCAGCACG-3'
```

-continued (SEQ ID NO: 15)
5'rHuAFP Fragment I
5'-AAAAAAATCGATATGTCCTACATATGTTCTCAA-3'

Accordingly, primer pairs DomI25 and DomI3, DomI5 and DomII3, DomII5 and DomIII3, 5'rHuAFP Fragment I and DomIII3, DomI25 and DomII3, and DomII5 and DomIII3 were used to isolate cDNA sequences of Domain I, Domain II, Domain III, rHuAFP Fragment I, Domain I+II, and Domain II+III, respectively, of rHuAFP. Annealing, extension, and denaturation temperatures were 50° C., 72° C., and 94° C., respectively, for 30 cycles. PCR products were purified according to standard methods. Purified PCR products encoding Domain I and Domain I+II were digested individually with KpnI and BamHI and cloned separately into KpnI/BamHI-treated pTrp4. Purified PCR products encoding Domain II, Domain III, Domain II+III, and rHuAFP Fragment I were digested individually with Bsp 1061 and BamHI and were cloned separately into Bsp106I/BamHI-treated pTrp4. Each plasmid construct was subsequently transformed into competent E. coli cells. Since the expression product will begin with the amino acid sequence encoded by the translation start signal methionine, it is expected that such signal will be removed, or in any event, not affect the bioactivity of the ultimate expression product.

Autologous Mixed Lymphocyte Reactions (AMLR)

AMLR assays were performed as described below.

RESULTS

Expression and Purification

E. coli containing the expression plasmid encoding rHuAFP Fragment I was cultured and purified. FIG. 9 (lane D) shows the SDS-PAGE profile of the purified rHuAFP Fragment I. N-terminal amino acid sequence analysis showed that rHuAFP Fragment I possessed the amino acid sequence Ser267-Tyr-Ile-Cys-Ser-Gln-Gln-Asp-Thr$_{275}$ (SEQ ID NO: 16) which corresponds to the expected N-terminal amino acid sequence of rHuAFP Fragment I (see FIG. 8, SEQ ID NO: 2) where the initiating methionine is cleaved intracellularly.

Inhibition of the Autologous Mixed Lymphocyte Reactions (AMLR)

The immunosuppressive activity of 100 µg/ml rHuAFP Fragment I was assessed by its ability to suppress human autologous mixed lymphocyte reactions (AMLR). As shown in Table I, rHuAFP Fragment I inhibited the proliferative response of autoreactive lymphocytes stimulated by autologous non-T cells at 144 hours.

TABLE I

| Reaction Setup | Thymidine Incorporation (CPM) |
| --- | --- |
| T Cells | 7118 ± 964 |
| AMLR | 83103 ± 6480 |
| AMLR + rHuAFP Fragment I (100 µg/ml) | 29692 ± 2963 |

Recombinant HuAFP as an Immunosuppressive Agent

Immunosuppressive attributes of rHuAFP (or a fragment or analog thereof) were evaluated by any standard assay for analysis of immunoregulatory activity in vivo or in vitro. As discussed infra, the art provides a number of animal systems for in vivo testing of immunosuppressive characteristics of rHuAFP (or a fragment or analog thereof) on an autoimmune disease, e.g., the nonobese diabetic (NOD) mouse. Furthermore, a wide variety of in vitro systems are also available for testing immunosuppressive aspects of rHuAFP e.g., one such in vitro assay evaluates the inhibition of autoantigen-induced proliferation of T cells in an autologous mixed lymphocyte reaction (AMLR).

The following examples demonstrate that unglycosylated rHuAFP inhibits T cell autoproliferation in response to self antigens. These examples are provided to illustrate, not limit, the invention.

EXPERIMENTAL

MATERIALS AND METHODS

Gel Electrophoresis, Immunoblotting and Purification

The purity and characterization of rHuAFP was evaluated by sodium dodecyl sulfate-polyacrylamide gel electrophoresis (SDS-PAGE) and nondenaturing alkaline PAGE (APAGE) according to standard methods. Gels were subsequently analyzed either by staining with Coomassie brilliant blue or by transferring electrophoretically separated polypeptides to Immobilon PVDF membranes (Millipore, Mississauga, ON) for immunoblotting analysis. Recombinant HuAFP-monospecific rabbit anti-natural HuAFP polyclonal antibody complexes were identified by alkaline-phosphatase-conjugated goat anti-rabbit IgG and the immunoreactive bands were detected with the BCIP/NBT color development solution (Bio-Rad Laboratories, Mississauga, ON) according to the manufacturer's instructions.

Column chromatography was performed according to standard methods.

Cell Preparation

Human peripheral blood mononuclear cells (PBMC) were isolated from heparin-treated whole blood of normal adult donors by venipuncture. Blood was diluted 1:1 with PBS, layered on Ficoll-Hypaque (Sigma, St. Louis, Mo.) and centrifuged at 400×g for 30 min at 25° C. Cells were removed from the interface, washed 3 times in PBS and examined under microscope for viability using the Trypan Blue exclusion method. Cell preparations which were less than 95% viable were discarded. At this stage, the cell preparations were ready to be cultured for the Con A mitogen assay. For the autologous mixed lymphocyte reaction (AMLR), PBMC were fractionated into T cell and non T cell populations. Responder T cells for the AMLR were prepared by passing 1.5×10$^8$ PBMC over a commercial Ig-anti-Ig affinity column (Biotex Laboratories, Edmonton, AB), washing 3 times in PBS, and resuspending them in RPMI-1640 medium. The separation of non-T from T cell populations in PBMC was based on the capacity of T cells to form E-rossettes with sheep red blood cells (SBRC) (Mendas, et al. *J. Immunol.* 111:860-867, 1973). One ml of pelleted SRBC was treated with 1 U of neuramimidase (Sigma) for 1 hour at 37° C., washed 3 times, and resuspended in 50 ml of RPMI media to yield a 2%, SRBC solution. This procedure enhanced cellular interactions between T-cells and SRBC. PBMC (5-9×10$^7$) were then incubated in a ratio of 1×10$^7$ PBMC:2 ml SRBC solution: 2 ml heat inactivated FCS at 37° C. for 10 min. This was followed by 5 min of centrifugation at 200×g prior to a second incubation for 60 min at 4° C. The cell mixtures were then gently resuspended and the rossetted T cells separated from the non-T cells by density centrifugation on Ficoll-Hypaque for 30 min at 400×g. The non-T cells were collected from the interface, washed three times and resuspended in RPMI-1640 media.

Autologous Mixed Lymphocyte Reaction (AMLR)

Isolation of human PBMC, their fractionation into non-T cell populations, and the AMLR, were performed according by the standard procedure described above. Responder T cells were isolated by passing $1.5 \times 10^8$ PMBC over a commercial Ig-anti-Ig affinity column (Biotek Laboratories) and $2 \times 10^5$ responder cells were subsequently cultured with $2 \times 10^5$ autologous $^{137}$Cs-irradiated (2500 rads) non-T stimulator cells from a single donor. The medium employed consisted of RPMI-1640 supplemented with 20 mM HEPES (Gibco), $5 \times 10^{-5}$ M 2-mercaptoethanol (BDH, Montreal, QC), 4 mM L-glutamine (Gibco), 100 U/ml penicillin (Gibco) and 100 µg/ml streptomycin sulfate, with the addition of 10% fresh human serum autologous to the responder T cell donor for the AMLR. Varying concentrations of purified rHuAFP, human serum albumin (HSA), anti-HuAFP monoclonal antibodies clone #164 (125 µg/ml final concentration in culture) (Leinco Technologies, St. Louis, Mo.) were added at the initiation of cultures. AMLR cultures were incubated for 4 to 7 days, at 37° C. in 95% air and 5% $CO_2$. At the indicated intervals, DNA synthesis was assayed by a 6 hour pulse with 1 µCi of $^3$H-thymidine (specific activity 56 to 80 Ci/mmole, ICN). The cultures were harvested on a multiple sample harvester (Skatron, Sterling, Va.), and the incorporation of $^3$H-TdR was measured in a Packard 2500 TR liquid scintillation counter. Results are expressed as mean cpm±the standard error of the mean of triplicate or quadruplicate cultures.

Mitogen-Stimulated Lymphocyte Assays

Mitogen cultures consisted of $2.5 \times 10^5$ PBMC stimulated with 1 µg/ml of Con A (Pharmacia). The media employed consisted of RPMI-1640 supplemented with 20 mM HEPES (Gibco), $5 \times 10^{-5}$ M 2-mercaptoethanol (BDH, Montreal, QC), 4 mM L-glutamine (Gibco), 100 U/ml penicillin (Gibco) and 100 mg/ml streptomycin sulfate and 2 mg/ml of low endotoxin human serum albumin (HSA) (ICN Biomedials Canada, Mississauga, ON). Purified rAFP from both recombinant sources were added to the cultures at a concentration of 100 µg/ml. Mitogen reactions were cultured for 48 hours at 37° C. in 95% air and 5% $CO_2$ and assayed for proliferative responses as described for the AMLR.

RESULTS

Expression and Purification of Human Alpha-Fetoprotein

Figure 1A:
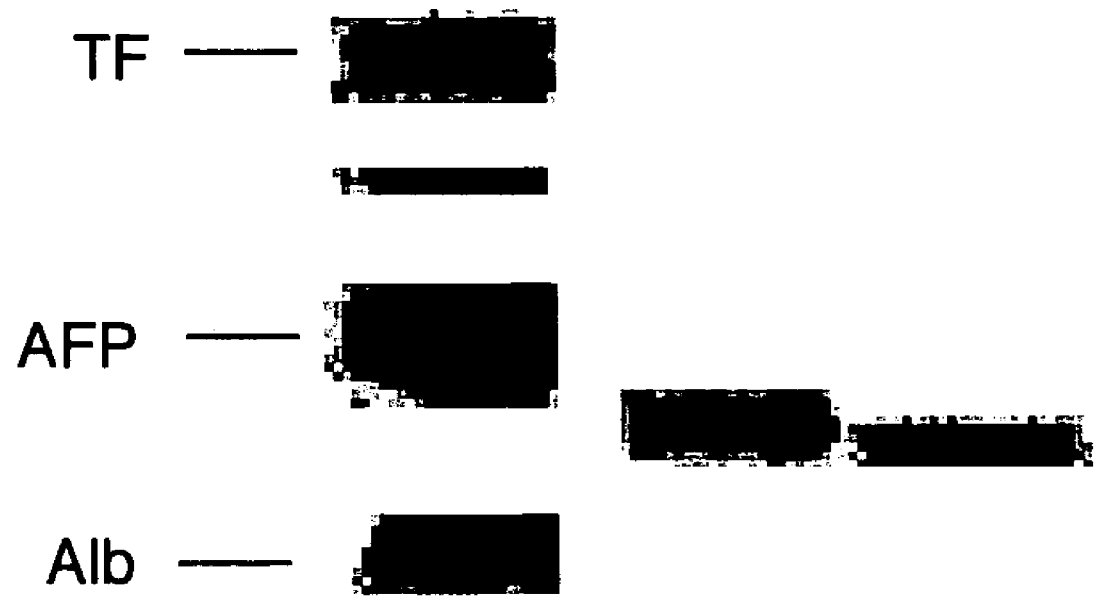
FIG. 1C is series of FPLC chromatograms showing the elution profile of HuAFP and ErAFP from a MonoQ anion exchange column. The superimposed chromatograms identify HuAFP (Chromatogram 1) and ErAFP (Chromatogram 2).
FIG. 1D is a series of HPLC chromatograms showing the elution profile of HuAFP and ErAFP obtained by passing 50 □g of HuAFP and ErAFP through a reverse phase Delta Pak C18 column (Waters) and eluting with a gradient of 0-100% acetonitrile in 0.1% TFA. The superimposed chromatograms identify HuAFP (Chromatogram 1) and ErAFP (Chromatogram 2).
Figure 1B:
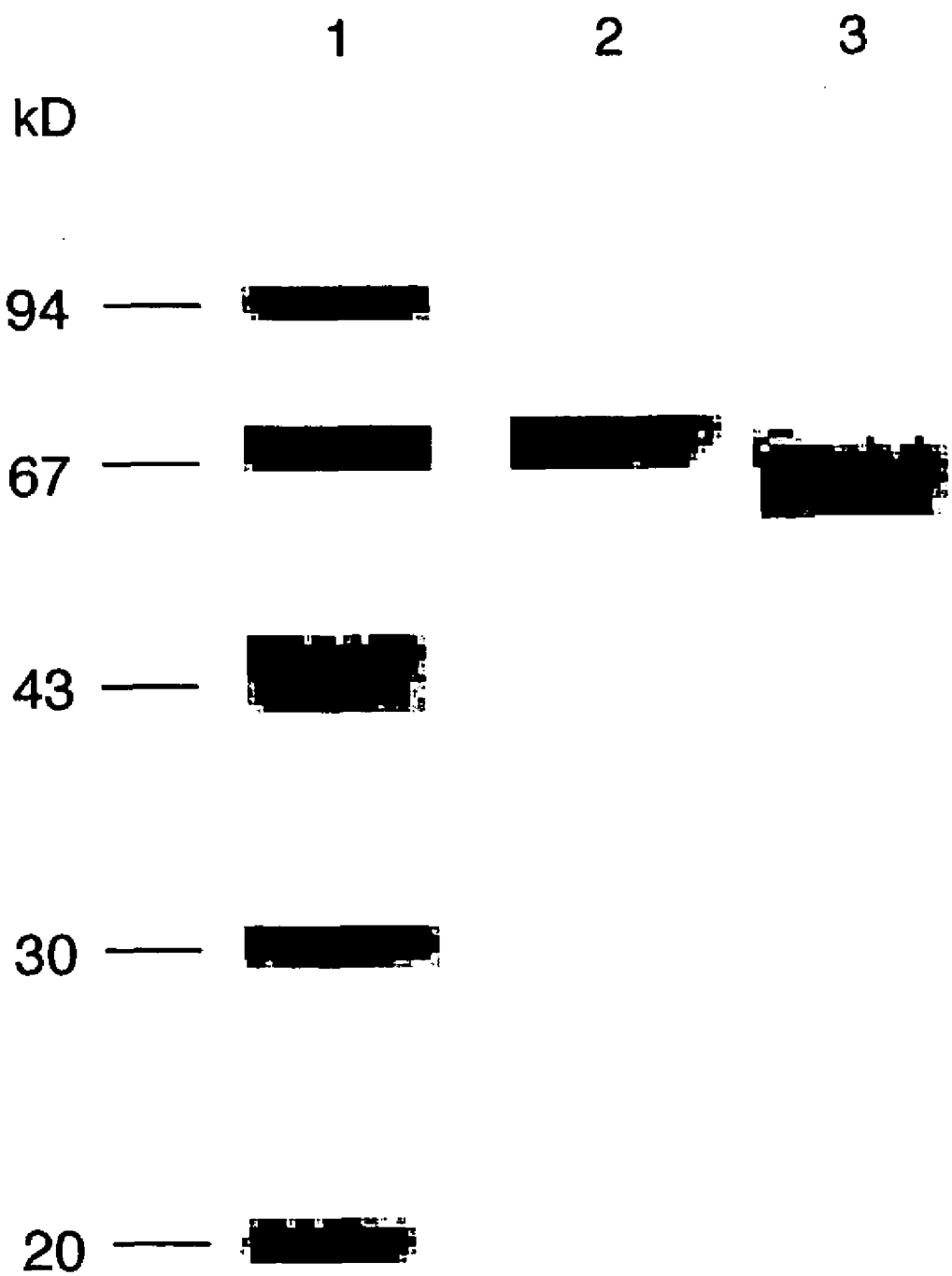
Figure 1C:
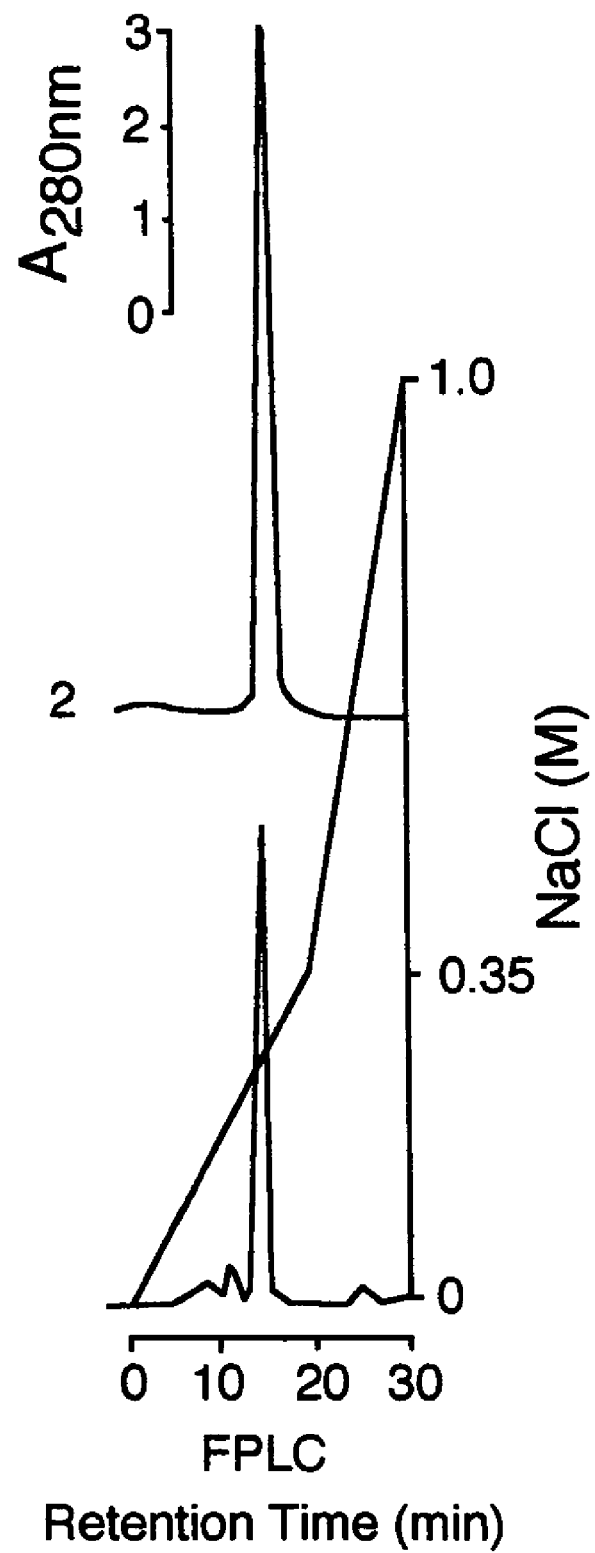
Figure 1D:
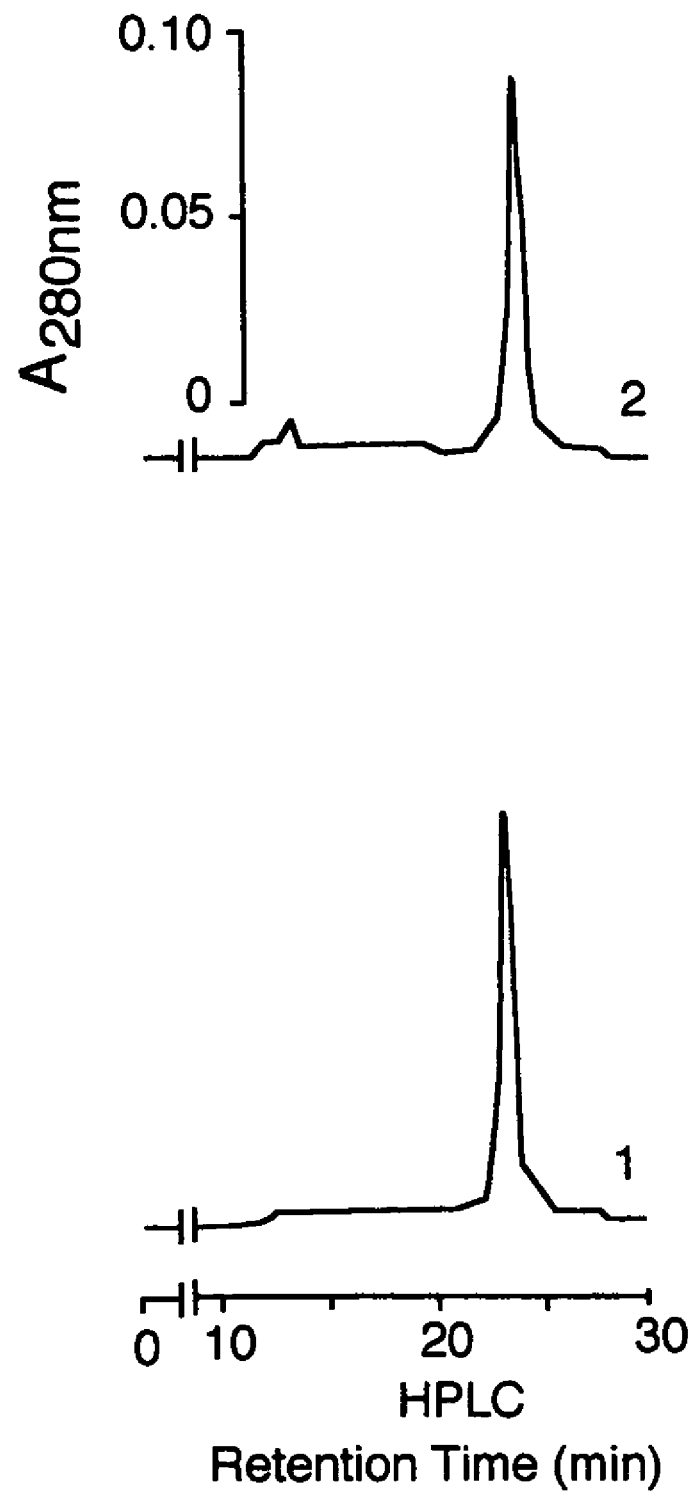

Purity of isolated rHuAFP expressed in *E. coli* was verified as a single band on Coomassie stained APAGE and SDS-PAGE are shown in FIG. 1A-1B, respectively. Soluble monomeric rHuAFP derived from *E. coli* was obtained by eluting a protein fraction containing rHuAFP employing Q-sepharose chromatography. Approximately 1 mg of pure rHuAFP per liter of bacterial culture was recovered as a single homogeneous peak by FPLC Mono-Q anion exchange with 220-230 mM NaCl and migrated at approximately 65 kD on SDS-PAGE (FIG. 1B). Recombinant HuAFP exhibits a lower molecular weight on SDS-PAGE than natural HuAFP, since prokaryotic expression systems lack the enzymatic machinery required for glycosylation of proteins. Rechromatographed samples of pure rHuAFP on FPLC and HPLC yielded a single peak as shown in FIG. 1C and FIG. 1D, confirming the purity of the rHuAFP preparation. In addition, N-terminal sequencing data correspond to the expected amino acid sequence at the N-terminus of rHuAFP.

Inhibition of the AMLR

The immunosuppressive activity of rHuAFP was assessed by its ability to suppress human AMLR. As shown in FIG. 3A, rHuAFP inhibited the proliferative response of autoreactive lymphocytes stimulated by autologous non-T cells, throughout the 4 to 7 day time course measuring autoproliferation.

Results from dose-response studies performed at the peak of T cell autoproliferation, as shown in FIG. 3B, demonstrate that the addition of rHuAFP at the initiation of cultures suppressed the AMLR in a dose-dependent manner. Furthermore, parallel viability studies established that the inhibitory activity of rHuAFP on human autoreactive T cells was not due to non-specific cytotoxic effects.

To further substantiate that rHuAFP was the agent responsible for the inhibition of autoproliferating T cells, blocking of rHuAFP-mediated suppression of the AMLR was performed using commercial murine anti-human AFP monoclonal antibodies (MAb). As illustrated in FIG. 4, suppression of proliferating autoreactive T cells by 100 µg/ml of rHuAFP was completely blocked by anti-HuAFP MAb. The addition of 100 µg/ml of HSA did not diminish the AMLR response and the presence of MAb alone in the reaction culture was without any effect.

Recombinant polypeptides produced in prokaryotic expression systems are at risk for contamination with host cell lipopolysaccharide (LPS) during their isolation from bacteria. It has been demonstrated that small amounts of LPS can antagonize the biological activities of cytokines, thereby impairing the immune responsiveness of macrophages. Accordingly, the effect of endotoxin on various rHuAFP preparations was evaluated by performing AMLR experiments with recombinant protein depleted of endotoxin by passage over Detoxi-gel (Pierce) versus that of rHuAFP which was untreated. Results of these experiments showed that both preparations had equivalent levels of immunosuppressive activity.

As shown in FIG. 3A and FIG. 3B, the results of this study also demonstrate that rHuAFP suppresses the proliferation of autoreaction T cells with a potency equivalent to glycosylated rHuAFP by eliciting inhibitory effects on autoproliferating T cells throughout the in vitro reactions, with highly significant inhibition being achieved with rHuAFP concentrations ranging from 5 µg/ml to 100 µg/ml.

Suppression of Autoproliferating and Mitogen Responsive Lymphocytes by BrAFP

In order to address in a definitive manner whether post-synthetic alterations play a role in mediating the immunosuppressive properties of AFP, we assessed the ability of BrAFP and ErAFP, which is not post-translationally modified, to suppress the proliferative response of autoreactive T cells in the AMLR. In FIG. 5, 100 µg/ml of BrAFP and ErAFP added at the initiation of the AMLR suppressed the lymphoproliferative response by 57% and 58%, respectively. Moreover, BrAFP and ErAFP anti-proliferative activity was blocked by the addition of anti-human AFP Mab. An equivalent amount of HSA augmented the reaction. The possibility that AFP might be causing a shift in the kinetics of the AMLR was eliminated, when rHuAFP, at a concentration of 100 µg/ml, was shown to inhibit autoreactive T lymphocytes from proliferating in response to autologous non-T cells throughout the autoproliferation stages of the time course from 96 to 168 hours (FIG. 3A).

We next examined the effects of various concentrations of rAFP on DNA synthesis in autoproliferating T cells. A representative experiment (FIG. 3B) demonstrates a marked dose-dependent inhibition of $^3$H-thymidine incorporation, with significant anti-proliferative effects still observed at 12 µg/ml. Viability studies established that the inhibitory activity of rAFP on human autoreactive T cells was not due to non-specific cytotoxic effects.

We carried out experiments in serum-free media to control for the possibility that exogenous serum factors may interact with the genetically engineered protein and mediate the antiproliferative activity of recombinant human AFP. As shown in FIG. 6, experiments 1 and 2 demonstrate that the addition of 100 µg/ml of either BrAFP or ErAFP to in vitro cultures containing mitogen stimulated PBMC in RPMI media supplemented with 2 mg/ml HSA reduced lymphoproliferation by more than 60%. The addition of 100 µg/ml HSA also reduced lymphoproliferation by more than 60%. The addition of HSA at 100 µg/ml had no effect on the Con A assay. These results demonstrate that neither post-translational modifications nor exogenous serum factors mediate AFP immunosuppression.

Endotoxin does not Influence AFP-Mediated Immunosuppression

Recombinant polypeptides produced in prokaryotic expression systems are at risk for contamination with host cell lipopolysaccharides (endotoxin) during their isolation from bacteria. It has been demonstrated that small amounts of LPS can antagonize the biological activities of cytokines, thereby impairing the immune responsiveness of macrophages (Bogdan, et al. *J. Immunol.* 151:301-331, 1993). We therefore evaluated the effect of endotoxin on various ErAFP preparations by performing AMLR experiments with recombinant protein that had been treated to remove endogenous endotoxin by passage over Detoxi-gel (Pierce) versus that ErAFP which was not subjected to the affinity resin. As shown in FIG. 5, Exp 3, a five fold reduction in the amount of endotoxin to levels that are below those that stimulate the release of interleukin 1 from human monocytes (buff, et al. *J Immunol. Methods* 52:323-331, 1982) did not alter the immunosuppressive activity of the recombinant protein.

Immunosuppression by a 35 kD Fragment Corresponding to an NH$_2$-Terminus-Deletion of Full-Length ErAFP An immunoblot analysis of whole bacterial cell extracts containing ErAFP identified, in addition to the 67 kD whole AFP molecule, an immunoreactive protein band with an approximate molecular weight of 35 kD. This protein was purified on MonoQ FPLC. Amino terminal sequencing of the 35 kD fragment revealed that this polypeptide corresponded to the COOH two-thirds of full-length AFP, beginning at amino acid position 267:

```
    1               5                  10
    Ser-Tyr-Ile-Cys-Ser-Gln-Gln-Asp-Thr-Leu-
    (SEQ ID NO: 18)
```

Consequently, we wanted to determine whether this truncated AFP fragment termed AFP Δ(1-226) retained the immunosuppressive activity that is observed with the intact molecule. For comparison, the 25 kD fragment was evaluated in parallel with the complete ErAFP molecule for its ability to down regulate in vitro T cell proliferative reactions. It was observed that the AFP Δ(1-226) polypeptide was similar to full-length rAFP with respect to mediating immunoregulation, suppressing the AMLR throughout the kinetics of autoproliferation (FIG. 3) and inhibiting mitogen induced PBL proliferation by 61% (FIG. 6, Exp. 3). This finding indicates that the first 266 amino acids of AFP are not required for immunoregulation.

Generation of a Bioactive AFP Fragment Corresponding to Domain 3

The previous study indicated that immunoregulatory active sites are present within the last two thirds of Domain 2 and intact Domain 3. Thus, a gene segment corresponding to the third domain of AFP (Morinaga, et al. *Proc. Natl. Acad. Sci. USA* 80:4604, 1983) was cloned by PCR into *E. coli*. The protein was identified by immunoblot employing anti-human AFP polyclonal antibodies and was subsequently purified by Q-sepharose and Mono Q anion exchange chromatography. The inhibitory activity of Domain 3 on autoproliferating and mitogen induced proliferating T lymphocytes was performed in parallel with full-length rAFP. As shown in the representative experiment in FIG. 7A, the truncated AFP segment suppressed Con A stimulated PBL's by 60% and inhibited the AMLR by 79%, whereas full-length rAFP downregulated the same in vitro responses by 50% and 58% respectively. These results demonstrate that active sites for immunoregulation exist in the latter third of the AFP molecule.

Autoimmune Disease

As is discussed above, autoimmune diseases are characterized by a loss of tolerance to self antigens, causing cells of the immune systems, e.g., T or. B cells (or both), to react against self tissue antigens. Autoimmune diseases may involve any organ system, although some are affected more commonly than others. Examples of tissues affected by autoimmune conditions include: the white matter of the brain and spinal cord in multiple sclerosis; the lining of the joints in rheumatoid arthritis; and the insulin secreting β islet cells of the pancreas in insulin-dependent diabetes mellitus. Other forms of autoimmune disease destroy the connections between nerve and muscle in myasthenia gravis or destroy the kidneys and other organs in systemic lupus erythematosus. Examples of other autoimmune diseases include, without limitation, Addison's disease, Crohn's disease, Graves' disease, psoriasis, scleroderma, and ulcerative colitis.

The art provides a wide variety of experimental animal systems, transgenic and non-transgenic, for testing therapies for human illness involving autoimmune diseases (see e.g., Paul, W. E., *Fundamental Immunology*, 2nd ed., Raven Press, New York, 1989; and Kandel et al. *Principles of Neural Science*, 3rd ed., Appleton and Lange, Norwalk, Conn., 1991; and *Current Protocols In Immunology*, Coligan, J. E., Kruisbeek, A. M., Margulies, D. H., Shevach, E. M., and Strober, eds., Green Publishing Associates (John Wiley & Sons), New York, 1992). Based on the above-described experimental results showing immunosuppressive activity of unglycosylated rHuAFP, it is reasonable to believe that other autoimmune diseases can be treated by administration of such rHuAFP (or fragment or analog thereof) produced in a prokaryotic system. Accordingly, the invention provides the use of rHuAFP (or a fragment or analog thereof) for treatment (i.e., prevention or suppression or amelioration or promotion of remission) of any autoimmune disease.

There now follow examples of animal systems useful for evaluating the efficacy of recombinant human alpha-fetoprotein or an immune cell anti-proliferative fragment or analog thereof in treating autoimmune diseases. These examples are provided for the purpose of illustrating, not limiting, the invention.

Multiple Sclerosis

Multiple sclerosis (MS) is a demyelinating disease involving scattered areas of the white matter of the central nervous system. In MS, myelin basic protein and proteolipid protein are the major targets of an autoimmune response involving T lymphocytes, among other immune system components. Loss of the myelin sheath of nerve cells (demyelination) occurs, resulting in neurological symptoms that culminate in coma or paralysis.

Experimental autoimmune encephalomyelitis (EAE) is a primary model used in the art to examine and assess the effectiveness of therapeutic agents for treating MS. EAE is an inflammatory autoimmune demyelinating disease induced in laboratory animals by immunization with central nervous system tissue. When animals (e.g., mice, rats, guinea pigs, rabbits, monkeys, etc.) are injected with adjuvant, e.g., complete Freund's adjuvant, plus myelin basic protein or proteolipid protein, EAE is induced, which is similar, pathologically to MS (see e.g., Alvord et al., *Experimental Allergic Encephalomyelitis—A Useful Model for Multiple Sclerosis*, Liss, New York, 1984; Swanborg, *Meth. Enzymol.* 162:413, 1988; and McCarron et al., *J. Immunol.*, 147: 3296, 1991.)

To evaluate rHuAFP or a fragment or analog thereof, EAE is induced in an appropriate laboratory animal, e.g., a mouse or rabbit, according to methods known in the art. To evaluate the compound's immunosuppressive effect on EAE, i.e., its ability to prevent or ameliorate EAE, the compound is administered according to standard methods, e.g., intravenously or intraperitoneal, at an appropriate dosage on a daily basis. Generally, administration is initiated prior to inducing EAE and/or after the clinical appearance of EAE. Control animals receive a placebo, e.g., human serum albumin, similarly administered as for rHuAFP or related molecules. The effect of the test molecules on EAE is monitored according to any standard method. For example, weight loss and muscle paralysis in EAE-induced animals is monitored on a daily basis. If desired, histological inspection (e.g., by using any standard histochemical or immunohistochemical procedure, see e.g., Ausubel et al., *Current Protocols In Molecular Biology*, Greene Publishing Associates (John Wiley & Son), New York, 1994; Bancroft and Stevens, *Theory and Practice of Histochemical Techniques*, Churchill Livingstone, 1982) of brain and spinal cord tissues is performed and tissue samples examined microscopically for evidence of EAE, e.g., evidence of perivascular cellular infiltrates. Comparative studies between treated and control animals are used to determine the relative efficacy of the test molecules in preventing or ameliorating EAE. A molecule which prevents or ameliorates (decreases or suppresses or relieves or promotes remission of) the symptoms of EAE is considered useful in the invention.

Rheumatoid Arthritis

Rheumatoid arthritis (RA) is a common chronic illness in which the synovial membrane of multiple joints becomes inflamed, causing damage to cartilage and bone. RA is associated with human lymphocyte antigen (HLA)-DR4 and considered to be an autoimmune disorder involving T cells, see e.g., Sewell et al., *Lancet* 341: 283, 1993. RA results from a complex interaction of synovial cells with various cellular elements (and their soluble products) that infiltrate from the circulation into the synovial lining of joints. A series of biological events occur which ultimately lead to a lesion which invades and erodes collagen and the cartilage matrix of the joint.

A number of animal models of RA, e.g., the MRL-lpr/lpr mouse, are known in the art which develop a form of arthritis resembling the human disease (see e.g., *Fundamental Immunology*, supra). Alternatively, autoimmune collagen arthritis (ACA) and adjuvant arthritis (AA) can be induced in an appropriate animal according to standard methods.

To evaluate rHuAFP or a fragment or analog thereof on immunosuppressive on RA, i.e., the compound's ability to prevent or ameliorate RA, the test molecule is administered to a MRL-lpr/lpr mouse according to standard methods, e.g., intravenously or intraperitoneally, at an appropriate dosage on a daily basis. Generally, administration is initiated prior to the onset of RA and/or after the clinical appearance of RA. Control animals receive a placebo, e.g., human serum albumin, similarly administered as for rHuAFP or related molecules. The effect of the test molecule on RA is monitored according to standard methods. For example, analysis of the cellular component(s) of a synovial joint are monitored on a daily basis. If desired, histological inspection (e.g., by, using any standard histochemical or immunohistochemical procedure, see e.g., Ausubel et al., supra; Bancroft and Stevens, supra) of the synovial joint is performed and tissue samples examined microscopically for evidence of RA, e.g., evidence of erosion of collagen and cartilage matrix in a joint. Comparative studies between treated and control animals are used to determine the relative efficacy of the test molecule in preventing or ameliorating RA. A test molecule which prevents or ameliorates (decreases or suppresses or relieves or promotes remission of) the symptoms of RA is considered useful in the invention.

Mysthenia Gravis

Myasthenia gravis (MG) is a disorder of neuromuscular transmission in which there are autoantibodies against acetylcholine receptors of neuromuscular junctions. Antibodies attack the junction, causing weakness and paralysis. Females are afflicted twice as often as males, typically during the third decade of life. Muscular weakness is the predominant feature of the disease. Clinical signs include drooping of the eyelids and double vision. There is an association between MG and hyperthyroidism.

Experimental autoimmune MG (EAMG) has been studied in a variety of animals including rabbits, monkeys, Lewis rats and inbred strains of mice (see e.g., *Principles of Neural Science*, supra), the symptoms of EAMG resemble the essential characteristics of the human disease. A single injection of acetylcholine receptor, e.g., purified from the electric organs of the eel *Torpedo californica*, along with adjuvants, causes an acute phase of weakness within 8 to 12 days and then chronic weakness after about 30 days. The response to the eel receptor is T cell dependent. The C57BL/6 strain (H-$2^B$) is a high responder to *Torpedo* receptor and highly susceptible to EAMG.

To evaluate rHuAFP or a fragment or analog thereof, EAMG is induced in an appropriate laboratory animal, e.g., the C57BL/6 strain (H-$2^B$) mouse, according to methods known in the art. To evaluate the compound's immunosuppressive effect on EAMG, i.e., its ability to prevent or ameliorate EAMG, the compound is administered according to standard methods, e.g., intravenously or intraperitoneally, at an appropriate dosage on a daily basis. Generally, administration is initiated prior to inducing EAMG and/or after the clinical appearance of EAMG. Control animals receive a placebo, e.g., human serum albumin, similarly administered as for rHuAFP or related molecules. The effect of the test molecules on EAMG is monitored according to standard methods. For example, nerve stimulation in an electromyographic muscle assay (e.g., according to the methods of Pachner et al., *Ann. Neurol.* 11:48, 1982) in EAMG-induced animals can be assayed. If desired, histological inspection (e.g., by using any standard histochemical or immunohistochemical procedure, see e.g., Ausubel et al., supra; Bancroft and Stevens, supra) of tissue samples is performed and tissue samples examined microscopically for evidence of EAMG, e.g., evidence of monocyte infiltration and/or autoantibody localization at acetylcholine receptors of neuromuscular junctions. Comparative studies, between treated and control animals are used to determine the relative efficacy of the test molecules in preventing or ameliorating EAMG. A molecule which prevents or ameliorates (decreases or suppresses or relieves or promotes remission of) the symptoms of EAMG is considered useful in the invention.

Insulin-Dependent Diabetes Mellitus

Diabetes is a disorder of glucose metabolism. Insulin-dependent diabetes mellitus (IDDM), also known as Type I diabetes, is an autoimmune disease characterized by T-cell mediated destruction of pancreatic β cells in the islets of Langerhans, accompanied by an immune response to a diversity of self peptides leading to hyperglycemia, among other pathological events. IDDM patients depend on exogenous insulin to maintain normal glucose metabolism. Humans at risk for developing IDDM can be identified prior to onset of hyperglycemia by the abnormal occurrence of autoantibodies to insulin, islet cells, glutamic acid carboxylase, as well as other autologous proteins (see e.g., Baekkeskov et al., *J. Clin. Invest.* 79:926, 1987; Dean et al., *Diabetologia* 29: 339, 1986; Rossini et al., *Annu. Rev. Immunol.* 3:289, 1985; Srikanta et al., *N. Engl. J. Med.* 308:322, 1983). Autoantibody patterns, in general, are predictive for the eventual disease progression and/or risk for developing the disease (see e.g., Keller et al., *Lancet* 341:927, 1993).

Examples of animal models which spontaneously develop IDDM resembling the human disease include the Bio-Breeding (BB) rat and nonobese diabetic (NOD) mouse. Diabetes is also experimentally induced by streptozotocin.

The BB rat spontaneously develops a disease similar to IDDM, with insulitis (infiltration of mononuclear cells into the pancreatic islets) and autoantibodies against self cells and insulin (see e.g., Baekkeskov et al., *J. Clin. Invest.* 79:926, 1987; Rossini et al, supra; Nakhooda et al., *Diabetes* 26: 100, 1977; Dean et al., *Clin. Exp. Immunol.* 69: 308, 1987).

NOD mice typically develop insulitis between 5 and 8 weeks of age, and by 7 months 70% of the females and 40% of the males become diabetic. T cells transferred from diabetic mice to young nondiabetic NOD mice induce diabetes within 2 to 3 weeks (see e.g., Bendelac et al., *J. Exp. Med.* 166:823, 1987). NOD mice usually die within 1 to 2 months after the onset of diabetes unless they receive insulin therapy.

Chemically induced diabetes is accomplished using multiple injections of small doses of streptozotocin, a drug toxic for pancreatic β cells, which causes severe insulitis and diabetes (see e.g., Kikutani et al., *Adv. Immunol.* 51:285, 1992).

Accordingly, the art provides a variety animal models resembling human IDDM which can be used to examine and assess approaches for the prevention or amelioration of diabetes involving rHuAFP (or a fragment or analog thereof).

To evaluate the immunosuppressive effect of rHuAFP or a fragment or analog thereof on the development of diabetes mouse, i.e., the compound's ability to treat or prevent insulitis and diabetes, the test compound is administered to an appropriate test animal, e.g, a NOD mouse, according to standard methods, e.g., intravenously or intraperitoneally, at an appropriate dosage on a daily basis. Generally, administration is initiated prior to the onset of insulitis and diabetes and/or after the clinical appearance of diabetic characteristics. Control animals receive a placebo, e.g., human serum albumin, similarly administered as for rHuAFP or related molecules. The effect of test molecules on insulitis and diabetes is monitored according to standard methods. For example, weight loss, ketone body formation, and blood glucose concentration is monitored on a daily basis. If desired, histological inspection (e.g., by using any standard histochemical or immunohistochemical procedure, see e.g., Ausubel et al., supra; Bancroft and Stevens, supra) of pancreatic islet cells is performed and tissue samples examined microscopically for evidence of insulitis and P cell destruction. Comparative studies between treated and control animals are used to determine the relative efficacy of the test molecules in preventing or ameliorating the diabetic condition. A molecule which prevents or ameliorates (decreases or suppresses or relieves or promotes remission of) the symptoms of diabetes, e.g., IDDM, is considered useful in the invention.

Systemic Lupus Erythematosus

Systemic lupus erythematosus (SLE) is a severe systemic autoimmune disease. About 90% of patients with this disease are young women. This marked preponderance of females is not seen before puberty or after menopause. The illness generally begins in young adulthood when a characteristic skin rash appears over cheekbones and forehead. Hair loss is common, as is severe kidney damage, arthritis, accumulation of fluid around the heart and inflammation of the lining of the lungs. In nearly half of the patients the blood vessels of the brain also become inflamed, leading to paralysis and convulsions. The activity of the disease, like other autoimmune diseases, can fluctuate: long quiescent periods of good health can terminate abruptly and inexplicably with the onset of a new attack. A large number of different autoantibodies are known to occur in SLE, e.g., autoantibodies against DNA, RNA and histones (see, e.g., *Fundamental Immunology*, supra)

A number of animal models of human SLE, e.g., inbred mouse strains including NZB mice and their $F_1$ hybrids, MRL mice, and BXSB mice, are known in the art (see e.g., Bielschowsky et al. *Proc. Univ. Otago Med. Sch.* 37:9, 1959; Braverman et al., *J. Invest. Derm.* 50: 483, 1968; Howie et al. *Adv. Immunol.* 9:215, 1968; *Genetic Control of Autoimmune Disease*, Rose, M., Bigazzi, P. E., and Warner, N. L. eds., Elsevier, Amsterdam, 1979; and *Current Protocols In Immunology*, supra). For example, the NZBxNZW $F_1$ mouse is an excellent model of human SLE, female mice develop high levels of anti-double- and single-stranded DNA autoantibodies, other anti-nuclear antibodies, and renal disease; death usually occurs at approximately 8 months (see e.g., Theofilopoulos et al., *Adv. Immunol.* 37:269, 1985).

To evaluate the immunosuppressive effect of rHuAFP or a fragment or analog thereof on SLE, i.e., the compound's, ability of rHuAFP to prevent or ameliorate SLE, test compounds are administered to an appropriate animal, e.g., the NZBxNZW $F_1$ mouse, according to standard methods, e.g., intravenously or intraperitoneally, at an appropriate dosage on a daily basis. Generally, administration is initiated prior to the onset of SLE and/or after the clinical appearance of SLE. Control animals receive a placebo, e.g., human serum albumin, similarly administered as for rHuAFP or related molecules. The effect of the test compound on SLE is monitored according to standard methods. For example, analysis of autoantibodies, e.g., anti-DNA antibodies can be monitored. If desired, histological inspection (e.g., by using any standard histochemical or immunohistochemical procedure, see e.g., Ausubel et al., supra; Bancroft and Stevens, supra) of kidney tissue is performed and tissue samples examined microscopically for evidence of SLE, e.g., evidence of lupus nephritis. Comparative studies between treated and control animals are used to determine the relative efficacy of the test compounds in preventing or ameliorating SLE. A molecule which prevents or ameliorates (decreases or suppresses or relieves or promotes remission of) the symptoms of SLE is considered useful in the invention.

Therapeutic Administration

As demonstrated above, recombinant alpha-fetoprotein, e.g., rHuAFP (or a fragment or analog thereof) is effective in inhibiting proliferation of autoimmune cells and accordingly is useful for the prevention or amelioration of autoimmune diseases including, but not limited to, multiple sclerosis, rheumatoid arthritis, diabetes mellitus, systemic lupus erythematosus, and myasthenia gravis. Accordingly, recombinant human alpha-fetoprotein (or a fragment or analog thereof) can be formulated according to known methods to prepare pharmaceutically useful compositions.

Recombinant alpha-fetoprotein, e.g., rHuAFP (or a fragment or analog thereof), is preferably administered to the patient in an amount which is effective in preventing or ameliorating the symptoms of an autoimmune disease. Generally, a dosage of 0.1 ng/kg to 10 g/kg body is adequate. If desired, administration is performed on a daily basis. Because there are no known adverse side effects related to recombinant human alpha-fetoprotein, it is believed that relatively high dosages can be safely administered. For example, treatment of human patients will be carried out using a therapeutically effective amount of rHuAFP (or a fragment or analog thereof) in a physiologically acceptable carrier. Suitable carriers and their formulation are described for example in Remington's *Pharmaceutical Sciences* by E. W. Martin. The amount of rHuAFP to be administered will vary depending upon the manner of administration, the age and body weight of the patient, and with the type of disease, and size of the patient predisposed to or suffering from the disease. Preferable routes of administration include, for example, subcutaneous, intravenous, intramuscular, or intradermal injections which provide continuous, sustained levels of the drug in the patient. In other preferred routes of administration, rHuAFP can be given to a patient by injection or implantation of a slow release preparation, for example, in a slowly dissociating polymeric or crystalline form; this sort of sustained administration can follow an initial delivery of the drug by more conventional routes (for example, those described above). Alternatively, rHuAFP can be administered using an infusion pump (e.g., an external or implantable infusion pump), thus allowing a precise degree of control over the rate of drug release, or through installation of rHuAFP in the nasal passages in a similar fashion to that used to promote absorption of insulin. As an alternative to nasal transmucosal absorption, rHuAFP can be delivered by aerosol deposition of the powder or solution into the lungs.

Furthermore, the method(s) of the invention can also employ combination therapy in which rHuAFP is administered either simultaneously or sequentially with a therapeutic agent such as a general or specific tolerizing agent (e.g., an anti-idiotypic agent (e.g., a monoclonal) or a therapeutic vaccine or an oral agent (e.g., insulin, collagen or myelin basic protein) or a cytokine (e.g., I-15) or an interferon ($\alpha$-interferon) or an immunosuppressive agent. Preferably, an immunosuppressive agent is administered in an effective dose which is lower than the standard dose when the immunosuppressive agent is used by itself. Preferred immunosuppressive agents are cyclosporine, FK-506, steroids, azathioprine, or 15-deoxyspergualin.

Treatment is started generally with the diagnosis or suspicion of an autoimmune disease and is generally repeated on a daily basis. Protection or prevention from the development (or progression or exacerbation) of an autoimmune disease is also achieved by administration of rHuAFP prior to the onset of the disease. If desired, the efficacy of the treatment or protection regimens is assessed with the methods of monitoring or diagnosing patients for autoimmune disease.

The method(s) of the invention can also be used to treat non-human mammals, for example, domestic pets, or livestock.

OTHER EMBODIMENTS

In other embodiments, the invention includes the use of rHuAFP (or fragment or analog thereof) for the prevention or treatment of acquired immunodeficiency syndrome (AIDS). To evaluate the immunosuppressive effect of rHuAFP or a fragment or analog thereof on AIDS, i.e., the compound's ability to prevent or ameliorate an autoimmune component of AIDS, test compounds are administered to an appropriate animal (e.g., a human patient), according to standard methods, e.g., intravenously or intraperitoneally, at an appropriate dosage on a daily basis as is discussed above. Generally, administration is initiated prior to the onset of AIDS and/or after the clinical appearance of AIDS. Control animals receive a placebo, e.g., human serum albumin, similarly administered as for rHuAFP or related molecules. The effect of the test compound on AIDS is monitored according to standard methods. For example, analysis of the ability of the test compound to inhibit or prevent or ameliorate the destruction of helper T cells can be monitored. Comparative studies between treated and control animals are used to determine the relative efficacy of the test compounds in preventing or ameliorating AIDS. A molecule which prevents or ameliorates (decreases or suppresses or relieves or promotes remission of) the symptoms of AIDS is considered useful in the invention.

In the invention also includes the use of a therapeutically effective amount rHuAFP (or fragment or analog thereof) for inhibiting the rejection of a transplanted organ (e.g., the heart, the liver, the lung, the pancreas, and the kidney), tissue (e.g., skin, bone marrow, dura mater, bone, implanted collagen, an implanted bioreactor), or cell (e.g., $\beta$ islet cells of the pancreas, stem cells, hematopoietic cells, lymph cells, neuroendocrine or adrenal cells) in a mammal. Such transplanted organs, tissues, or cells may be derived from any source, e.g., such biological material can be allogenic, phenogenic, autologous, synthetic, artificial or genetically-engineered. For example, the method can also be used when the patient is the recipient of an allograft such a heart or kidney from another species.

In one working example, the immunosuppressive effect of rHuAFP on clinical transplantation, i.e., the ability of rHuAFP to prevent or ameliorate transplant rejection (e.g., hyperacute rejection, acute rejection and chronic rejection), is evaluated by administering rHuAFP to an NIH minipig according to standard methods, e.g., intravenously or intraperitoneally, at an appropriate dosage on a daily basis. Generally, administration of rHuAFP is initiated prior to the transplant, e.g., transplantation of a kidney and/or after the transplant procedure. Control animals receive a placebo, e.g., human serum albumin, similarly administered as for rHuAFP. The effect of rHuAFP on transplant rejection is monitored according to standard methods. One manifestation of the rejection process is diminished function of the transplanted organ, for example, analysis of urine output can be monitored. If desired, histological inspection (e.g., by using any standard histochemical or immunohistochemical procedure, see e.g., Ausubel et al., supra; Bancroft and Stevens, supra) of kidney tissue is performed and tissue samples obtained by biopsy are examined microscopically for evidence of transplant rejection, e.g., chronic interstitial fibrosis, vascular thrombosis, or the presence of abnormal lymphocytic infiltrates. Comparative studies between treated and control animals are used to determine the relative efficacy of rHuAFP in preventing or ameliorating transplant rejection. Recombinant HuAFP (a fragment or analog thereof) which prevents or ameliorates (decreases or suppresses or relieves or promotes remission of) the symptoms of transplant rejection is considered useful in the invention.

Graft-Versus Host Disease

Studies of neonatal mice grafted with allogeneic T cells indicates that treatment with rHuAFP has an inhibitory effect on GVHD. SCID mice at 3 days of age were used as recipients because of their lack of functional B and T cells. In this experimental system the grafted T cells can react against the host whereas the recipient mice cannot mount an effective response against the graft. A SCID mouse (3 days post-natal) was injected i.p. with 100 µl PBS and 4 hours later with $5 \times 10^6$ spleen T cells from C57Bl/6 in 100 µl PBS on day 0. This mouse was thereafter injected with 100 µl PBS day 1 and 3. The results from this mouse are presented in the B6 column. A SCID mouse (3 days post-natal) was injected i.p. with 200 µg rHuAFP in 100 µl PBP (100 µg rHuAFP per gram body weight) and 4 hours later with $5 \times 10^6$ spleen T cells from C56Bl/6 in 100 µl PBS on day 0. This mouse was thereafter injected with 50 µg rHuAFP per gram body weight in 100 µl PBS on day 1 and 3. The results from this mouse are presented in the B6+AFP column.

In this experimental system loss of weight and decreased cell numbers in the lymphoid organs are cardinal signs of severe GVHD. Differences could be detected in weight, as the mouse inj. B6+AFP gained more weight than the one inj. B6 (Table 2). The weight of the AFP treated mouse was close to that of age-matched untreated SCID mice at our animal facilities.

TABLE 2

| | Weight (g) | |
|---|---|---|
| Day | inj B6 | inj B6 + AFP |
| 0 | 1.6 | 1.9 |
| 3 | 2.8 | 3.2 |
| 5 | 3.2 | 4.1 |

Moreover, at 5 days p.i. the total cell numbers in spleen, bone marrow, and liver were lower in the mouse inj. B6 when compared to the mouse inj. B6+AFP (Table 3). A SCID mouse received an allogenic T cell graft in the absence (inj. B6) or presence (inj. B6+AFP) of rHuAFP as described for FIG. 5. At 5 days post-injection, organ size was determined an presented by the number cells in each tissue (cells×$10^{-6}$).

TABLE 3

| | Organ sizes (cells × $10^{-6}$) | |
|---|---|---|
| Organ | inj. B6 | inj. B6 + AFP |
| Spleen | 12 | 32 |
| Bone Marrow | 6.0 | 9.2 |
| Liver | 0.56 | 1.0 |

At day 5 p.i. the mouse injected with C57Bl/6 only had a higher percentage of exogenous T cells in spleen, bone marrow, and liver than the mouse treated with AFP as determined in FACS. Also, at this time-point the amount of cells expressing CD19 and CD117 (c-kit) was lower in the liver of the mouse that was not treated with AFP both when counted in percentage and total cell numbers which indicates a more severe GVHD. When sera from the mice were analyzed for interferon-γ content, an interleukin that is elevated during acute GVHD, the concentration in mice inj. B6 (6.5 ng/ml) was twice as high as for mice inj. B6+AFP (3.1 ng/ml). Thus, these data from GVHD studies indicates an inhibitory effect of AFP on the allogeneic T cells and suppress GVHD.

Transplant Rejection

Results

Enhanced MHC Expression on BM Cells Cultured in the Presence of rHuAFP.

BM cells from adult C.B-17 mice cultured for three days in the presence of optimal doses of IL-3 (2000 U/ml), IL-7 (1%), or rHuAFP (100 µg/ml) were analyzed for expression of MHC class I (H-2K$^d$) and MHC class II (1-Ad). Bone marrow cells ($2.5 \times 10^6$/ml) from C.B.-17 mice were cultured in 2 ml of f-DMEM medium containing 1% FCS in the presence or absence of IL-3, IL-7, or rHuAFP. At 3 days of culture, cells were harvested and stained with anti-H-2K$^d$ and analyzed in FACS. The figure shows percent of cells with high expression of H-2K$^d$ in medium control, IL-3, IL-7, and rHuAFP cultures in a representative experiment. As demonstrated in a representative experiment, a substantial increase in the intensity of MHC class I (MHC I) expression was seen on BM cells cultured in the presence of rHuAFP where 90% of the cells were MHC I$^{high}$ compared to 61%, 40% and 33% for cells cultured with IL-3, IL-7 and with medium only respectively (FIGS. 10A and 10B). In the individual experiments, rHuAFP induced high intensity of MHC I expression on between 88% and 98% of the cells and interestingly, similar percentages were seen even after a 10-fold decrease in the concentration of rHuAFP, i.e. to 10 µg/ml.

Despite the fact that the total cell numbers were not higher in cultures supplemented with AFP than with IL-3 or IL-7 (FIG. 13), also the absolute numbers of cells with high expression of MHC I were significantly higher in the presence of AFP (FIG. 2B). (Schneider). Bone marrow cells ($10^6$ to $2.5 \times 10^6$/ml) from C.B-17 mice were cultured in 2 ml of f-DMEM medium containing 1% FCS in the presence or absence of IL-3, IL-7, or rHuAFP. At 3 days of culture, cells were harvested and cell viability was determined with the trypan blue dye exclusion test. The figure shows mean percent standard deviation of viable cells at 3 days of culture out of total number of seeded cells at day 0 as counted from 4 separate experiments where the total number of seeded cells varied between $2 \times 10^6$ to $5 \times 10^6$ per well. The cells were cultured and treated as described in FIG. 1A. The figure shows absolute numbers of cells with high expression of H-2K$^d$ in medium, control, IL-3, IL-7, and rHuAFP cultures in a representative experiment.

An increased frequency of MHC class II (MHC II) positive cells was also seen in the presence of rHuAFP. Bone marrow cells from C.B-17 mice were cultured as described in FIGS. 11A and 11B. At 3 days of culture, cells were harvested and stained with anti-I-A$^d$ and analyzed in FACS. The figure shows percent of cells positive for I-A$^d$ in medium control, IL-3, IL-7, and rHuAFP cultures in representative experiment. Flow cytometry analysis showed that 55% of the BM cells were MHC II$^+$ after three days of culture with rHuAFP (FIG. 11B) with was nearly twice the percentage at day 0 (data not shown) and more than in the medium control and in the presence of IL-3 and IL-7.

The absolute numbers of MHC II positive cells were similar in IL-7 and AFP cultures but significantly higher than in the medium control and IL-3 cultures (FIG. 11B). (Schneider) Bone marrow cells from C.B-17 mice were cultured as described in FIG. 1A and harvested and analyzed as described in FIG. 11A. The figures shows absolute numbers of cells positive for I-A$^d$ in medium control, IL-3, IL-7, and rHuAFP cultures in representative experiment.

There are numerous studies which have shown that AFP can exert growth regulatory effects of MHC class II expressing cells such as monocytes and thyroid epithelia cells (Wang, et al. *Hepatology* 22:921-928, 1995). We wanted to ascertain whether I-$A^k$ expressing cells within whole bone marrow would be modulated upon co-culturing with 100 μg/ml rHuAFP. Simultaneously, we investigated the effects of rHuAFP on MHC class I expressing cells within the adult BM. This was performed employing fluorescein-conjugated anti-H-$2K^k$ antibodies. As illustrated in FIG. 12A. only a minority of cells in normal BM exhibit a high expression level of MHC molecules. When BM cells were cultured in the presence of rHuAFP, there is a distinct pattern of staining intensity. AFP increased the proportion of I-$A^k$ expressing cells to 40% versus 12% in control cultures of media alone or containing equivalent amounts of either mouse or human albumin. Cells defined as H-$2K^{k,high}$ represented approximately 80% of the total BM analyzed in cultures containing rHuAFP, illustrating a 15 fold increase over control cultures with mouse and human albumin additions or no protein additions.

The Effects of AFP on BM Cell Cultures Cannot be Reproduced with Human or Mouse Albumin.

AFP share many physio-chemical properties with albumin, such as the overall structures, including the three-domain structure, and comparable binding properties. Therefore we determined whether the effects in BM cells observed for AFP could also be ascribed to mouse or human albumin. For this purpose BM cells from CBA/J mice were cultured in the presence of 100 μg/ml of rHuAFP, human albumin, or mouse albumin. As demonstrated in FIG. 12B neither human or mouse albumin shared the properties of AFP considering increase in MHC I or II intensity or enhanced frequencies of DN T cells and IgM positive B lineage cells. Instead, human and mouse albumin cultures were comparable to the medium control in these experiments.

EXPERIMENTAL

Materials and Methods

Mice C.B-17 (H-$2^d$) and CBA/J (H-$2^k$) mouse strains were obtained from Bomholtsgaard, Denmark and wee then bred and maintained in our own animal facilities.

Preparation of bone marrow cells. Femurs and tibias were removed aseptically from mice and flushed with PBS using a syringe. Single cell suspensions were then washed three times in PBS. Cell viability was determined by the trypan blue dye exclusion test.

Membrane labeling of hone marrow cells with PKH67-G1. Bone marrow cells were labeled using the PKH67 Green Fluorescent Cell Linker Kit (PKH67-GL, Sigma Biosciences, St. Louis, Mo., USA). Briefly, cells were diluted in Diluent C ($2 \times 10^7$ cells/ml) and then mixed with an equal volume of $2 \times 10^{-6}$ M PKH67 dye in Diluent C to a final concentration of $10^{-6}$ M dye and $10^7$ cells/ml. After 2 minutes incubation at 25° C. the reaction was stopped by adding an equal volume of complete f-DMEM, medium containing 10% FCS. Cells were washed and analyzed on a FACScan® flow cytometer (Becton Dickinson, San Jose, Calif.) to determine labeling intensity.

In Vitro Cultures and Cell Proliferation. BM cells were cultured in 37° C. in a humidified atmosphere of 7.5% $CO_2$ in an incubator (Biocenter 2001, Salvis AG, Reussbuhl, Switzerland) in flat-bottomed 24 well plates (A/S Nunc, Roskilde, Denmark) or round-bottomed 96 well plates (Corning Costar, Acton, Mass., USA) in f-DMEM medium supplemented with 2 mM L-glutamine, $5 \times 10^5$ M 2-mercaptoethanol, and 10 μg/ml gentamicin. The cultures were complemented with recombinant IL-3 (Karasuyama & Melchers, *Eur. J. Immunol.* 18:97-104, 1998; kindly provided by Prof. Jan Andersson, Basel Institute for Immunology, Switzerland), crude supernatant from the IL-7 producing hybridoma JM-IL-7 (kindly provided by Dr. Jan Andersson), recombinant human alpha-fetoprotein (Boismenu, et al. *Adv. Exp. Med. Biol.* 383: 255-269, 1995), human albumin, or mouse albumin and supplemented with 5 μg/ml transferrin, 1% fetal calf serum (FCS), or 0.5% autologous normal mouse serum (NMS). Cells from 24-well plates were harvested for flow cytometry analysis and determined for cell viability by the trypan blue dye exclusion test. Cell proliferation was determined by incubating triplicate cultures in round-bottomed 96 well plates with 1 μCi/culture of $^3$H-thymidine (Amersham International plc, Amersham, UK; spec. act., 925 Gbq/mmol) for 4 h prior to harvest onto glassfiber filters in a multiple cell harvester (1295-004 Betaplate® Pharmacia LKB, Uppsala, Sweden). Radioactivity on dried filters was measured by scintillation counting in a beta counter (1205 Betaplate®, Pharmacia LKB, Uppsala, Sweden).

Flow cytometry analysis. If not otherwise stated, the mAbs were obtained from PharMingen, San Diego, Calif. All steps were carried out at 4° C. Cells ($10^5$ to $10^6$ per sample) were pre-incubated for 30 minutes with 50 μl crude supernatant from 2.4 G2 hybridomas, washed once in 250 μl PBS and then stained for 30 minutes with pretitered concentrations of the following mABs (obtained from Pharmigen) in 50 μl of PBS: FITC-labeled anti-H-$2K^d$ (SF 1-1.1), biotinylated anti-I-$A^d$ (AMS-32.1), FITC-labeled anti-H-$2K^k$ (AF2-12.1), and biotinylated anti-I-$A^k$ (11-5.2). The cells were then washed once in 250 μ PBS and cells stained with biotinylated mAb were incubated for 25 min were streptavidin-PE (Becton Dickinson, San Jose, Calif.) followed by three washes with 250 μl of PBS. The samples were diluted to a final volume of 0.5 ml in PBS containing 1 μg/ml of propidium iodide and analyzed on a FACScan® flow cytometer (Becton Dickinson, San Jose, Calif.). An amount of $5-20 \times 10^3$ cells were collected per sample using a FSC vs. SSC live gate to ignore erthrocytes and an FL3 vs. FL2 live gate to exclude dead propidium iodide stained cells.

Treatment of BM cells with albumin. Bone marrow cells ($2 \times 10^6$/ml) from CBA/J mice were cultured in 2 ml of f-DMEM medium containing 1% FCS in the presence or absence of rHuAFP, human albumin (HuAlb), or mouse albumin (MoAlb). At 4 days of culture, cells were harvested, stained with anti-H-$2K^k$, and analyzed in FACS. FIG. 12B shows percent cells that were H-$2K^{k,high}$ in medium without added AFP or supplemented with either rHuAFP, HuAlb, or MoAlb. FIG. 12B shows percent cells that were 1-$A^{k+}$ in medium without added AFP or supplemented with rHuAFP, HuAlb, or MoAlb.

Bone Marrow Reconstitution in the Presence of AFP In Vitro and In Vivo

Enhanced BM Cell Recovery in the Presence of rHuAFP.

The impact of AFP to enhance BM cell reconstitution following sublethal gamma irradiation was analyzed by irradiating BM cells from C.B-17 mice with a dose of 600 rad. Thereafter, irradiated and non-irradiated cells were cultured in the absence or presence of IL-7 or rHuAFP. After 3 days of culture cells were harvested and cell densities were determined by the trypan blue dye exclusion test. Consistent with the data presented in FIG. 13 the highest cell density for non-irradiated cells was observed in the IL-7 cultures (FIG. 14A). BM cells from C.B-17 mice were irradiated with 600 rad. Thereafter, the irradiated and non-irradiated cells were cultured in the absence or presence of IL-7 or rHuAFP. After 3 days of culture, cells were harvested and cell densities were determined by the trypan blue day exclusion test. Conversely, following irradiation there was a significant enhancement in cell recovery among cells cultured in the presence of 100 µg/ml of rHuAFP (FIG. 14B).

All publications, manufacturer's instructions, patents, and patent applications mentioned in this specification are herein incorporated by reference to the same extent as if each individual publication or patent application was specifically and individually indicated to be incorporated by reference.

What is claimed is:

1. A method of treating psoriasis in a mammal in need thereof, said method comprising administering to said mammal a therapeutically effective amount of recombinant human alpha-fetoprotein or a biologically-active fragment thereof, wherein said fragment comprises an amino acid sequence set forth in SEQ ID NOS: 3-7 or 8.

2. The method of claim 1, further comprising administering to said mammal an immunosuppressive agent in an effective dose which is lower than the standard dose when said immunosuppressive agent is used by itself.

3. The method of claim 1, further comprising administering to said mammal a tolerizing agent.

4. The method of claim 2, wherein said immunosuppressive agent is cyclosporine.

5. The method of claim 2, wherein said immunosuppresive agent is a steroid, azathioprine, FK-506, or 15-deoxyspergualin.

6. The method of claim 1, wherein said recombinant human alpha-fetoprotein or fragment thereof is glycosylated.

7. The method of claim 1, wherein said recombinant human alpha-fetoprotein or fragment thereof is unglycosylated.

8. The method of claim 1, wherein said mammal is a human.

* * * * *

SEQUENCE LISTING

<160> NUMBER OF SEQ ID NOS: 18

<210> SEQ ID NO 1
<211> LENGTH: 2027
<212> TYPE: DNA
<213> ORGANISM: Homo sapiens

<400> SEQUENCE: 1

```
atattgtgct tccaccactg ccaataacaa ataaactagc aaccatgaag tgggtggaat      60 caatttttt aattttccta ctaaatttta ctgaatccag aacactgcat agaaatgaat     120
atggaatagc ttccatattg gattcttacc aatgtactgc agagataagt ttagctgacc     180
tggctaccat attttttgcc cagtttgttc aagaagccac ttacaaggaa gtaagcaaaa     240
tggtgaaaga tgcattgact gcaattgaga aacccactgg agatgaacag tcttcagggt     300
gtttagaaaa ccagctacct gcctttctgg aagaactttg ccatgagaaa gaaattttgg     360
agaagtacgg acattcagac tgctgcagcc aaagtgaaga gggaagacat aactgttttc     420
ttgcacacaa aaagcccact gcagcatgga tcccactttt ccaagttcca gaacctgtca     480
caagctgtga agcatatgaa gaagacaggg agacattcat gaacaaattc atttatgaga     540
tagcaagaag gcatcccttc ctgtatgcac ctacaattct tctttcggct gctgggtatg     600
agaaaataat tccatcttgc tgcaaagctg aaaatgcagt tgaatgcttc caaacaaagg     660
cagcaacagt tacaaaagaa ttaagagaaa gcagcttgtt aaatcaacat gcatgtccag     720
taatgaaaaa ttttgggacc cgaactttcc aagccataac tgttactaaa ctgagtcaga     780
agtttaccaa agttaatttt actgaaatcc agaaactagt cctggatgtg gcccatgtac     840
atgagcactg ttgcagagca gatgtgctgg attgtctgca ggatggggaa aaaatcatgt     900
cctacatatg ttctcaacaa gacactctgt caaacaaaat aacagaatgc tgcaaactga     960
ccacgctgga acgtggtcaa tgtataattc atgcagaaaa tgatgaaaaa cctgaaggtc    1020
tatctccaaa tctaaacagg tttttaggag atagagattt taaccaattt tcttcagggg    1080
aaaaaaatat cttcttggca agttttgttc atgaatattc aagaagacat cctcagcttg    1140
ctgtctcagt aattctaaga gttgctaaag gataccagga gttattggag aagtgtttcc    1200
agactgaaaa ccctcttgaa tgccaagata aggagaaga agaattacag aaatacatcc    1260
aggagagcca agcattggca aagcgaagct gcggcctctt ccagaaacta ggagaatatt    1320
acttacaaaa tgagtttctc gttgcttaca caaagaaagc cccccagctg acctcgtcgg    1380
agctgatggc catcaccaga aaaatggcag ccacagcagc cacttgttgc caactcagtg    1440
aggacaaact attggcctgt ggcgagggag cggctgacat tattatcgga cacttatgta    1500
tcagacatga aatgactcca gtaaacctg gtgttggcca gtgctgcact tcttcatatg    1560
ccaacaggag gccatgcttc agcagcttgg tggtggatga acatatgtc cctcctgcat    1620 tctctgatga caagttcatt ttccataagg atctgtgcca agctcagggt gtagcgctgc    1680
aaaggatgaa gcaagagttt ctcattaacc ttgtgaagca aagccacaa ataacagagg    1740
```

```
aacaacttga ggctctcatt gcagatttct caggcctgtt ggagaaatgc tgccaaggcc    1800
aggaacagga agtctgcttt gctgaagagg gacaaaaact gatttcaaaa actggtgctg    1860
ctttgggagt ttaaattact tcaggggaag agaagacaaa acgagtcttt cattcggtgt    1920
gaacttttct ctttaatttt aactgattta acacttttg tgaattaatg aaatgataaa    1980 gactttatg tgagatttcc ttatcacaga aataaaatat ctccaaa                    2027

<210> SEQ ID NO 2
<211> LENGTH: 590
<212> TYPE: PRT
<213> ORGANISM: Homo sapiens

<400> SEQUENCE: 2
```

Thr Leu His Arg Asn Glu Tyr Gly Ile Ala Ser Ile Leu Asp Ser Tyr
 1               5                  10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
        35                  40                  45

Lys Asp Ala Leu Thr Ala Ile Glu Lys Pro Thr Gly Asp Glu Gln Ser
 50                  55                  60

Ser Gly Cys Leu Glu Asn Gln Leu Pro Ala Phe Leu Glu Glu Leu Cys
 65                  70                  75                  80

His Glu Lys Glu Ile Leu Glu Lys Tyr Gly His Ser Asp Cys Cys Ser
                85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
        115                 120                 125

Cys Glu Ala Tyr Glu Glu Asp Arg Glu Thr Phe Met Asn Lys Phe Ile
    130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Pro Val Met
        195                 200                 205

Lys Asn Phe Gly Thr Arg Thr Phe Gln Ala Ile Thr Val Thr Lys Leu
    210                 215                 220

Ser Gln Lys Phe Thr Lys Val Asn Phe Thr Glu Ile Gln Lys Leu Val
225                 230                 235                 240

Leu Asp Val Ala His Val His Glu His Cys Cys Arg Ala Asp Val Leu
                245                 250                 255

Asp Cys Leu Gln Asp Gly Glu Lys Ile Met Ser Tyr Ile Cys Ser Gln
            260                 265                 270

Gln Asp Thr Leu Ser Asn Lys Ile Thr Glu Cys Cys Lys Leu Thr Thr
        275                 280                 285

Leu Glu Arg Gly Gln Cys Ile Ile His Ala Glu Asn Asp Glu Lys Pro
    290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val

```
                       325                 330                 335
His Glu Tyr Ser Arg Arg His Pro Gln Leu Ala Val Ser Val Ile Leu
                340                 345                 350

Arg Val Ala Lys Gly Tyr Gln Glu Leu Leu Glu Lys Cys Phe Gln Thr
            355                 360                 365

Glu Asn Pro Leu Glu Cys Gln Asp Lys Gly Glu Glu Leu Gln Lys
        370                 375                 380

Tyr Ile Gln Glu Ser Gln Ala Leu Ala Lys Arg Ser Cys Gly Leu Phe
385                 390                 395                 400

Gln Lys Leu Gly Glu Tyr Tyr Leu Gln Asn Glu Phe Leu Val Ala Tyr
                405                 410                 415

Thr Lys Lys Ala Pro Gln Leu Thr Ser Ser Glu Leu Met Ala Ile Thr
            420                 425                 430

Arg Lys Met Ala Ala Thr Ala Ala Thr Cys Cys Gln Leu Ser Glu Asp
        435                 440                 445

Lys Leu Leu Ala Cys Gly Glu Gly Ala Ala Asp Ile Ile Ile Gly His
    450                 455                 460

Leu Cys Ile Arg His Glu Met Thr Pro Val Asn Pro Gly Val Gly Gln
465                 470                 475                 480

Cys Cys Thr Ser Ser Tyr Ala Asn Arg Arg Pro Cys Phe Ser Ser Leu
                485                 490                 495

Val Val Asp Glu Thr Tyr Val Pro Pro Ala Phe Ser Asp Asp Lys Phe
            500                 505                 510

Ile Phe His Lys Asp Leu Cys Gln Ala Gln Gly Val Ala Leu Gln Arg
        515                 520                 525

Met Lys Gln Glu Phe Leu Ile Asn Leu Val Lys Gln Lys Pro Gln Ile
    530                 535                 540

Thr Glu Glu Gln Leu Glu Ala Leu Ile Ala Asp Phe Ser Gly Leu Leu
545                 550                 555                 560

Glu Lys Cys Cys Gln Gly Gln Glu Gln Glu Val Cys Phe Ala Glu Glu
                565                 570                 575

Gly Gln Lys Leu Ile Ser Lys Thr Gly Ala Ala Leu Gly Val
            580                 585                 590

<210> SEQ ID NO 3
<211> LENGTH: 197
<212> TYPE: PRT
<213> ORGANISM: Homo sapiens

<400> SEQUENCE: 3

Thr Leu His Arg Asn Glu Tyr Gly Ile Ala Ser Ile Leu Asp Ser Tyr
1               5                   10                  15

Gln Cys Thr Ala Glu Ile Ser Leu Ala Asp Leu Ala Thr Ile Phe Phe
                20                  25                  30

Ala Gln Phe Val Gln Glu Ala Thr Tyr Lys Glu Val Ser Lys Met Val
            35                  40                  45

Lys Asp Ala Leu Thr Ala Ile Glu Lys Pro Thr Gly Asp Glu Gln Ser
    50                  55                  60

Ser Gly Cys Leu Glu Asn Gln Leu Pro Ala Phe Leu Glu Glu Leu Cys
65                  70                  75                  80

His Glu Lys Glu Ile Leu Glu Lys Tyr Gly His Ser Asp Cys Cys Ser
                85                  90                  95

Gln Ser Glu Glu Gly Arg His Asn Cys Phe Leu Ala His Lys Lys Pro
            100                 105                 110
```

```
Thr Ala Ala Trp Ile Pro Leu Phe Gln Val Pro Glu Pro Val Thr Ser
            115                 120                 125
Cys Glu Ala Tyr Glu Glu Asp Arg Glu Thr Phe Met Asn Lys Phe Ile
        130                 135                 140
Tyr Glu Ile Ala Arg Arg His Pro Phe Leu Tyr Ala Pro Thr Ile Leu
145                 150                 155                 160
Leu Ser Ala Ala Gly Tyr Glu Lys Ile Ile Pro Ser Cys Cys Lys Ala
                165                 170                 175
Glu Asn Ala Val Glu Cys Phe Gln Thr Lys Ala Ala Thr Val Thr Lys
                180                 185                 190
Glu Leu Arg Glu Ser
                195

<210> SEQ ID NO 4
<211> LENGTH: 192
<212> TYPE: PRT
<213> ORGANISM: Homo sapiens

<400> SEQUENCE: 4

Ser Leu Leu Asn Gln His Ala Cys Pro Val Met Lys Asn Phe Gly Thr
1               5                   10                  15
Arg Thr Phe Gln Ala Ile Thr Val Thr Lys Leu Ser Gln Lys Phe Thr
                20                  25                  30
Lys Val Asn Phe Thr Glu Ile Gln Lys Leu Val Leu Asp Val Ala His
            35                  40                  45
Val His Glu His Cys Cys Arg Ala Asp Val Leu Asp Cys Leu Gln Asp
        50                  55                  60
Gly Glu Lys Ile Met Ser Tyr Ile Cys Ser Gln Gln Asp Thr Leu Ser
65                  70                  75                  80
Asn Lys Ile Thr Glu Cys Cys Lys Leu Thr Thr Leu Glu Arg Gly Gln
                85                  90                  95
Cys Ile Ile His Ala Glu Asn Asp Glu Lys Pro Glu Gly Leu Ser Pro
                100                 105                 110
Asn Leu Asn Arg Phe Leu Gly Asp Arg Asp Phe Asn Gln Phe Ser Ser
            115                 120                 125
Gly Glu Lys Asn Ile Phe Leu Ala Ser Phe Val His Glu Tyr Ser Arg
        130                 135                 140
Arg His Pro Gln Leu Ala Val Ser Val Ile Leu Arg Val Ala Lys Gly
145                 150                 155                 160
Tyr Gln Glu Leu Leu Glu Lys Cys Phe Gln Thr Glu Asn Pro Leu Glu
                165                 170                 175
Cys Gln Asp Lys Gly Glu Glu Glu Leu Gln Lys Tyr Ile Gln Glu Ser
                180                 185                 190

<210> SEQ ID NO 5
<211> LENGTH: 201
<212> TYPE: PRT
<213> ORGANISM: Homo sapiens

<400> SEQUENCE: 5

Gln Ala Leu Ala Lys Arg Ser Cys Gly Leu Phe Gln Lys Leu Gly Glu
1               5                   10                  15
Tyr Tyr Leu Gln Asn Glu Phe Leu Val Ala Tyr Thr Lys Lys Ala Pro
                20                  25                  30
Gln Leu Thr Ser Ser Glu Leu Met Ala Ile Thr Arg Lys Met Ala Ala
            35                  40                  45
```

-continued

```
Thr Ala Ala Thr Cys Cys Gln Leu Ser Glu Asp Lys Leu Leu Ala Cys
 50                  55                  60

Gly Glu Gly Ala Ala Asp Ile Ile Ile Gly His Leu Cys Ile Arg His
 65                  70                  75                  80

Glu Met Thr Pro Val Asn Pro Gly Val Gly Gln Cys Cys Thr Ser Ser
                 85                  90                  95

Tyr Ala Asn Arg Arg Pro Cys Phe Ser Ser Leu Val Val Asp Glu Thr
                100                 105                 110

Tyr Val Pro Pro Ala Phe Ser Asp Asp Lys Phe Ile Phe His Lys Asp
                115                 120                 125

Leu Cys Gln Ala Gln Gly Val Ala Leu Gln Arg Met Lys Gln Glu Phe
130                 135                 140

Leu Ile Asn Leu Val Lys Gln Lys Pro Gln Ile Thr Glu Glu Gln Leu
145                 150                 155                 160

Glu Ala Leu Ile Ala Asp Phe Ser Gly Leu Leu Glu Lys Cys Cys Gln
                165                 170                 175

Gly Gln Glu Gln Glu Val Cys Phe Ala Glu Glu Gly Gln Lys Leu Ile
                180                 185                 190

Ser Lys Thr Gly Ala Ala Leu Gly Val
                195                 200

<210> SEQ ID NO 6
<211> LENGTH: 389
<212> TYPE: PRT
<213> ORGANISM: Homo sapiens

<400> SEQUENCE: 6

Thr Leu His Arg Asn Glu Tyr Gly Ile Ala Ser Ile Leu Asp Ser Tyr
  1               5                  10                  15

Gln Cys Thr Ala Glu Ile Ser Leu Ala Asp Leu Ala Thr Ile Phe Phe
                 20                  25                  30

Ala Gln Phe Val Gln Glu Ala Thr Tyr Lys Glu Val Ser Lys Met Val
                 35                  40                  45

Lys Asp Ala Leu Thr Ala Ile Glu Lys Pro Thr Gly Asp Glu Gln Ser
 50                  55                  60

Ser Gly Cys Leu Glu Asn Gln Leu Pro Ala Phe Leu Glu Glu Leu Cys
 65                  70                  75                  80

His Glu Lys Glu Ile Leu Glu Lys Tyr Gly His Ser Asp Cys Cys Ser
                 85                  90                  95

Gln Ser Glu Glu Gly Arg His Asn Cys Phe Leu Ala His Lys Lys Pro
                100                 105                 110

Thr Ala Ala Trp Ile Pro Leu Phe Gln Val Pro Glu Pro Val Thr Ser
                115                 120                 125

Cys Glu Ala Tyr Glu Glu Asp Arg Glu Thr Phe Met Asn Lys Phe Ile
130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
                180                 185                 190

Glu Leu Arg Glu Ser Ser Leu Leu Asn Gln His Ala Cys Pro Val Met
                195                 200                 205

Lys Asn Phe Gly Thr Arg Thr Phe Gln Ala Ile Thr Val Thr Lys Leu
210                 215                 220
```

Ser Gln Lys Phe Thr Lys Val Asn Phe Thr Glu Ile Gln Lys Leu Val
225                 230                 235                 240

Leu Asp Val Ala His Val His Glu His Cys Cys Arg Ala Asp Val Leu
            245                 250                 255

Asp Cys Leu Gln Asp Gly Glu Lys Ile Met Ser Tyr Ile Cys Ser Gln
            260                 265                 270

Gln Asp Thr Leu Ser Asn Lys Ile Thr Glu Cys Cys Lys Leu Thr Thr
            275                 280                 285

Leu Glu Arg Gly Gln Cys Ile Ile His Ala Glu Asn Asp Glu Lys Pro
290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val
                325                 330                 335

His Glu Tyr Ser Arg Arg His Pro Gln Leu Ala Val Ser Val Ile Leu
            340                 345                 350

Arg Val Ala Lys Gly Tyr Gln Glu Leu Leu Glu Lys Cys Phe Gln Thr
            355                 360                 365

Glu Asn Pro Leu Glu Cys Gln Asp Lys Gly Glu Glu Glu Leu Gln Lys
370                 375                 380

Tyr Ile Gln Glu Ser
385

<210> SEQ ID NO 7
<211> LENGTH: 393
<212> TYPE: PRT
<213> ORGANISM: Homo sapiens

<400> SEQUENCE: 7

Ser Leu Leu Asn Gln His Ala Cys Pro Val Met Lys Asn Phe Gly Thr
1               5                   10                  15

Arg Thr Phe Gln Ala Ile Thr Val Thr Lys Leu Ser Gln Lys Phe Thr
            20                  25                  30

Lys Val Asn Phe Thr Glu Ile Gln Lys Leu Val Leu Asp Val Ala His
            35                  40                  45

Val His Glu His Cys Cys Arg Ala Asp Val Leu Asp Cys Leu Gln Asp
        50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
            100                 105                 110

Asn Leu Asn Arg Phe Leu Gly Asp Arg Asp Phe Asn Gln Phe Ser Ser
        115                 120                 125

Gly Glu Lys Asn Ile Phe Leu Ala Ser Phe Val His Glu Tyr Ser Arg
130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Leu Gln Lys Tyr Ile Gln Glu Ser
            180                 185                 190

Gln Ala Leu Ala Lys Arg Ser Cys Gly Leu Phe Gln Lys Leu Gly Glu

-continued

```
                195                 200                 205
Tyr Tyr Leu Gln Asn Glu Phe Leu Val Ala Tyr Thr Lys Lys Ala Pro
    210                 215                 220

Gln Leu Thr Ser Ser Glu Leu Met Ala Ile Thr Arg Lys Met Ala Ala
225                 230                 235                 240

Thr Ala Ala Thr Cys Cys Gln Leu Ser Glu Asp Lys Leu Leu Ala Cys
                245                 250                 255

Gly Glu Gly Ala Ala Asp Ile Ile Ile Gly His Leu Cys Ile Arg His
                260                 265                 270

Glu Met Thr Pro Val Asn Pro Gly Val Gly Gln Cys Cys Thr Ser Ser
            275                 280                 285

Tyr Ala Asn Arg Arg Pro Cys Phe Ser Ser Leu Val Val Asp Glu Thr
    290                 295                 300

Tyr Val Pro Pro Ala Phe Ser Asp Asp Lys Phe Ile Phe His Lys Asp
305                 310                 315                 320

Leu Cys Gln Ala Gln Gly Val Ala Leu Gln Arg Met Lys Gln Glu Phe
                325                 330                 335

Leu Ile Asn Leu Val Lys Gln Lys Pro Gln Ile Thr Glu Glu Gln Leu
            340                 345                 350

Glu Ala Leu Ile Ala Asp Phe Ser Gly Leu Leu Glu Lys Cys Cys Gln
        355                 360                 365

Gly Gln Glu Gln Glu Val Cys Phe Ala Glu Glu Gly Gln Lys Leu Ile
    370                 375                 380

Ser Lys Thr Gly Ala Ala Leu Gly Val
385                 390

<210> SEQ ID NO 8
<211> LENGTH: 325
<212> TYPE: PRT
<213> ORGANISM: Homo sapiens

<400> SEQUENCE: 8

Met Ser Tyr Ile Cys Ser Gln Gln Asp Thr Leu Ser Asn Lys Ile Thr
1               5                   10                  15

Glu Cys Cys Lys Leu Thr Thr Leu Glu Arg Gly Gln Cys Ile Ile His
                20                  25                  30

Ala Glu Asn Asp Glu Lys Pro Glu Gly Leu Ser Pro Asn Leu Asn Arg
            35                  40                  45

Phe Leu Gly Asp Arg Asp Phe Asn Gln Phe Ser Gly Glu Lys Asn
    50                  55                  60

Ile Phe Leu Ala Ser Phe Val His Glu Tyr Ser Arg Arg His Pro Gln
65                  70                  75                  80

Leu Ala Val Ser Val Ile Leu Arg Val Ala Lys Gly Tyr Gln Glu Leu
                85                  90                  95

Leu Glu Lys Cys Phe Gln Thr Glu Asn Pro Leu Glu Cys Gln Asp Lys
            100                 105                 110

Gly Glu Glu Glu Leu Gln Lys Tyr Ile Gln Glu Ser Gln Ala Leu Ala
        115                 120                 125

Lys Arg Ser Cys Gly Leu Phe Gln Lys Leu Gly Glu Tyr Tyr Leu Gln
    130                 135                 140

Asn Glu Phe Leu Val Ala Tyr Thr Lys Lys Ala Pro Gln Leu Thr Ser
145                 150                 155                 160

Ser Glu Leu Met Ala Ile Thr Arg Lys Met Ala Ala Thr Ala Ala Thr
                165                 170                 175
```

-continued

Cys Cys Gln Leu Ser Glu Asp Lys Leu Leu Ala Cys Gly Glu Gly Ala
            180                 185                 190

Ala Asp Ile Ile Gly His Leu Cys Ile Arg His Glu Met Thr Pro
        195                 200                 205

Val Asn Pro Gly Val Gly Gln Cys Cys Thr Ser Tyr Ala Asn Arg
    210                 215                 220

Arg Pro Cys Phe Ser Ser Leu Val Val Asp Glu Thr Tyr Val Pro Pro
225                 230                 235                 240

Ala Phe Ser Asp Asp Lys Phe Ile Phe His Lys Asp Leu Cys Gln Ala
                245                 250                 255

Gln Gly Val Ala Leu Gln Arg Met Lys Gln Glu Phe Leu Ile Asn Leu
            260                 265                 270

Val Lys Gln Lys Pro Gln Ile Thr Glu Glu Gln Leu Glu Ala Leu Ile
        275                 280                 285

Ala Asp Phe Ser Gly Leu Leu Glu Lys Cys Cys Gln Gly Gln Glu Gln
    290                 295                 300

Glu Val Cys Phe Ala Glu Glu Gly Gln Lys Leu Ile Ser Lys Thr Gly
305                 310                 315                 320

Ala Ala Leu Gly Val
            325

<210> SEQ ID NO 9
<211> LENGTH: 30
<212> TYPE: DNA
<213> ORGANISM: Homo sapiens

<400> SEQUENCE: 9
aaaaaaggta ccacactgca tagaaatgaa                                    30

<210> SEQ ID NO 10
<211> LENGTH: 33
<212> TYPE: DNA
<213> ORGANISM: Homo sapiens

<400> SEQUENCE: 10
aaaaaaggat ccttagcttt ctcttaattc ttt                                33

<210> SEQ ID NO 11
<211> LENGTH: 33
<212> TYPE: DNA
<213> ORGANISM: Homo sapiens

<400> SEQUENCE: 11
aaaaaaatcg atatgagctt gttaaatcaa cat                                33

<210> SEQ ID NO 12
<211> LENGTH: 33
<212> TYPE: DNA
<213> ORGANISM: Homo sapiens

<400> SEQUENCE: 12
aaaaaaggat ccttagctct cctggatgta ttt                                33

<210> SEQ ID NO 13
<211> LENGTH: 33
<212> TYPE: DNA
<213> ORGANISM: Homo sapiens

<400> SEQUENCE: 13
aaaaaaatcg atatgcaagc attggcaaag cga                                33

```
<210> SEQ ID NO 14
<211> LENGTH: 33
<212> TYPE: DNA
<213> ORGANISM: Homo sapiens

<400> SEQUENCE: 14
aaaaaaggat ccttaaactc ccaaagcagc acg                              33

<210> SEQ ID NO 15
<211> LENGTH: 33
<212> TYPE: DNA
<213> ORGANISM: Homo sapiens

<400> SEQUENCE: 15
aaaaaaatcg atatgtccta catatgttct caa                              33

<210> SEQ ID NO 16
<211> LENGTH: 9
<212> TYPE: PRT
<213> ORGANISM: Homo sapiens

<400> SEQUENCE: 16

Ser Tyr Ile Cys Ser Gln Gln Asp Thr
 1               5

<210> SEQ ID NO 17
<211> LENGTH: 21
<212> TYPE: DNA
<213> ORGANISM: Homo sapiens

<400> SEQUENCE: 17
gatctagaat tcggatccgg t                                           21

<210> SEQ ID NO 18
<211> LENGTH: 10
<212> TYPE: PRT
<213> ORGANISM: Homo sapiens

<400> SEQUENCE: 18

Ser Tyr Ile Cys Ser Gln Gln Asp Thr Leu
 1               5                  10
```